US011865183B2

(12) United States Patent
Godwin et al.

(10) Patent No.: US 11,865,183 B2
(45) Date of Patent: *Jan. 9, 2024

(54) CONJUGATES AND CONJUGATING REAGENTS COMPRISING A LINKER THAT INCLUDES AT LEAST TWO (–CH2—CH2—O—) UNITS IN A RING

(71) Applicant: POLYTHERICS LIMITED, Cambridge (GB)

(72) Inventors: Antony Godwin, London (GB); Andrew Kyle, Cambridge (GB); Nicholas Evans, Cambridge (GB)

(73) Assignee: POLYTHERICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/591,621

(22) Filed: Feb. 3, 2022

(65) Prior Publication Data

US 2022/0193249 A1    Jun. 23, 2022

Related U.S. Application Data

(63) Continuation of application No. 16/092,768, filed as application No. PCT/GB2017/051044 on Apr. 13, 2017, now Pat. No. 11,273,224.

(30) Foreign Application Priority Data

Apr. 14, 2016 (GB) .................................. 1606543.5

(51) Int. Cl.
| | |
|---|---|
| A61K 47/68 | (2017.01) |
| A61K 31/404 | (2006.01) |
| A61K 31/5365 | (2006.01) |
| A61K 47/65 | (2017.01) |
| A61K 47/54 | (2017.01) |
| A61K 47/60 | (2017.01) |
| A61K 31/10 | (2006.01) |
| A61K 31/407 | (2006.01) |
| C07K 16/28 | (2006.01) |
| C07K 16/40 | (2006.01) |
| A61K 39/00 | (2006.01) |
| A61K 31/40 | (2006.01) |

(52) U.S. Cl.
CPC .......... *A61K 47/6803* (2017.08); *A61K 31/40* (2013.01); *A61K 31/407* (2013.01); *A61K 47/54* (2017.08); *A61K 47/545* (2017.08); *A61K 47/60* (2017.08); *A61K 47/65* (2017.08); *A61K 47/6867* (2017.08); *A61K 47/6871* (2017.08); *C07K 16/2878* (2013.01); *C07K 16/40* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,838,274 | A | 6/1989 | Schweighardt et al. |
| 2007/0043212 | A1 | 2/2007 | Gee et al. |
| 2008/0176958 | A1 | 7/2008 | Davis et al. |
| 2016/0000933 | A1 | 1/2016 | Polukhtin |
| 2019/0328893 | A1 | 10/2019 | Godwin et al. |

FOREIGN PATENT DOCUMENTS

| | | |
|---|---|---|
| EP | 2260873 A1 | 12/2010 |
| JP | H07501332 A | 2/1995 |
| WO | 9309816 A1 | 5/1993 |
| WO | 2004060965 A2 | 7/2004 |
| WO | 2005007197 A2 | 1/2005 |
| WO | 2007055700 A1 | 5/2007 |
| WO | 2009047500 A1 | 4/2009 |
| WO | 2009152440 A1 | 12/2009 |
| WO | 2010100430 A1 | 9/2010 |
| WO | 2013090590 A1 | 6/2013 |
| WO | 2013190272 A1 | 12/2013 |
| WO | 2013190292 A2 | 12/2013 |
| WO | 2014064423 A1 | 5/2014 |
| WO | 2014064424 A1 | 5/2014 |
| WO | 2015057699 A2 | 4/2015 |
| WO | 2016063006 A1 | 4/2016 |

OTHER PUBLICATIONS

Kunstler et al. (European Journal of Medicinal Chemistry 45: 3645-3655, 2010).*
International Search Report and Written Opinion issued in corresponding International Patent Application No. PCT/GB2017/051044 dated Jul. 18, 2017 (11 pages).
Del Rosario et al., "Sulfhydryl Site-Specific Cross-Linking and Labeling of Monoclonal Antibodies by a Fluorescent Equilibrium Transfer Alkylation Cross-Link Reagent," Bioconjugate Chemistry, 1990, vol. 1, No. 1, pp. 51-59.
Khalili et al., "Comparative Binding of Disulfide-Bridged PEG-Fabs," Bioconjugate Chemistry, 2012, vol. 23, No. 11, pp. 2262-2277.
Liberatore et al., "Site-Directed Chemical Modification and Cross-Linking of a Monoclonal Antibody Using Equilibrium Transfer Alkylating Cross-Link Reagents," Bioconjugate Chemistry, 1990, vol. 1, No. 1, pp. 36-50 (12 pages).
Lyon et al., "Reducing hydrophobicity of homogeneous antibody-drug conjugates improves pharmacokinetics and therapeutic index," Nature Biotechnology, 2015, vol. 33, No. 7, pp. 733-735 (4 pages).

(Continued)

*Primary Examiner* — Bong-Sook Baek
(74) *Attorney, Agent, or Firm* — Kilyk & Bowersox, P.L.L.C.

(57) ABSTRACT

A conjugate comprising a protein or peptide conjugated to a therapeutic, diagnostic or labelling agent via a linker, characterised in that the linker includes at least two ~(CH2—CH2—O—)~ units within a ring, said ring being attached via a single tethering atom within the ring to the rest of the linker, or said ring being attached via two or more tethering atoms within the ring to the rest of the linker at a single point.

6 Claims, 5 Drawing Sheets

Specification includes a Sequence Listing.

(56) References Cited

OTHER PUBLICATIONS

Pompano, et al., "Crown ether-metal "sandwiches" as linking mechanisms in assembled nanoparticle films," Thin Solid Films, 2006, vol. 510, pp. 311-319.

* cited by examiner

Average tumour volume in mice dosed with 32

Individual tumour volumes in mice dosed with 32

Average tumour volume in mice dosed with 14

Individual tumour volumes in mice dosed with 14

Average tumour volume in mice dosed with 31

Individual tumour volume in mice dosed with 31

SEQUENCE LISTING

```
<160> NUMBER OF SEQ ID NOS: 2

<210> SEQ ID NO 1
<211> LENGTH: 446
<212> TYPE: PRT
<213> ORGANISM: Artificial
<220> FEATURE:
<223> OTHER INFORMATION: Brentuximab heavy chain

<400> SEQUENCE: 1

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                 245                 250                 255
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 2
<211> LENGTH: 218
<212> TYPE: PRT
<213> ORGANISM: Artificial
<220> FEATURE:
<223> OTHER INFORMATION: Brentuximab light chain

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

CONJUGATES AND CONJUGATING REAGENTS COMPRISING A LINKER THAT INCLUDES AT LEAST TWO (–CH2—CH2—O—) UNITS IN A RING

This application is a continuation of U.S. patent application Ser. No. 16/092,768 filed Oct. 11, 2018, which in turn is a National Stage Application of PCT/GB2017/051044, filed Apr. 13, 2017, which claims priority to United Kingdom Patent Application No. 1606543.5, filed Apr. 14, 2016.

FIELD OF INVENTION

This invention relates to novel conjugates and novel conjugating reagents.

BACKGROUND OF THE INVENTION

Much research has been devoted in recent years to the conjugation of a wide variety of payloads, for example therapeutic, diagnostic and labelling agents, to peptides and proteins for a wide range of applications. The protein or peptide itself may have therapeutic properties, and/or it may be a binding protein.

Peptides and proteins have potential use as therapeutic agents, and conjugation is one way of improving their properties. For example, water soluble, synthetic polymers, particularly polyalkylene glycols, are widely used to conjugate therapeutically active peptides or proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation". The PEG chain may carry a payload, for example a therapeutic, diagnostic or labelling agent.

Binding proteins, particularly antibodies or antibody fragments, are frequently conjugated. The specificity of binding proteins for specific markers on the surface of target cells and molecules has led to their extensive use either as therapeutic or diagnostic agents in their own right or as carriers for payloads which may include therapeutic, diagnostic or labelling agents. Such proteins conjugated to labels and reporter groups such as fluorophores, radioisotopes and enzymes find use in labelling and imaging applications, while conjugation to drugs such as cytotoxic agents and chemotherapy drugs to produce antibody-drug conjugates (ADCs) allows targeted delivery of such agents to specific tissues or structures, for example particular cell types or growth factors, minimising the impact on normal, healthy tissue and significantly reducing the side effects associated with chemotherapy treatments. Such conjugates have extensive potential therapeutic applications in several disease areas, particularly in cancer. Conjugates containing binding proteins frequently contain PEG.

Many methods of conjugating proteins and peptides have been reported in the literature. Probably the most commonly used process involves the use of conjugating reagents based on maleimides or succinimides. Such reagents are described in many publications, for example WO 2004/060965 and WO 2013/090590. An alternative approach which leads to more homogeneous products is described by Liberatore et al, Bioconj. Chem 1990, 1, 36-50, and del Rosario et al, Bioconj. Chem. 1990, 1, 51-59, which describe the use of reagents which may be used to cross-link across the disulfide bonds in proteins, including antibodies. WO 2005/007197 describes a process for the conjugation of polymers to proteins, using novel conjugating reagents having the ability to conjugate with both sulfur atoms derived from a disulfide bond in a protein to give novel thioether conjugates, while WO 2009/047500 describes the use of the same conjugating reagents to bond to polyhistidine tags attached to the protein. WO 2010/100430 describes reagents capable of forming a single carbon bridge across the disulfide bond in a protein. Other documents relating to the conjugation of proteins include WO 2014/064423, WO 2013/190292, WO 2013/190272 and EP 2260873.

WO 2014/064424 describes specific ADCs in which the drug is a maytansine and the antibody is bonded by cross-linking across a disulfide bond. WO 2014/064423 describes specific ADCs in which the drug is an auristatin and the antibody is bonded by cross-linking across a disulfide bond. The linkers illustrated in the Examples of these documents contain a PEG portion as part of the backbone of the linker, in which one end of the linear PEG chain is attached via a further portion of the linker to the drug, while the other end of the PEG chain is attached via a further portion of the linker to the antibody. This is a common structural pattern for ADCs. WO 2015/057699 and US 2016/0000933 describe alternative structures in which a linear PEG chain is attached to the backbone of the linker.

WO 2009/152440 describes a small molecule conjugate compound comprising a targeting ligand; a therapeutic agent and/or an imaging agent; and a linker connecting the ligand to the therapeutic agent and/or the imaging agent. A very long list of possible linkers is included (para. 0060), and this includes crown ether (for chelating with metal). WO 2007/055700 is concerned with lanthanide chelates derived from diazacrown ethers having two ethyliminodiacetic acid side chains. Again, the crown ether is present because of its chelating ability.

Over recent years, the importance of the linker which links a payload to the protein or peptide in a conjugate, has become apparent. Often, the key decision to be taken is whether it is desired to have a cleavable linker, i.e. a linker which, on administration of the conjugate, degrades to release the free payload, or a non-cleavable linker. Another key decision is whether or not to include PEG in the linker. Subject to these considerations, in principle, any linker may be used. In practice, however, changes in structure of the linker may lead to differences in the properties either of the conjugating reagent or of the resulting conjugate.

One problem frequently found is that conjugates may be less storage stable than desired. This is particularly true when a cleavable linker is used, when it is desired that the conjugate should have a long shelf-life before administration but should then rapidly cleave on application, but it can be true for any linker. There is a need to increase the storage stability of conjugates. In addition, improved stability in vivo is desirable, as this can lead to increased biological activity. There is also a need to increase biological activity. Finally, there is a need to improve conjugation efficiency when making the conjugates, to provide highly homogeneous products, and to minimise aggregation during the conjugation process. We have now found that for a particular class of conjugate, the use of PEG-containing linkers of a particular structure, gives advantageous properties. Specifically, conjugates with high stability and/or potency may be obtained.

SUMMARY OF THE INVENTION

The invention provides a conjugate comprising a protein or peptide conjugated to a therapeutic, diagnostic or labelling agent via a linker, characterised in that the linker includes at least two ~(CH$_2$—CH$_2$—O—)~ units within a ring, said ring being attached via a single tethering atom within the ring to the rest of the linker, or said ring being attached via two or more tethering atoms within the ring to the rest of the linker at a single point.

The invention also provides a conjugating reagent comprising a functional group capable of reacting with a protein or peptide, which reagent also comprises a therapeutic, diagnostic or labelling agent and a linker which includes at least two ~(CH$_2$—CH$_2$—O—)~ units within a ring, said ring being attached via a single tethering atom within the ring to the rest of the linker, or said ring being attached via two or more tethering atoms within the ring to the rest of the linker at a single point.

The invention also provides a process for the preparation of a conjugate according to the invention, which comprises reacting a protein or peptide with a conjugating reagent according to the invention, said ring being attached via a single tethering atom within the ring to the rest of the linker, or said ring being attached via two or more tethering atoms within the ring to the rest of the linker at a single point.

DETAILED DESCRIPTION OF THE INVENTION

The reagent of the invention may be represented schematically by the formula:

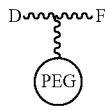

in which D represents the therapeutic, diagnostic or labelling agent, F represents a functional grouping capable of bonding to a protein or peptide, and

represents a ring which includes at least two ethylene glycol, ~(CH$_2$—CH$_2$—O—)~, units. The functional grouping F is capable of reacting with a protein or peptide as explained in more detail below.

The conjugate of the invention may be represented schematically by the formula:

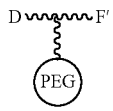

in which D represents the therapeutic, diagnostic or labelling agent, F' represents the protein or peptide bonded to the remainder of the conjugate via a protein or peptide bonding portion of the linker, and

represents a ring which includes at least two ethylene glycol, ~(CH$_2$—CH$_2$—O—)~, units.

The Polyethylene Glycol Ring

Throughout this specification, "polyethylene glycol ring" should be understood to mean a ring which includes at least two ethylene glycol, ~(CH$_2$—CH$_2$—O—)~, units. The ring may include two or more separate ~(CH$_2$—CH$_2$—O—)~ units, or it may include one or more units of the formula ~(CH$_2$—CH$_2$—O—)$_x$~ in which x is a number of at least 2. The ring may contain one or more additional atoms to complete the cyclic structure. Additional atoms may for example be nitrogen, carbon, oxygen, sulfur, silicon and/or phosphorus atoms.

It is a feature of the present invention that the ring is pendant to the rest of the linker rather than forming part of the backbone of the linker, i.e. it is attached to the rest of the linker but capable when in solution of moving flexibly relative to the rest of the linker. It is believed that, in contrast to the situation where the ring forms part of the backbone of the linker, as described in WO 2007/055700, this enables the conjugate, when in solution, to adopt a more flexible conformation than when the ring is rigidly held within the backbone of the linker, giving improved properties. Both of WO 2007/055700 and WO 2009/152440 include a ring in the linker in order to chelate a metal ion, which is a quite different objective to that of the present invention.

To this end, the ring may be attached via a single tethering atom within the ring to the rest of the linker at a single point, or it may be attached at two or more points. Alternatively, the ring may be attached via two or more tethering atoms within the ring to the rest of the linker at a single point. Tethering atoms may for example be nitrogen, carbon, phosphorus or silicon atoms, especially nitrogen and/or carbon atoms, and the atoms present at the point of attachment to the rest of the linker may for example be nitrogen or carbon atoms.

The following are schematic drawings of possible forms of attachment of the ring to the rest of the linker in conjugates or reagents of the invention, T representing a tethering atom in the ring, and PEG representing at least two ~(CH$_2$—CH$_2$—O—)~ units:

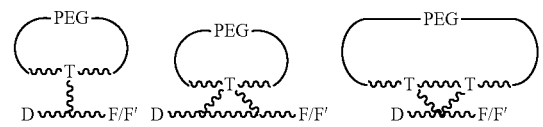

Specific examples of suitable rings include the following, where the symbol ~ indicates a point of incorporation of the ring into the linker:

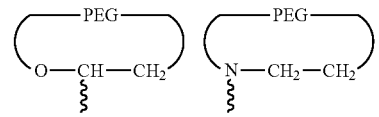

Preferably the ring is attached to the rest of the linker at a single point, and most preferably the ring is attached via a single tethering atom in the ring to the rest of the linker at a single point.

The ring may for example consist of ~(CH$_2$—CH$_2$—O—)$_x$~ units in which x is at least 2, preferably from 2 to 20. Alternatively, the ring may contain ~(CH$_2$—CH$_2$—O—)$_x$~ units in which x is at least 2, preferably from 2 to 50, especially from 2 to 20, but may also include one or more additional atoms as mentioned above, or may be derivatised in some other way.

Conjugates and reagents may be readily synthesised from crown ethers. Crown ethers are cyclic oligomers of ethylene glycol, and many different crown ethers are known, some of which consist entirely of ethylene glycol units, and some of which contain additional atoms within the ring. For example, aza-crown ethers contain a nitrogen atom, while diaza-crown ethers contain two nitrogen atoms. Many crown ethers are commercially available, and these provide convenient starting points for synthesis of the conjugates and reagents according to the invention. Crown ethers carrying functional groups through which they may be reacted with other compounds are known, for example crown ethers carrying carboxy, hydroxy, amino, or aldehyde groups are known, as are crown ethers fused to a benzene ring optionally carrying a functional group such as a carboxy, hydroxy, amino, isocyanate, nitro or aldehyde group.

Crown ethers are known to chelate cations, and perfluoro crown ethers have been described within U.S. Pat. No. 4,838,274 for use in MM. Therefore the conjugates of the invention may be used in applications within imaging techniques such as MM or PET.

Typical crown ethers which can be incorporated into the conjugates and reagents according to the invention include the structures shown below.

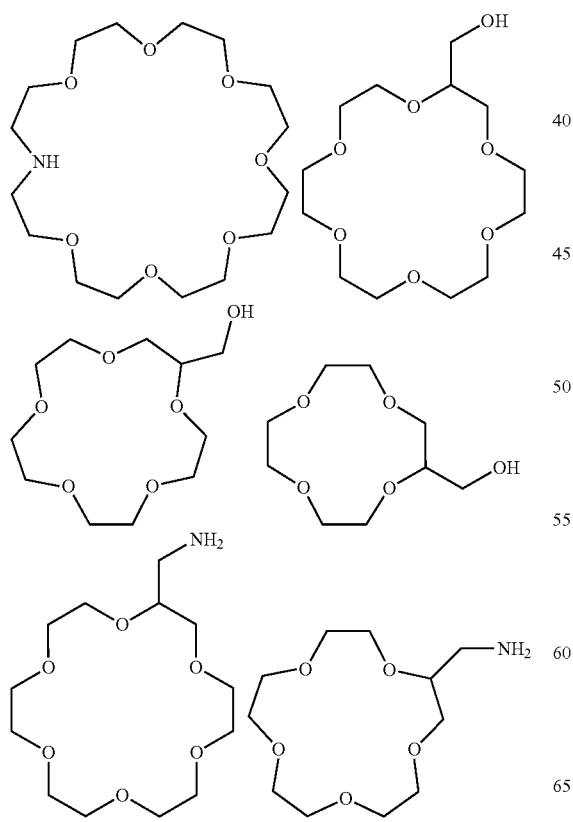

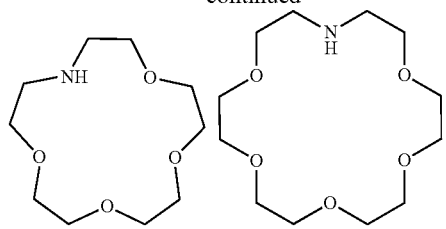

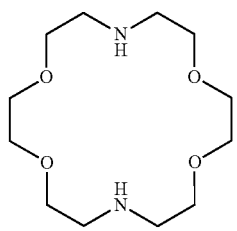

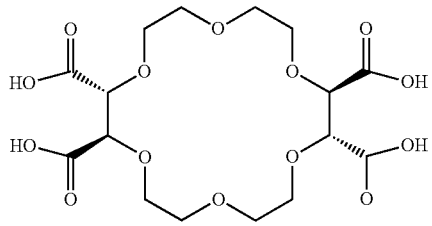

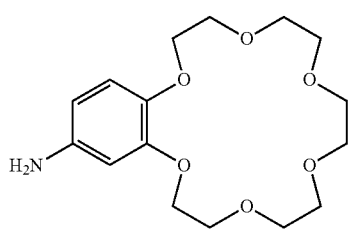

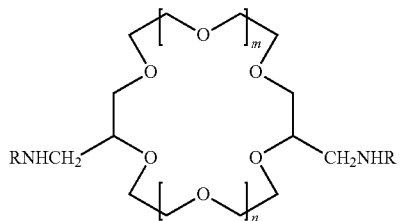

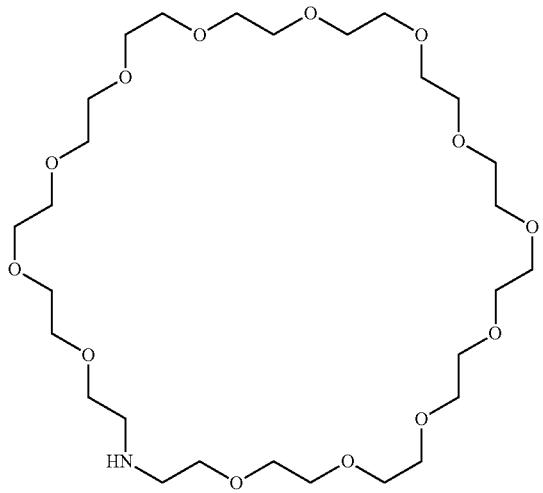

7
-continued
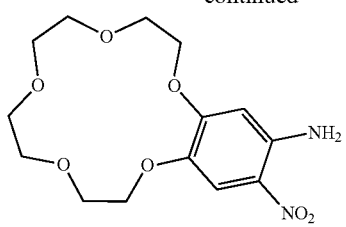
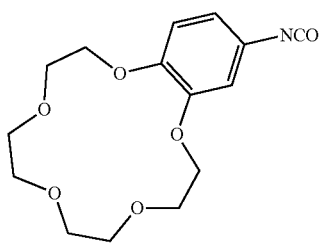
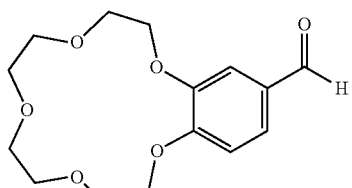
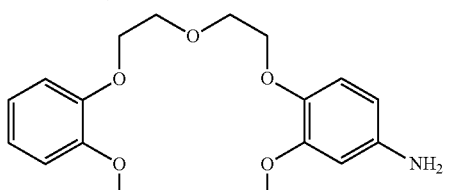
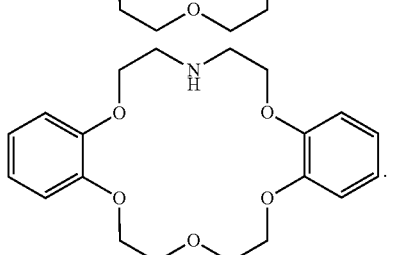
These may be attached to the backbone of the linker of the conjugates and reagents of the invention by reaction through atoms, especially nitrogen atoms, present within the ring, or via groups, for example hydroxy, amino, carboxy, aldehyde, isocyanate or nitro groups, present on a side-chain. Typical linkages are as shown below:
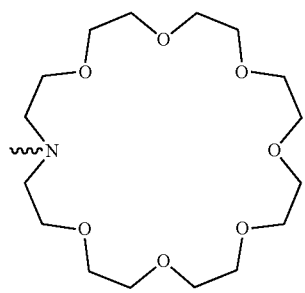
8
-continued
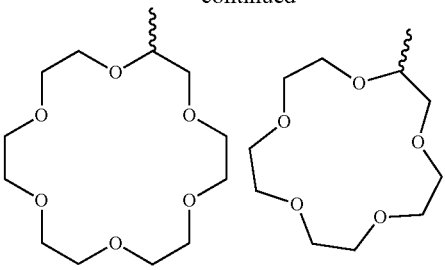
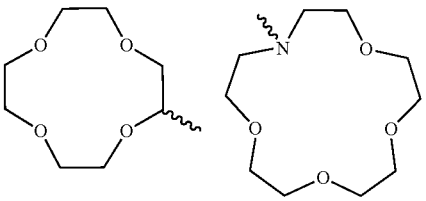
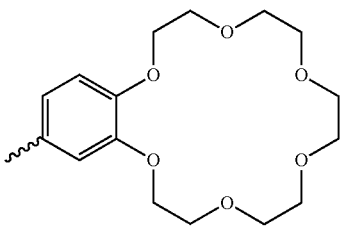
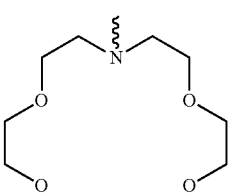
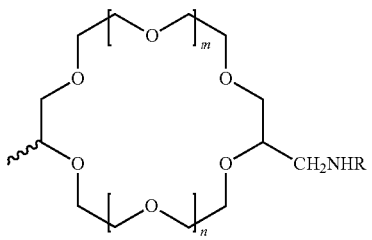
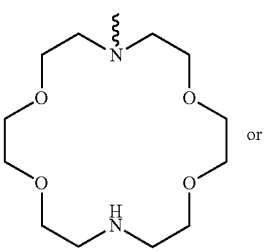
or

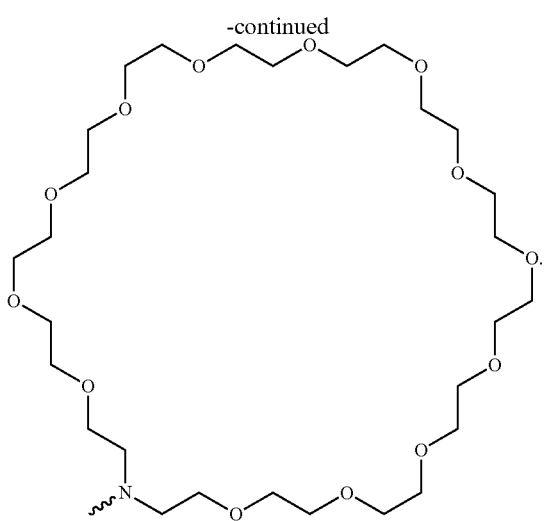

In addition to rings derived from crown ethers, rings derived from cryptands may be used in the present invention. Such rings are described for example in US 2014/0072900, and include the following:

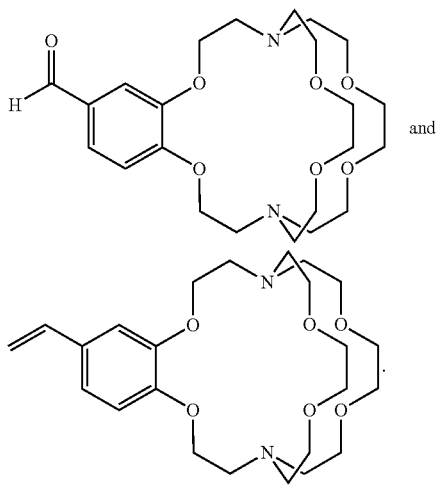

The conjugates and reagents of the invention may contain one ring including at least two ~(CH$_2$—CH$_2$—O—)~ units, or they may contain two or more such rings. The ring may be monocyclic, or it may be bi- or multi-cyclic. Two or more rings may be attached to the backbone of the linker, or they may be attached to each other, thus:

It will be understood that many different sizes and structures of rings are possible. The important feature of the invention is that a PEG chain forms part of a cyclic structure: this chain is not a linear PEG chain which forms part of the backbone of the linker, neither is it a pendant PEG chain which is tethered at one end to the linker but which has a free untethered end. Rather, it is a pendant PEG-containing cyclic structure which does not form part of the backbone of the linker.

In one preferred embodiment, all of the PEG in the conjugate or reagent according to the invention is present within one or more rings. In another embodiment, PEG may also be present elsewhere in the linker, specifically in the backbone of the linker or in a group linking the ring to the backbone of the linker, and this is discussed in more detail below.

The total number of ~(CH$_2$—CH$_2$—O—)~ units present in the conjugates and reagents of the invention will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications.

As with the total quantity of PEG present in the conjugates or reagents of the invention, the number of ~(CH$_2$—CH$_2$—O—)~ units present in the ring will depend on the intended application. For example the cyclic PEG portion may have a molecular weight up to 3,000 g/mole. However, cyclic groups containing as few as 2 ethylene glycol units, for example from 2 to 50 ethylene glycol units, are useful for some applications, and are present as a cyclic PEG group in one preferred embodiment of the invention. PEG-containing rings with 2, 3, 4, 5, 6, 7, 8, 9, 10, 11, 12, 13, 14, 15, 16, 17, 18, 19 or 20 repeat units, or 24, 36, 40 or 48 repeat units, may for example be used.

The Payload

The conjugates and reagents of the invention carry a payload which is a therapeutic, diagnostic or labelling agent. A single molecule of a therapeutic, diagnostic or labelling agent may be present, or two or more molecules may be present. The inclusion of one or more drug molecules, for example a cytotoxic agent or a toxin, is preferred. Auristatins, maytansinoids and duocarmycins are typical cytotoxic drugs. It is often preferred that drug conjugates, particularly antibody drug conjugates, should contain multiple copies of the drug. Labelling agents (which should be understood to include imaging agents) may for example include a radionuclide, a fluorescent agent (for example an amine derivatised fluorescent probe such as 5-dimethylaminonaphthalene-1-(N-(2-aminoethyl))sulfonamide-dansyl ethylenediamine, Oregon Green® 488 cadaverine (catalogue number 0-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L 2424, Molecular Probes), or a thiol derivatised fluorescent probe for example BODIPY® FL L-cystine (catalogue number B-20340, Molecular Probes). Biotin may also be used.

Preferably the payload is a therapeutic agent, especially one of those mentioned above.

The Protein

For convenience in this section and elsewhere, "protein" should be understood to include "protein and peptide" except where the context requires otherwise.

Suitable proteins which may be present in the conjugates of the invention include for example peptides, polypeptides, antibodies, antibody fragments, enzymes, cytokines, chemokines, receptors, blood factors, peptide hormones, toxin, transcription proteins, or multimeric proteins.

Enzymes include carbohydrate-specific enzymes, proteolytic enzymes and the like, for example the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerbrosidase, glucuronidase, and glutaminase.

Blood proteins include albumin, transferrin, Factor VII, Factor VIII or Factor IX, von Willebrand factor, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, for example IFN-α or IFN-β, colony stimulating factors, hemoglobin, cytokines, antibodies, antibody fragments, chorionicgonadotropin, follicle-stimulating hormone, thyroid stimulating hormone and tissue plasminogen activator.

Other proteins of interest are allergen proteins disclosed by Dreborg et al Crit. Rev. Therap. Drug Carrier Syst. (1990) 6 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosylated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes. Antibody-drug conjugates, based on an antibody or an antibody fragment, especially where the drug is a cytotoxic drug, for example an auristatin, maytansinoid or duocarmycin, are an especially preferred embodiment of the invention. Except where the context requires otherwise, any reference in this Specification to a conjugate of the invention should be understood to include a specific reference to an antibody drug conjugate.

An example of an antibody which may be useful in the conjugates of the invention is an anti-CD30 antibody, for example a chimeric monoclonal antibody cAC10, e.g. brentuximab. Brentuximab is the antibody portion of brentuximab vedotin (INN), trade name Adcetris®. Brentuximab vedotin is defined by the WHO as follows:

Immunoglobulin G1-kappa auristatin E conjugate, anti-[Homo sapiens TNFRSF8 (tumor necrosis factor receptor superfamily member 8, KI-1, CD30)], chimeric monoclonal antibody conjugated to auristatin E; gamma1 heavy chain (1-446) [Mus musculus VH (IGHV1-84*02-(IGHD)-IGHJ3*01) [8.8.10] (1-117) -Homo sapiens IGHG1*01 CH3 K130>del (118-446)], (220-218')-disulfide (if not conjugated) with kappa light chain (1'-218') [Mus musculus V-KAPPA (IGKV3-4*01-IGKJ1*01) [10.3.9] (1'-111') -Homo sapiens IGKC*01 (112'-218')]; (226-226")-disulfide dimer; conjugated, on an average of 3 to 5 cysteinyl, to monomethylauristatin E (MMAE), via a maleimidecaproyl-valyl-citrullinyl-p-aminobenzylcarbamate (mc-valcit-PABC) linker For the vedotin part, please refer to the document "INN for pharmaceutical substances: Names for radicals, groups and others"*.

```
Heavy chain
QIQLQQSGPE  VVKPGASVKI  SCKASGYTFT  DYYITWVKQK  PGQGLEWIGW      50

IYPGSGNTKY  NEKFKGKATL  TVDTSSSTAF  MQLSSLTSED  TAVYFCANYG     100

NYWFAYWGQG  TQVTVSAAST  KGPSVFPLAP  SSKSTSGGTA  ALGCLVKDYF     150

PEPVTVSWNS  GALTSGVHTF  PAVLQSSGLY  SLSSVVTVPS  SSLGTQTYIC     200

NVNHKPSNTK  VDKKVEPKSC  DKTHTCPPCP  APELLGGPSV  FLFPPKPKDT     250

LMISRTPEVT  CVVVDVSHED  PEVKFNWYVD  GVEVHNAKTK  PREEQYNSTY     300

RVVSVLTVLH  QDWLNGKEYK  CKVSNKALPA  PIEKTISKAK  GQPREPQVYT     350

LPPSRDELTK  NQVSLTCLVK  GFYPSDIAVE  WESNGQPENN  YKTTPPVLDS     400

DGSFFLYSKL  TVDKSRWQQG  NVFSCSVMHE  ALHNHYTQKS  LSLSPG         446

Light chain
DIVLTQSPAS  LAVSLGQRAT  ISCKASQSVD  FDGDSYMNWY  QQKPGQPPKV      50

LIYAASNLES  GIPARFSGSG  SGTDFTLNIH  PVEEEDAATY  YCQQSNEDPW     100

TFGGGTKLEI  KRTVAAPSVF  IFPPSDEQLK  SGTASVVCLL  NNFYPREAKV     150

QWKVDNALQS  GNSQESVTEQ  DSKDSTYSLS  STLTLSKADY  EKHKVYACEV     200

THQGLSSPVT  KSFNRGEC                                           218
```

Disulfide Bridges Location

| Intra-H | 22-96 | 144-200 | 261-321 | 367-425 |
|---|---|---|---|---|
|  | 22"-96" | 144"-200" | 261"-321" | 367"-425" |
| Intra-L | 23'-92' | 138'-198' |  |  |
|  | 23'''-92''' | 138'''-198''' |  |  |
| Inter-H-L* | 220-218' | 220"-218" |  |  |
| Inter-H-H* | 226-226" | 229-229" |  |  |

*Two or three of the inter-chain disulfide bridges are not present, the antibody being conjugated to an average of 3 to 5 drug linkers each via a thioether bond.

N-Glycosylation Sites 297, 297"

(WHO Drug Information, Vo. 25, No. 1, 2011; International Nonproprietary Names for Pharmaceutical Substances (INN), Recommended International Nonproprietary Names, List 65)

The protein may be derivatised or functionalised if desired. In particular, prior to conjugation, the protein, for example a native protein, may have been reacted with various blocking groups to protect sensitive groups thereon; or it may have been previously conjugated with one or more polymers or other molecules. It may contain a polyhistidine tag, which during the conjugation reaction can be targeted by the conjugating reagent.

Conjugating Reagents and Processes

Many conjugating reagents which can be used to conjugate a payload to a protein are known, and the novel conjugating reagents of the invention differ from these known reagents in the nature of the linker they contain. Such reagents contain at least one functional group F capable of reacting with a protein or peptide. For example, the conjugating reagent may comprise a functional group capable of reacting with at least one electrophile or, especially, nucleophile, present in the protein, the functional group being attached to the payload via the linker.

Any type of known conjugation reaction may be used to form the conjugates of the invention. For example, the reaction may be carried out using the known methods of thiol bonding, amine conjugation, or click chemistry. For example, the reagent may contain a maleimide group, an N-hydroxysuccinimide group, a click-chemistry group, for example an azide or alkyne group, an amine group, a carboxyl group, a carbonyl group, or an active ester group. Other possible approaches include the use of proteins that have been recombinantly engineered with an amino acid specifically for conjugation such as engineered cysteines or non-natural amino acids, and enzymatic conjugation through a specific enzymatic reaction such as with transglutaminase. The reaction site on the protein may be either nucleophilic or electrophilic in nature. Common protein conjugation sites are at lysine or cysteine amino acid residues or carbohydrate moieties. Alternatively, conjugation may occur at a polyhistidine tag which has been attached to a binding protein.

A conjugating reagent according to the invention is advantageously capable of reacting with a nucleophile in a protein and hence becoming chemically bonded thereto. As such the conjugating reagent typically includes at least one leaving group which is lost on reaction with a nucleophile. The conjugating reagent may, for example, include two or more leaving groups. Preferably the conjugating reagent according to the invention is capable of reacting with two nucleophiles. Advantageously, the conjugating reagent according to the invention comprises at least two leaving groups. If two or more leaving groups are present, these may be the same or different. Alternatively, a conjugating reagent may contain a single group which is chemically equivalent to two leaving groups and which single group is capable of reacting with two nucleophiles.

Nucleophilic groups include sulfur atoms and amine groups, and nucleophilic groups in proteins are for example provided by cysteine, lysine or histidine residues. In one preferred embodiment of the invention, a nucleophilic group is a sulfur atom present in a cysteine residue present in the protein. Such structures may be obtained by reduction of a disulfide bond present in the protein. In another embodiment, a nucleophilic group may be an imidazole group present in a histidine residue present in a polyhistidine tag attached to the protein.

One group of reagents is based on the bis-halo- or bis-thio-maleimides and derivatives thereof as described in Smith et al., *J. Am. Chem. Soc.*, 2010, 132, 1960-1965, and Schumacher et al., *Bioconj. Chem.*, 2011, 22, 132-136. These reagents contain the functional grouping:

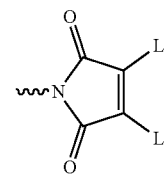

in which each L is a leaving group. The nitrogen atom of the maleimide ring is connected to the linker.

Similarly, maleimides containing a single leaving group L:

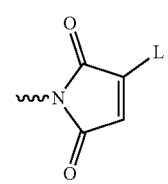

may be used. Again, the nitrogen atom of the maleimide ring is connected to the linker.

Also, maleimides lacking a leaving group:

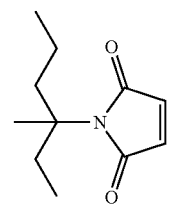

may be used. Again, the nitrogen atom of the maleimide ring is connected to the linker.

Another group of reagents are those described within WO201173391 An example of these reagents comprises the functional grouping:

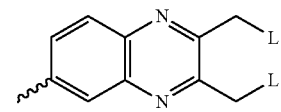

in which each L is a leaving group.

In an especially preferred embodiment of the invention, the conjugating reagent contains the functional grouping F:

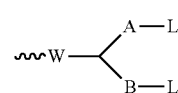

(I)

in which W represents an electron-withdrawing group, for example a keto group, an ester group —O—CO—, or a sulfone group —SO$_2$—; each of A and B independently represents a C$_{1-5}$alkylene or alkenylene chain; and either each L independently represents a leaving group, or both Ls together represent a leaving group. When reagents containing such groups react with proteins, a first leaving group L is lost to form in situ a conjugating reagent containing a functional grouping of formula:

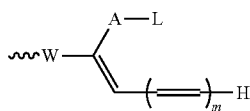
(II)

in which m is 0 to 4, which reacts with a first nucleophile. The second leaving group L is then lost, and reaction with a second nucleophile occurs. As an alternative to using a reagent containing the functional grouping I as starting material, reagents containing the functional grouping II may be used, as the functional groupings I and II are chemical equivalents of each other.

These conjugating reagents of the invention are of the general type disclosed in WO 2005/007197 and WO 2010/100430. Such reagents may for example be used to target two sulfur atoms obtained by reduction of a disulfide bond in a protein, or imidazole groups present in histidine residues present in a polyhistidine tag attached to a protein. It has been found that the incorporation of a cyclic PEG group according to the present invention into reagents of this type gives particularly good results, with conjugation reactions occurring efficiently to produce stable conjugates with a high degree of homogeneity.

A leaving group L may for example be —SP, —OP, —SO$_2$P, —OSO$_2$P, —N$^+$PR$^2$R$^3$, halogen, or —OØ, in which P represents a hydrogen atom or an alkyl (preferably C$_{1-6}$alkyl), aryl (preferably phenyl), or alkyl-aryl (preferably C$_{1-6}$alkyl-phenyl) group, or is a group which includes a portion —(CH$_2$CH$_2$O)$_n$— in which n is a number of two or more, and each of R$^2$ and R$^3$ independently represents a hydrogen atom, a C$_{1-4}$ alkyl group, or a group P, and Ø represents a substituted aryl, especially phenyl, group, containing at least one substituent, for example —CN, CF$_3$, —NO$_2$, —CO$_2$R$^a$, —COH, —CH$_2$OH, —COR$^a$, —OR$^a$, —OCOR$^a$, —OCO$_2$R$^a$, —SR$^a$, —SOR$^a$, —SO$_2$R$^a$, —NHCOR$^a$, —NR$^a$COR$^a$, —NHCO$_2$R$^a$, —NR$^a$CO$_2$R$^a$, —NO, —NHOH, —NR$^a$ OH, —CH=N—NR$^a$ COR$^a$, —N$^+$R$^a$$_3$, —, halogen, especially chlorine or, especially, fluorine, —C≡CR$^a$, and —CH=CR$^a$$_2$, in which each R$^a$ independently represents a hydrogen atom or an alkyl (preferably C$_{1-6}$alkyl), aryl (preferably phenyl), or alkyl-aryl (preferably C$_{1-6}$alkyl-phenyl) group. The presence of electron withdrawing substituents is preferred.

Conjugating reagents in which P represents a group which includes a portion —(CH$_2$CH$_2$O)$_n$— in which n is a number of two or more are the subject of our copending application GB 1418186, published as WO 2016/059377. This application discloses the following:

"The leaving group may for example include —(CH$_2$CH$_2$O)$_n$—R$^1$ where R$^1$ is a capping group. A very wide range of capping groups may be used. R$^1$ may for example be a hydrogen atom, an alkyl group, especially a C$_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —CH$_2$CH$_2$CO$_2$H or —CH$_2$CH$_2$NH$_2$, and may be prepared by functionalising the terminal unit of a —(CH$_2$CH$_2$O)$_n$— chain.

Alternatively, rather than being terminated by a capping group, the —(CH$_2$CH$_2$O)$_n$— group may have two points of attachment within the conjugating reagent such that chemically the equivalent of two leaving groups are present, capable of reacting with two nucleophiles.

The —(CH$_2$CH$_2$O)$_n$— portion of the leaving group is based on PEG, polyethylene glycol. The PEG may be straight-chain or branched, and it may be derivatised or functionalised in any way. n is a number of 2 or more, for example 2, 3, 4, 5, 6, 7, 8, 9 or 10. For example, n may be from 5 to 9. Alternatively, n may be a number of 10 or more. There is no particular upper limit for n. n may for example be 150 or less, for example 120 or less, for example 100 or less. For example n may be from 2 to 150, for example from 7 to 150, for example from 7 to 120. The PEG portion —(CH$_2$CH$_2$O)$_n$— of a leaving group may for example have a molecular weight of from 1 to 5 kDa; it may for example be 1 kDa, 2 kDa, 3 kDa, 4 kDa or 5 kDa. A leaving group may if desired contain two or more portions —(CH$_2$CH$_2$O)$_n$— separated by one or more spacers.

A leaving group in a conjugating reagent according to the invention is suitably of the formula —SP, —OP, —SO$_2$P, —OSO$_2$P, —N$^+$PR$^2$R$^3$, in which P is a group which includes a portion —(CH$_2$CH$_2$O)$_n$— and each of R$^2$ and R$^3$ independently represents a hydrogen atom, a C$_{1-4}$ alkyl group, or a group P. Preferably each of R$^2$ and R$^3$ represents a C$_{1-4}$alkyl group, especially a methyl group, or, especially, a hydrogen atom. Alternatively, the conjugating reagent may include a group of formula —S—P—S—; —O—P—O—; —SO$_2$—P—SO$_2$—; —OSO$_2$—P—OSO$_2$—; and —N$^+$R$^2$R$^3$—P—N$^+$R$^2$R$^3$—. Specific groups of this type include —S—(CH$_2$CH$_2$O)$_n$—S—, —O—(CH$_2$CH$_2$O)$_n$—O—; —SO$_2$—(CH$_2$CH$_2$O)$_n$—SO$_2$—; —OSO$_2$—(CH$_2$CH$_2$O)$_n$—OSO$_2$—; or —N$^+$R$^2$R$^3$—(CH$_2$CH$_2$O)$_n$—N$^+$R$^2$R$^3$—. They can also include groups of the type:

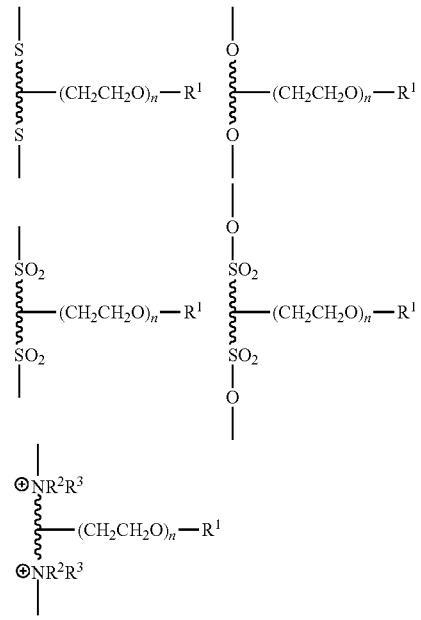

where the —(CH$_2$CH$_2$O)$_n$— group is carried by any suitable linking group, for example an alkyl group. These divalent groups are chemically equivalent to two leaving groups capable of reacting with two nucleophiles."

An especially preferred leaving group L present in a novel conjugating reagent according to the present invention is —SP or —SO$_2$P, especially —SO$_2$P. Within this group, one preferred embodiment is where P represents a phenyl or, especially, a tolyl group. Another preferred embodiment is where P represents a group which includes a portion —(CH$_2$CH$_2$O)$_n$—, especially one in which n has one of the values mentioned above, especially 7. An especially preferred leaving group L is —SO$_2$—(CH$_2$CH$_2$O)$_n$—H/Me, especially —SO$_2$—(CH$_2$CH$_2$O)$_7$—H/Me. Throughout this Specification, any reference to a leaving group L should be understood to include a specific reference to these preferred groups, especially —SO$_2$—(CH$_2$CH$_2$O)$_n$—H/Me, and more especially —SO$_2$—(CH$_2$CH$_2$O)$_7$—H/Me.

Preferably W represents a keto group. Preferably each of A and B represents —CH$_2$—.

Reagents of the formula I and II above form conjugates which include the grouping F':

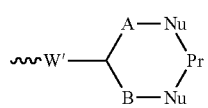
(III)

in which W' represents an electron withdrawing group or a group obtained by reduction of an electron withdrawing group, and Pr represents a protein or peptide bonded to A and B via nucleophiles Nu. The immediate product of the conjugation process (as described in more detail below) is a conjugate which contains an electron-withdrawing group W. However, the conjugation process is reversible under suitable conditions. This may be desirable for some applications, for example where rapid release of the protein is required, but for other applications, rapid release of the protein may be undesirable. It may therefore be desirable to stabilise the conjugates by reduction of the electron-withdrawing moiety to give a moiety which prevents release of the protein. Accordingly, the conjugation process may comprise an additional optional step of reducing the electron withdrawing group in the conjugate. The use of a borohydride, for example sodium borohydride, sodium cyanoborohydride, potassium borohydride or sodium triacetoxyborohydride, as reducing agent is particularly preferred.

Other reducing agents which may be used include for example tin (II) chloride, alkoxides such as aluminium alkoxide, and lithium aluminium hydride.

Thus, for example, a moiety W containing a keto group may be reduced to a moiety containing a CH(OH) group; an ether group CH·OR$^a$ may be obtained by the reaction of a hydroxy group with an etherifying agent; an ester group CH·O·C(O)R$^a$ may be obtained by the reaction of a hydroxy group with an acylating agent; an amine group CH·NH$_2$, CH·NHR$^a$ or CH·NR$^a_2$ may be prepared from a ketone by reductive amination; or an amide CH·NHC(O)R$^a$ or CH·N(C(O)R$^a$)$_2$ may be formed by acylation of an amine; in which R$^a$ represents a hydrogen atom or an alkyl (preferably C$_{1-6}$ alkyl), aryl (preferably phenyl), or alkyl-aryl (preferably C$_{1-6}$alkyl-phenyl) group. A sulfone may be reduced to a sulfoxide, sulfide or thiol ether.

Preferably the groupings F' and F have the formula:

(IIIa)

(Ia)

(IIa)

especially

(IIIb)

(IIIc)

(Ib)

(IIb)

In the above formulae, preferred leaving groups are as described above. Preferably each Nu is a sulfur atom.

Another preferred group of conjugating reagents contains the functional grouping:

~W—CR$^4$R$^{4'}$—CR$^4$·L·L'  (IV)

in which W has the meaning and the preferred meanings given above, and either each R$^4$ represents a hydrogen atom or a C$_{1-4}$ alkyl group, R$^{4'}$ represents a hydrogen atom, and either each L independently represents a leaving group, or both Ls together represent a leaving group; or each R$^4$ represents a hydrogen atom or a C$_{1-4}$ alkyl group, L represents a leaving group, and R$^{4'}$ and L' together represent a bond.

Another group of conjugating reagents includes the functional grouping:

~W—(CH=CH)$_p$—(CH$_2$)$_2$-L  (V) or

~W—(CH=CH)$_p$—CH=CH$_2$  (VI)

in which W has the meaning and preferred meanings given above and p represents 0 or an integer of from 1 to 4, preferably 0. An especially preferred reagent of this type includes the functional grouping:

~NH—CO—Ar—CO—(CH$_2$)$_2$-L  (Va) or

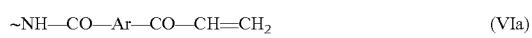
~NH—CO—Ar—CO—CH=CH$_2$  (VIa)

in which Ar represents an optionally substituted aryl, especially phenyl, group.

In all cases, preferred meanings for leaving groups L and L' are as mentioned above.

Conjugating reagents according to the invention may contain more than one functional grouping for reaction with a protein. For example, a reagent may contain a functional grouping, preferably of formula I or II, at one end of the molecule, and one or more additional functional groupings, elsewhere in the molecule. Such structures are described in for example Belcheva et al, J. Biomater. Sci Polymer Edn. 9(3), 207-226 and are useful in the synthesis of conjugates containing multiple proteins.

The novel conjugating reagents of the present invention may be prepared by methods analogous to known methods. Specific synthesis reactions are illustrated in the Examples which follow.

Conjugating reagents according to the invention may be reacted with a protein or peptide to form a conjugate according to the invention, and such a reaction forms a further aspect of the invention. Thus, a conjugating reagent including a suitable functional grouping, especially the functional grouping I or II, is reacted with a protein or peptide, especially an antibody or antibody fragment, to form a conjugate, especially one including the grouping III.

A key feature of using conjugating reagents of the formulae I or II is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. In reagents containing the functional grouping I, a leaving group serves to mask a latent conjugated double bond that is not exposed until after the first alkylation has occurred to give a reagent including the functional grouping II and bis-alkylation results from sequential and interactive Michael and retro-Michael reactions. The cross-functional alkylating agents may contain multiple bonds conjugated to the double bond or between the leaving group and the electron withdrawing group.

Where bonding to the protein is via two sulfur atoms derived from a disulfide bond in the protein, the process may be carried out by reducing the disulfide bond following which the reduced product reacts with the reagent according to the invention. Preferably the disulfide bond is reduced and any excess reducing agent is removed, for example by buffer exchange, before the conjugating reagent is introduced. The disulfide bond can be reduced, for example, with dithiothreitol, mercaptoethanol, or tris-carboxyethylphosphine using conventional methods.

Conjugation reactions may be carried out under similar conditions to known conjugation processes, including the conditions disclosed in WO 2005/007197, WO 2009/047500, WO 2014/064423, WO 2014/064424 and WO 2015/057699. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone, DMSO, DMF, MeCN) are typically conducted at temperatures up to ambient. In one preferred embodiment, the reaction is carried out in aqueous buffer which may contain a proportion of organic solvent, for example up to 20% by volume of organic solvent, typically from 5 to 20% by volume of organic solvent.

The protein can be effectively conjugated using a stoichiometric equivalent or a slight excess of conjugating reagent. However, it is also possible to conduct the conjugation reaction with an excess stoichiometry of conjugating reagent, and this may be desirable for some proteins. The excess reagent can easily be removed, for example by ion exchange chromatography or HPLC, during subsequent purification of the conjugate.

Of course, it is possible for more than one conjugating reagent to be conjugated to a protein, where the protein contains sufficient suitable attachment points. For example, in a protein which contains two different disulfide bonds, or in a protein which contains one disulfide bond and also carries a polyhistidine tag, it is possible to conjugate two molecules of reagent per molecule of protein, and such conjugates form part of the present invention.

The Linker

The conjugates and reagents of the present invention contain a linker which connects the therapeutic, diagnostic or labelling agent to the protein or peptide in the conjugates of the invention or to the functional grouping in conjugating reagents of the invention. The backbone of the linker is a continuous chain of atoms which runs from the therapeutic, diagnostic or labelling agent at one end to the protein or peptide at the other end. This linker must include one or more cyclic PEG portions, i.e. rings including at least two —(CH$_2$—CH$_2$—O)— units, as described above. It may also contain any other desired groups, particularly any of the conventional groups commonly found in this field.

Subsection (i). In one embodiment, the linker between the payload and the grouping of formula F'/F, and particularly that portion of the linker immediately adjacent the grouping of formula F'/F, may include an alkylene group (preferably a $C_{1-10}$ alkylene group), or an optionally-substituted aryl or heteroaryl group, any of which may be terminated or interrupted by one or more oxygen atoms, sulfur atoms, —NR$^a$ groups (in which R$^a$ represents a hydrogen atom or an alkyl (preferably $C_{1-6}$alkyl), aryl (preferably phenyl), or alkyl-aryl (preferably $C_{1-6}$alkyl-phenyl) group), keto groups, —O—CO— groups, —CO—O— groups, —O—CO—O, —O—CO—NR$^a$—, —NR—CO—O—, —CO—NR$^a$— and/or —NR$^a$·CO— groups. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially suitable linking groups are heteroaryl or, especially, aryl groups, especially phenyl groups. These may be adjacent a further portion of the linking group which is, or contains, a —NR$^a$·CO— or —CO·NR$^a$— group, for example an —NH·CO— or —CO·NH— group. Here and elsewhere throughout this Specification, where a group R$^a$ is present, this is preferably a $C_{1-4}$alkyl, especially a methyl group or, especially, a hydrogen atom.

Substituents which may be present on an optionally substituted aryl, especially phenyl, or heteroaryl group include for example one or more of the same or different substituents selected from alkyl (preferably $C_{1-4}$alkyl, especially methyl, optionally substituted by OH or $CO_2H$), $CF_3$, $NR^a{}_2$, —CN, —$NO_2$, —$CO_2R^a$, —COH, —$CH_2OH$, —$COR^a$, —$OR^a$, —$OCOR^a$, —$OCO_2R^a$, —$SR^a$, —$SOR^a$, —$SO_2R^a$, —$NR^aCOR^a$, —$NR^a \cdot CO_2R^a$, —NO, —$NR^a \cdot OH$, —CH=N—$NR^a \cdot COR^a$, —$N^+R^a{}_3$, halogen, for example fluorine or chlorine, —C≡$CR^a$, and —CH=$CR^a{}_2$, in which each $R^a$ independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example CN, $NO_2$, —$OR^a$, —$OCOR^a$, —$SR^a$, —$NR^a \cdot COR^a$, —NHOH and —$NR^a \cdot COR^a$, especially CN and $NO_2$.

Preferably the linker includes one of the above groups adjacent the grouping F'/F. One preferred group of conjugates and reagents includes those wherein the conjugate/reagent comprises a linker between the therapeutic, diagnostic or labelling agent and the grouping of formula F'/F, which linker includes an optionally substituted aryl or heteroaryl group immediately adjacent the grouping F'/F; and which linker also includes a —$NR^a \cdot C(O)$— or —C(O)·$NR^a$— group adjacent said aryl or heteroaryl group; thus having the formula —$NR^a \cdot C(O)$-(het)aryl-F' or —C(O)·$NR^a$-(het)aryl-F, wherein $R^a$ represents $C_{1-4}$ alkyl or hydrogen. Especially preferred are conjugates and conjugating reagents which include the grouping:

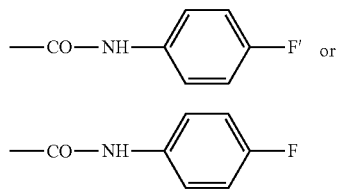

(VIIa)

(VIIIa)

or, especially:

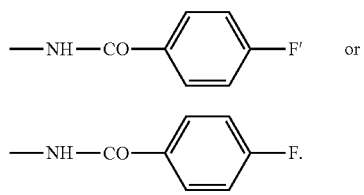

(VIIb)

(VIIIb)

In the above formulae, preferably F has the formula I or II, for example Ia, Ib, IIa or IIb above, and preferably F' has the formula III, for example IIIa, IIIb, or IIIc above.

In an alternative embodiment, conjugates and reagents of the invention include those which comprise a linker between the therapeutic, diagnostic or labelling agent and the grouping of formula F'/F, which linker includes an optionally substituted aryl or heteroaryl group immediately adjacent the grouping F'/F; and which linker also includes a —$NR^b \cdot C(O)$— or —C(O)·$NR^b$— group adjacent said aryl or heteroaryl group; thus having the formula —$NR^b \cdot C(O)$-(het)aryl-F' or —C(O)·$NR^b$-(het)aryl-F, wherein $R^b$ represents a group containing a polyethylene glycol ring.

Subsection (ii). In one embodiment, the linker may contain a degradable group, i.e. it may contain a group which breaks under physiological conditions, separating the payload from the protein to which it is, or will be, bonded. Alternatively, it may be a linker that is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where the linker contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

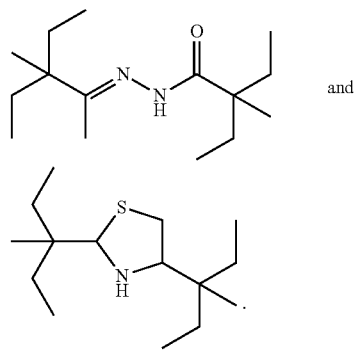

In a preferred embodiment, the linker includes

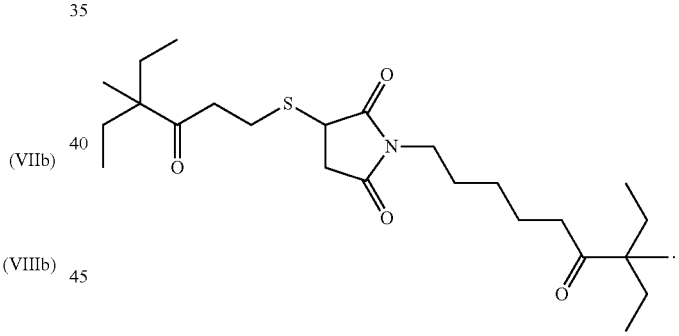

For example, it may include:

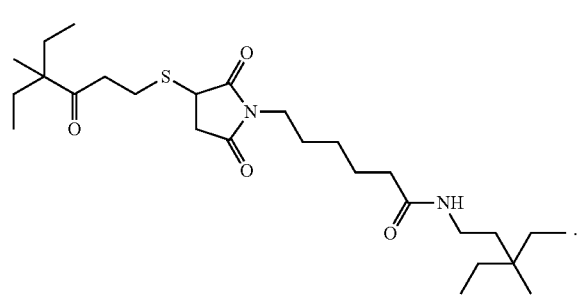 [SMILES: CCC(C)(CC)CCNC(=O)CCCCCN1C(=O)CC(SCCC(=O)C(C)(CC)CC)C1=O]

The linker may also be susceptible to degradation under reducing conditions. For example, it may contain a disulfide group that is cleavable on exposure to biological reducing agents, such as thiols. Examples of disulfide groups include:

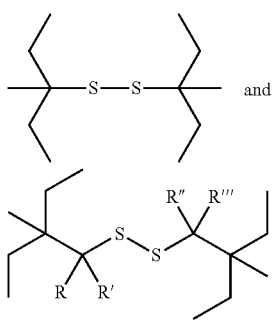

in which R, R', R" and R''' are each independently hydrogen or $C_{1-4}$alkyl. In a preferred embodiment the linker includes

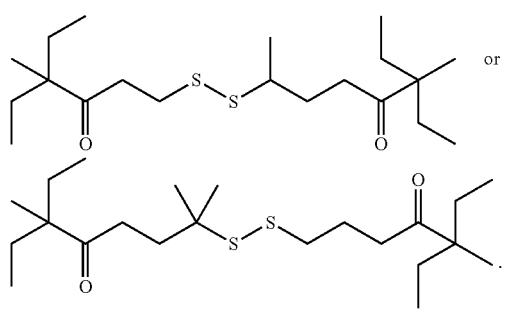

For example, it may include

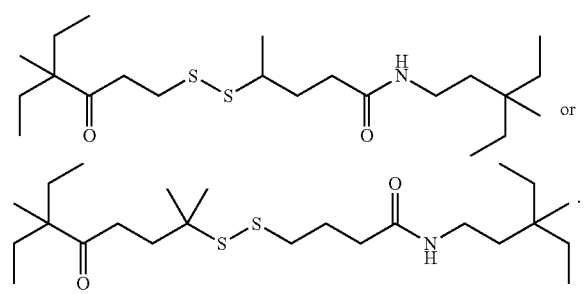

The linker may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys, Glu-Glu-Glu). For example, it may include an amino acid chain having from 1 to 5, for example 2 to 4, amino acids. Another example of a group susceptible to enzymatic degradation is:

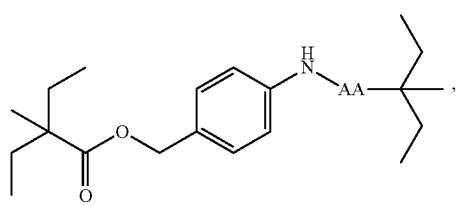

wherein AA represents a protease-specific amino acid sequence, such as Val-Cit.

In a preferred embodiment, the linker includes:

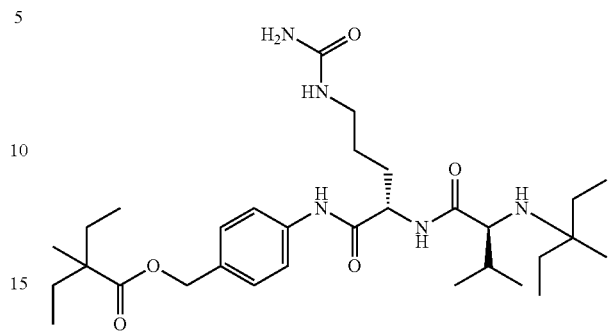

For example, it may include

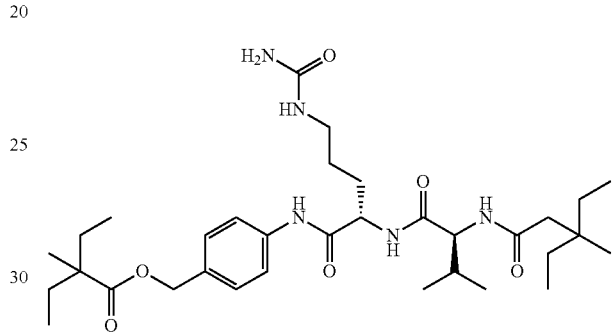

The linker may carry a single payload D, or more than one group D. Multiple groups D may be incorporated by the use of a branching linker, which may for example incorporate an aspartate or glutamate or similar residue. This introduces a branching element of formula:

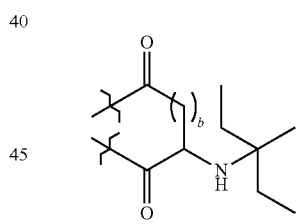

where b is 1, 2 or 3, b=1 being aspartate and b=2 being glutamate, and b=3 representing one preferred embodiment. Each of the acyl moieties in the above formula may be coupled to a group D. The branching group above may incorporate a —CO·CH$_2$— group, thus:

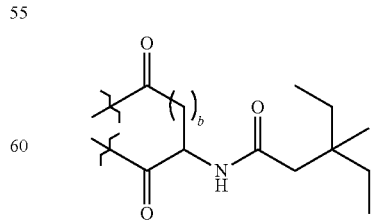

If desired, the aspartate or glutamate or similar residue may be coupled to further aspartate and/or glutamate and/or similar residues, for example:

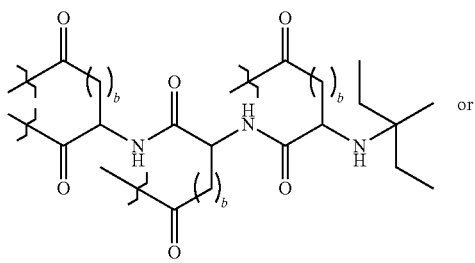

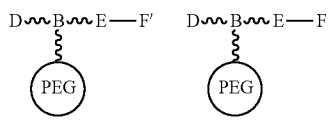

in which E represents one of the groups mentioned in subsection (i) above, and B represents one of the groups mentioned in this subsection (ii).

A specific, particularly preferred construction is shown below:

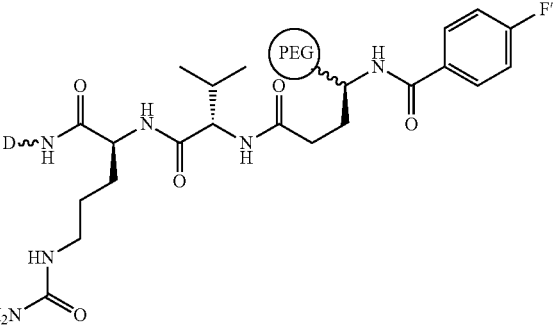

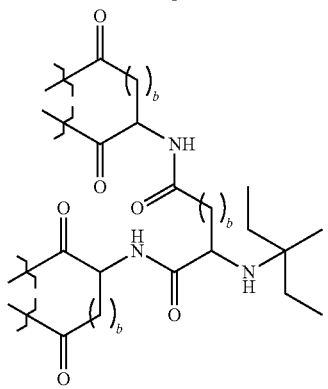

and so on.

In a similar way, the amino acids lysine, serine, threonine, cysteine, arginine or tyrosine or similar residues may be introduced to form a branching group, thus:

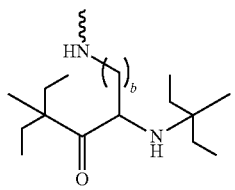

in which b is 4 for lysine, and

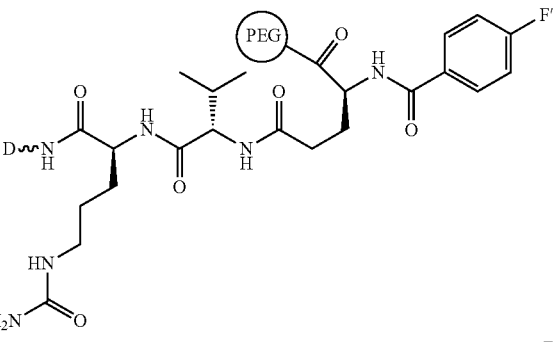

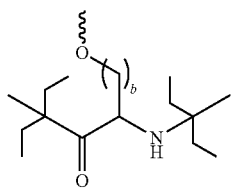

in which b is 1 for serine.

Similar branching groups may be used to incorporate the cyclic PEG group into the linker. So, for example, one of the branching elements mentioned above, for example an aspartate, glutamate, lysine or serine or similar residue, may be present with one branch leading to a drug D while the other leads to a branch containing the cyclic PEG group. The various linker portions mentioned above may be present at any location either before or after a branching group.

As will be apparent, many alternative configurations for the linker between the grouping F/F' and the payload are possible. One preferred configuration may be represented schematically as follows:

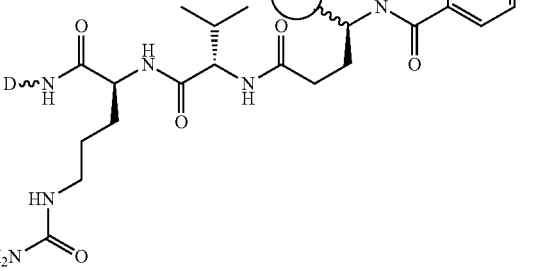

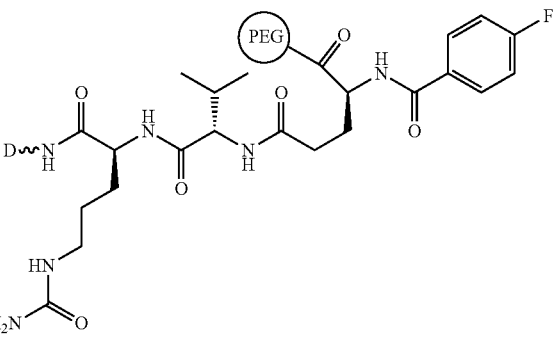

in which F' and F have the meanings and preferred meanings given above. Particularly preferred examples of such structures are as follows:
Subsection (iii). The linker which connects the therapeutic, diagnostic or labelling agent to the protein or peptide in the conjugates of the invention or to the functional grouping
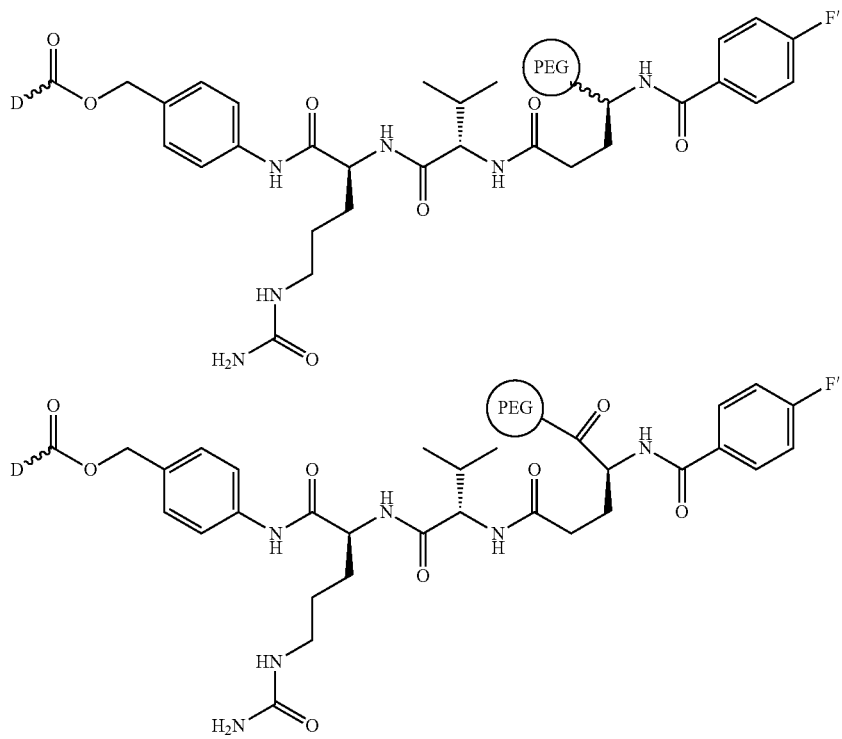
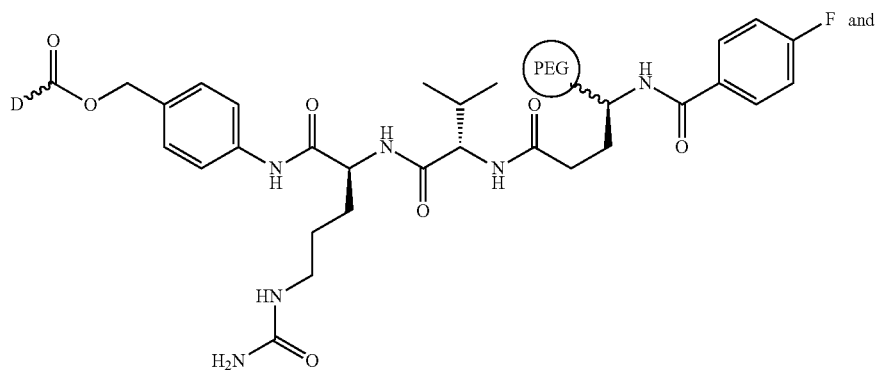
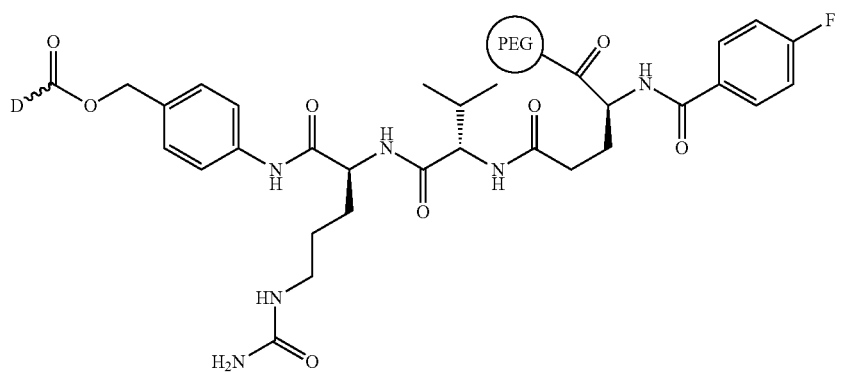

in the conjugating reagents of the invention may contain additional PEG in addition to the cyclic PEG group. It may for example contain PEG in the backbone of the linker, shown schematically thus:

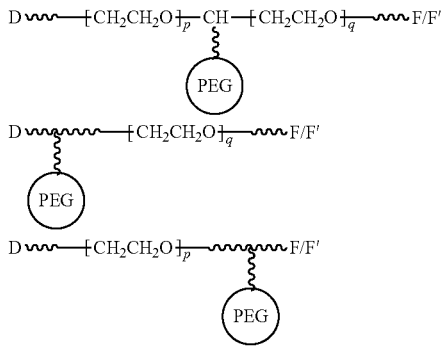

In these formulae, p and q represent the number of ethylene glycol units present in the various PEG chains present in the linker of the conjugate or the reagent in addition to the n ethylene glycol units present in the ring. For clarity, the PEG units are shown as straight-chain units, but it will be understood that any of the units may include branched chains.

Similarly, here and elsewhere, for clarity, a

group is shown as having only single points of attachment from the ring to the rest of the linker, but it should be understood that except where the context requires otherwise, multiple points of attachment as described above are equally possible.

Subsection (iv). The linker which connects the therapeutic, diagnostic or labelling agent to the protein or peptide in the conjugates of the invention or to the functional grouping in the conjugating reagents of the invention may contain two or more cyclic PEG groups. This may be illustrated schematically for two cyclic PEG groups thus:

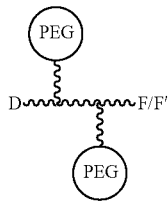

and obviously more than two cyclic PEG groups may similarly be present. The linker may or may not contain additional PEG in addition to the cyclic PEG groups, as described in subsection (iii) above.

Multiple cyclic PEG groups may be incorporated into the linker using any suitable method. A cyclic PEG group may for example be introduced by reaction with any reactive grouping present in any of the linker portions discussed above. Branching groups of the formulae described above may be used. For example, in one specific embodiment, two cyclic PEG groups may be incorporated by use of a structure:

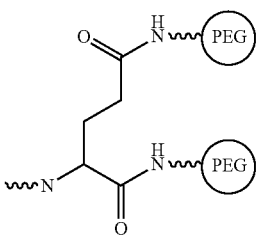

Alternatively, branching may be introduced by use of a polyol functionality, for example:

in which s is 0, 1 or 2, and t is 1 to 4. For example, in one specific embodiment, three cyclic PEG groups may be incorporated by use of a structure:

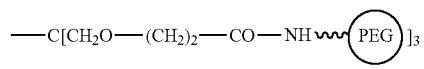

In some preferred embodiments of the conjugate, the conjugate includes a portion:

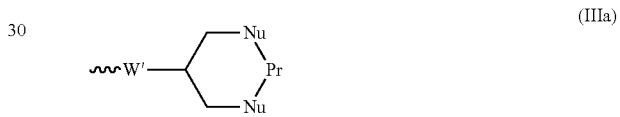

(IIIa)

in which W' represents an electron withdrawing group or a group obtained by reduction of an electron withdrawing group, and Pr represents a protein or peptide bonded via nucleophiles Nu, and which comprises an optionally substituted aryl or heteroaryl group immediately adjacent the group of formula IIIa; and which linker also includes a —NR$^a$·C(O)— or —C(O)·NR$^a$— group adjacent said aryl or heteroaryl group; wherein R$^a$ represents C$_{1-4}$ alkyl or hydrogen;

the protein or peptide is an antibody (e.g. an anti-CD30 antibody such as brentuximab);

the linker comprises a group

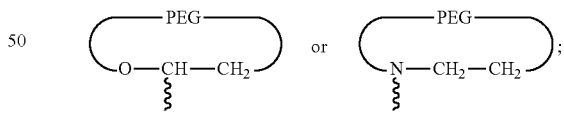

and the therapeutic, diagnostic or labelling agent is a cytotoxic agent (e.g. an auristatin, maytansine or duocarmycin).

In some preferred embodiments of the conjugate, the conjugate includes a portion:

(IIIa)

in which W' represents an electron withdrawing group or a group obtained by reduction of an electron withdrawing group, and Pr represents a protein or peptide bonded via nucleophiles Nu, and which comprises an optionally substituted aryl or heteroaryl group immediately adjacent the group of formula IIIa; and which linker also includes a —NR$^a$·C(O)— or —C(O)·NR$^a$— group adjacent said aryl or heteroaryl group; wherein R$^a$ represents C$_{1-4}$ alkyl or hydrogen;

the protein or peptide is an antibody (e.g. an anti-CD30 antibody such as brentuximab); the linker comprises a group

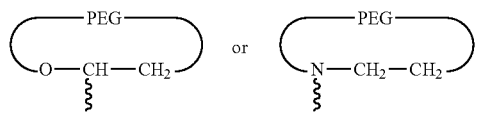

wherein the ring contains from 2 to 20 —CH$_2$CH$_2$—O— units (e.g. 2, 3, 4, 5, 6, 7, 8, 9, 10, 11, 12, 13, 14, 15, 16, 17, 18, 19, 20);

the linker comprises a degradable group which is

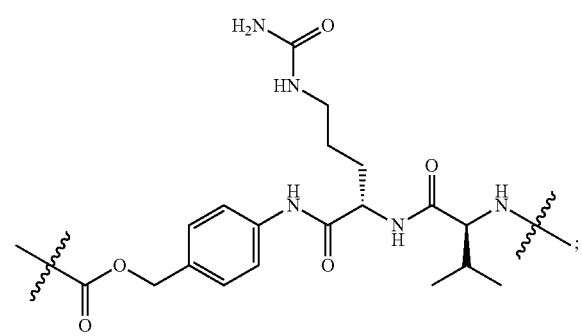 [SMILES: *N[C@H](C(=O)N[C@@H](CCCNC(N)=O)C(=O)Nc1ccc(COC(*)=O)cc1)C(C)C]

the linker comprises a branching group which is an aspartate, glutamate, lysine or serine residue to incorporate the cyclic PEG group into the linker; and the therapeutic, diagnostic or labelling agent is monomethyl auristatin E (MMAE).

In some preferred embodiments of the conjugate, the conjugate includes a portion:

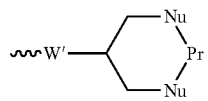

(IIIa)

in which W' represents an electron withdrawing group or a group obtained by reduction of an electron withdrawing group, and Pr represents a protein or peptide bonded via nucleophiles Nu, and which comprises an optionally substituted aryl or heteroaryl group immediately adjacent the group of formula IIIa; and which linker also includes a —NR$^a$·C(O)— or —C(O)·NR$^a$— group adjacent said aryl or heteroaryl group; wherein R$^a$ represents C$_{1-4}$ alkyl or hydrogen;

the protein or peptide is an antibody (e.g. an anti-CD30 antibody such as brentuximab); the linker comprises a group or;

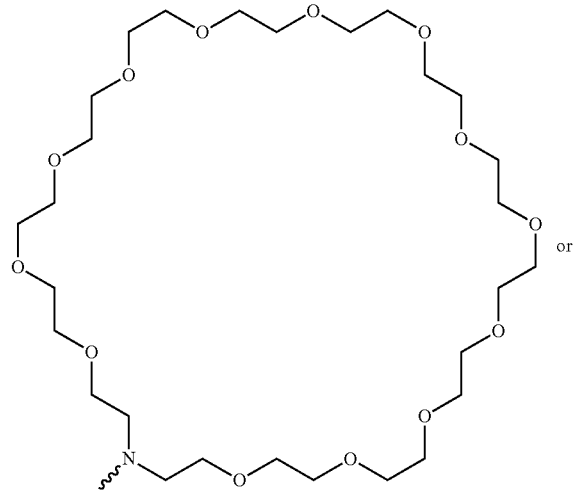

or

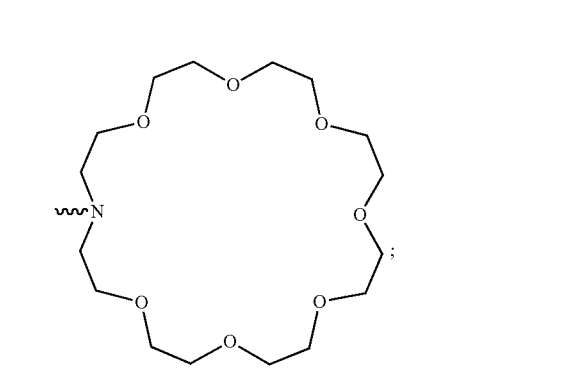

the linker comprises a degradable group which is

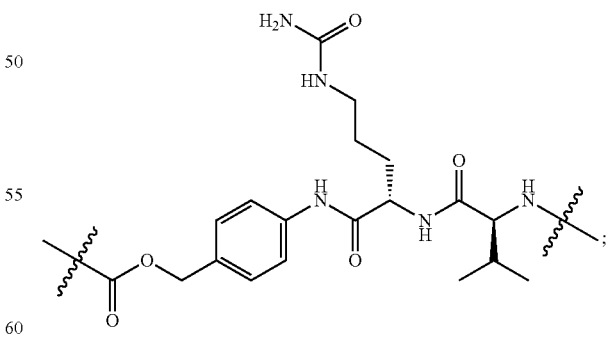

the linker comprises a branching group which is a glutamate residue to incorporate the cyclic PEG group into the linker; and the therapeutic, diagnostic or labelling agent is monomethyl auristatin E (MMAE).

In some preferred embodiments, the conjugate has the formula:

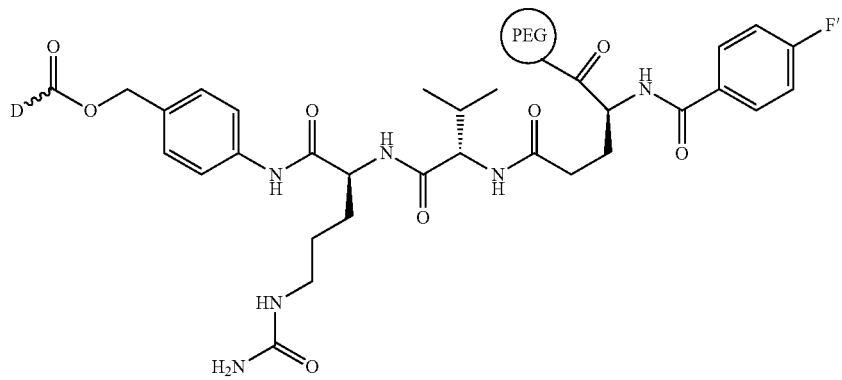

wherein D is a cytotoxic agent (e.g. an auristatin, maytansine or duocarmycin);

(PEG)

represents a ring which includes at least two ethylene glycol, ~(CH$_2$—CH$_2$—O—)~, units; F' is a group of formula $$\text{\textasciitilde CO}-\begin{array}{c}\text{Nu}\\|\\\text{Pr;}\\|\\\text{Nu}\end{array} \quad \text{(IIIb)}$$

and

Pr represents a protein or peptide bonded via nucleophiles Nu, which is an antibody (e.g. an anti-CD30 antibody such as brentuximab).

In some preferred embodiments, the conjugate has the formula:

wherein D is monomethyl auristatin E;

(PEG)

represents a group or $$\begin{array}{c}\text{PEG}\\ /\quad\quad\backslash\\\text{O}-\text{CH}-\text{CH}_2\end{array} \quad \text{or} \quad \begin{array}{c}\text{PEG}\\ /\quad\quad\backslash\\\text{N}-\text{CH}_2-\text{CH}_2\end{array}$$

wherein the ring contains from 2 to 20 —CH$_2$CH$_2$—O— units (e.g. 2, 3, 4, 5, 6, 7, 8, 9, 10, 11, 12, 13, 14, 15, 16, 17, 18, 19, 20);

F' is a group of formula $$\text{\textasciitilde CO}-\begin{array}{c}\text{Nu}\\|\\\text{Pr;}\\|\\\text{Nu}\end{array} \quad \text{(IIIb)}$$

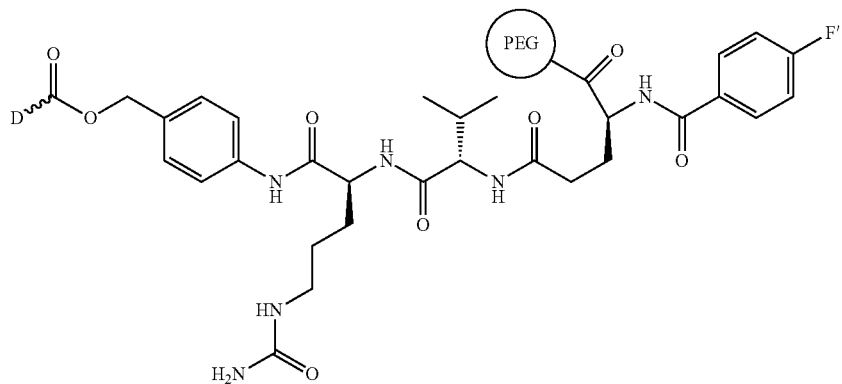

and

Pr represents a protein or peptide bonded via nucleophiles Nu, which is an antibody (e.g. an anti-CD30 antibody such as brentuximab).

In some preferred embodiments, the conjugate has the formula:

F' is a group of formula

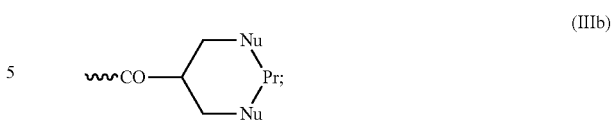
(IIIb)

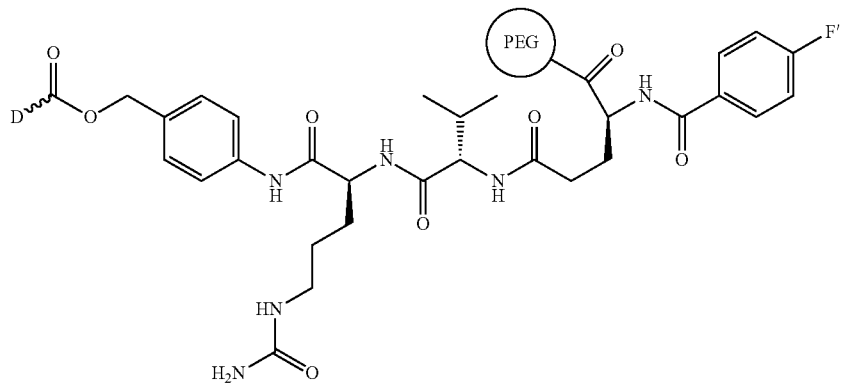

wherein D is monomethyl auristatin E;

represents

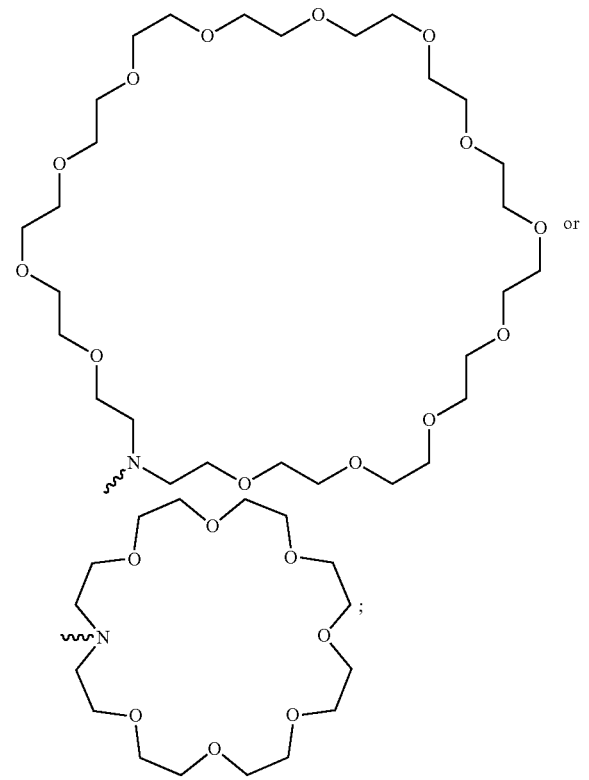

and

Pr represents a protein or peptide bonded via nucleophiles Nu, which is an antibody (e.g. an anti-CD30 antibody such as brentuximab).

Pharmaceutical Compositions and Utility

Conjugates according to the invention in which the payload is a therapeutic agent find utility in the treatment of various medical conditions depending on the nature of the payload. Typically the payload will be a cytotoxic agent and the invention finds utility in the treatment of cancer. Accordingly, the invention further provides a conjugate according to the present invention, particularly one in which the payload is a therapeutic agent and specifically a conjugate which is an antibody-drug conjugate, together with a pharmaceutically acceptable carrier, and optionally together with a further active ingredient. The invention further provides the use of such a conjugate in therapy, and finds utility in a method of treatment of a patient which comprises administering a conjugate or a pharmaceutical composition according to the invention to the patient. The invention further provides the use of a conjugate according to the invention in the manufacture of a medicament for the treatment of, for example, cancer.

BRIEF DESCRIPTION OF THE DRAWINGS

FIG. 2B showing (b) plots of individual tumour volumes over time in CB17-SCID mice following administration of vehicle or Adcetris® (brentuximab vedotin) (comparator) at 1 mg/kg on day 12 following tumour implantation. FIG. 3B showing (b) plots of individual tumour volumes over time in CB17-SCID mice following administration of vehicle or conjugate 32 (comparator) at 0.8 mg/kg on day 12 following tumour implantation.

FIG. 4B showing (b) plots of individual tumour volumes over time in CB17-SCID mice following administration of vehicle or conjugate 14 at 0.8 mg/kg on day 12 following tumour implantation.

FIG. 5B showing (b) plots of individual tumour volumes over time in CB17-SCID mice following administration of vehicle or conjugate 31 at 0.8 mg/kg on day 12 following tumour implantation.

Figure 1:
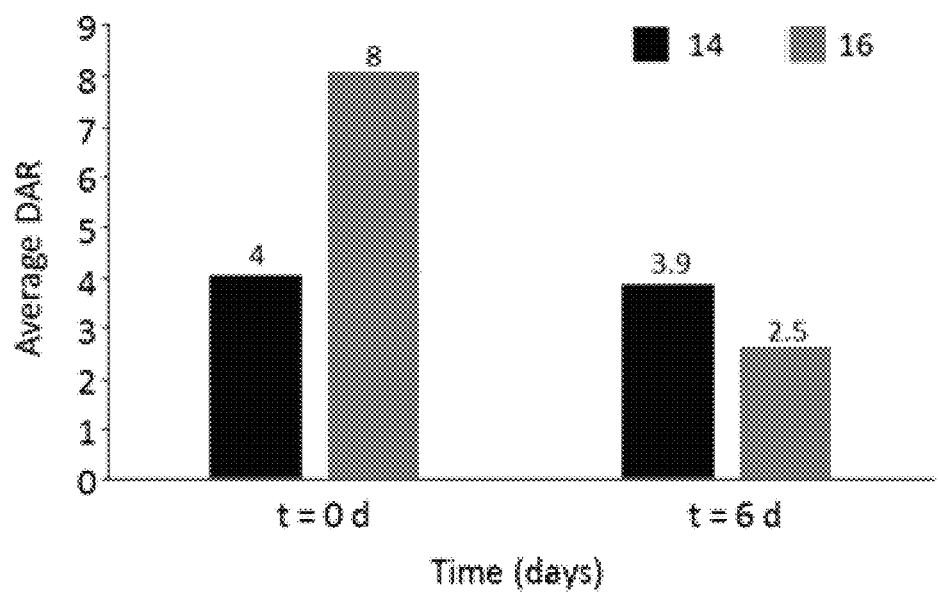
FIG. 1 shows the results of Example 8.
Figure 2A:
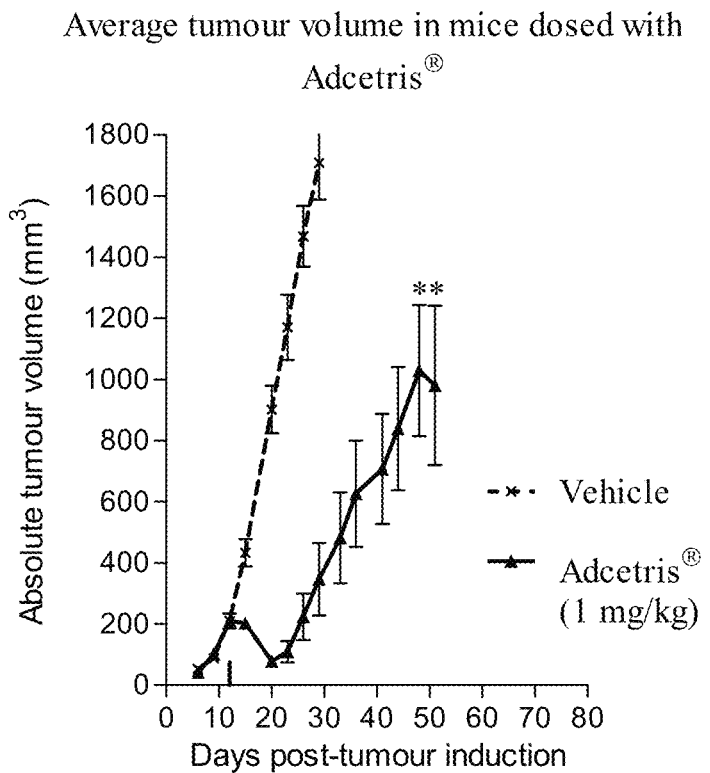
FIGS. 2A-2B show the results of mouse xenograft studies, with FIG. 2A showing (a) a plot of mean tumour volume±standard error over time in CB17-SCID mice following administration of vehicle or Adcetris® (brentuximab vedotin) (comparator) at 1 mg/kg on day 12 following tumour implantation.
Figure 2B:
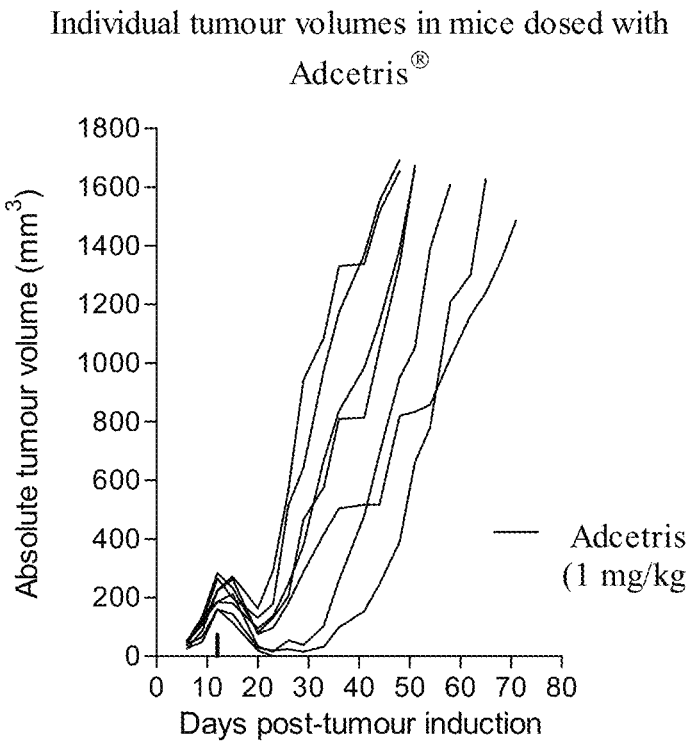

The following Examples illustrate the invention.

Example 1: Synthesis of Conjugation Reagent 1 Comprising the Auristatin Cytotoxic Payload, MAE

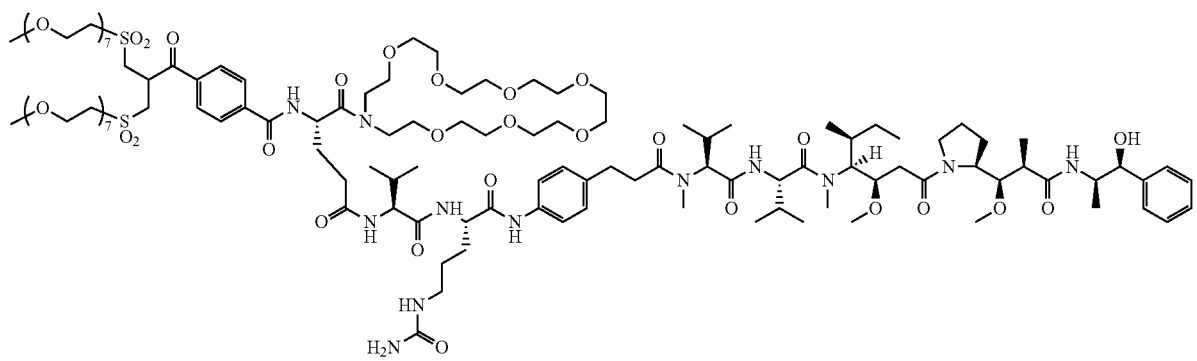

1

Step 1: Synthesis of Compound 2

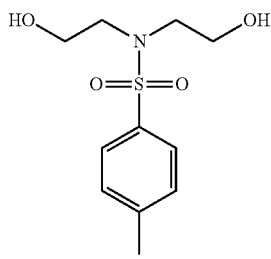

2

To a stirred solution of diethanolamine (2.5 g) and triethylamine (6.05 g) in dichloromethane (15 mL) was slowly added a solution of tosyl chloride (3.8 g) in dichloromethane (15 mL) at room temperature. After 2 h, water (25 mL) was added to the reaction mixture and the product was extracted with dichloromethane (5×30 mL). The combined organic extracts were dried over magnesium sulfate, the solution was then filtered and the volatiles removed in vacuo to yield compound 2 as a white solid (4.7 g). $^1$H NMR (400 MHz, CDCl$_3$) $\delta_H$ 7.68 (d, J=8.3 Hz, 2H), 7.30 (d, J=8.3 Hz, 2H), 3.84 (t, J=5.0 Hz, 4H), 3.56 (s, 2H), 3.24 (t, J=5.0 Hz, 4H), 2.41 (s, 3H). m/z [M+Na]$^+$ (282, 95%), [M+H]$^+$ (260, 100%).

Step 2: Synthesis of Compound 3

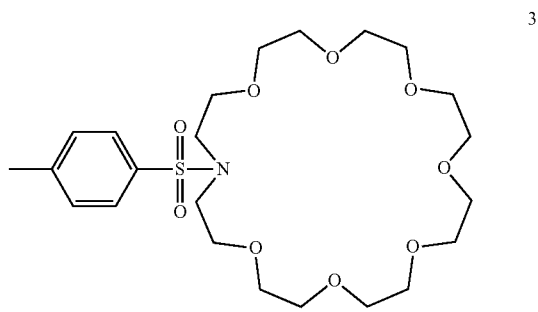 [SMILES: Cc1ccc(S(=O)(=O)N2CCOCCOCCOCCOCCOCCOCCOCC2)cc1]

3

A solution of compound 2 (176 mg) in anhydrous THF (2 mL) was added dropwise over a period of 1 h to a solution of sodium hydride (80 mg, 60% dispersion in mineral oil) in anhydrous THF (8 mL) at room temperature. After stirring for 1 h, a solution of hexaethyleneglycol di-p-toluene-sulfonate (400 mg) in anhydrous THF (2 mL) was added over a period of 2 h and the reaction mixture was stirred at room temperature for 72 h. Water (30 mL) was added and the THF was removed in vacuo. The aqueous solution was extracted with chloroform (4×25 mL), the organic phases were combined and dried over magnesium sulfate before the solution was filtered and concentrated in vacuo. The residue was then purified by reverse phase C18-column chromatography eluting with buffer A (v/v): water:55% acetonitrile: 0.05% trifluoroacetic acid and buffer B (v/v):acetonitrile: 0.05% trifluoroacetic acid (100:0 v/v to 0:100 v/v). The organic solvent was removed in vacuo and the aqueous solvent was removed by lyophilisation to give compound 3 as a colourless oil (78 mg). $^1$H NMR (400 MHz, CDCl$_3$) $\delta_H$ 7.68 (d, J=8.3 Hz, 2H), 7.26 (d, J=8.3 Hz, 4H), 3.67-3.58 (m, 24H), 3.58-3.53 (m, 4H), 3.38 (t, J=6.0 Hz, 4H), 2.40 (s, 3H). m/z [M+Na]*(528, 80%), [M+H]$^+$ (506, 50%).

Step 3: Synthesis of Compound 4

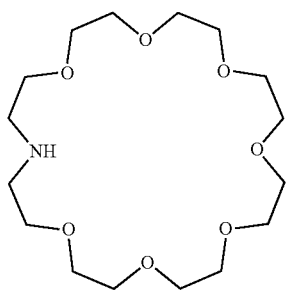

4

To a solution of compound 3 (78 mg) in anhydrous THF (6 mL) was added lithium aluminium hydride (1.13 mL, 1 M solution in THF) and the solution was heated at reflux for 16 h before the reaction mixture was cooled to 0° C. and quenched by the dropwise addition of water. The suspension was filtered and the precipitate washed with chloroform: ethanol (9:1 v/v, 5×6 mL). The filtrate and washings were combined and concentrated in vacuo to give compound 4 as a colourless oil (50 mg). m/z [M+Na]$^+$ (374, 70%), [M+H]$^+$ (352, 100%).

Step 4: Synthesis of Compound 5

To a solution of Fmoc-Glu-(OH)—OAll (48 mg) in DMF (1.0 mL) was added HATU (110 mg) and the solution was stirred for 30 min at 0° C. To this was added a solution of Val-Cit-PAB-MMAE.TFA salt (Levena Biopharma, 120 mg) and NMM (32 µL) in DMF (1 mL). The reaction mixture was stirred at 0° C. for 2.5 h. The solvent was concentrated in vacuo and the crude was dissolved in DMF (1.5 mL) before NN (32 µL) was added. Tetrakis(triphenylphosphine) palladium(0) (45 mg) was added to the reaction mixture which was then stirred at room temperature for 20 h. The reaction solution was concentrated in vacuo and the residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 5 as a white solid (98.0 mg). m/z [M+H]$^+$ (1475 Da, 100%), [M+2H]$^{2+}$ (738, 50%).

5

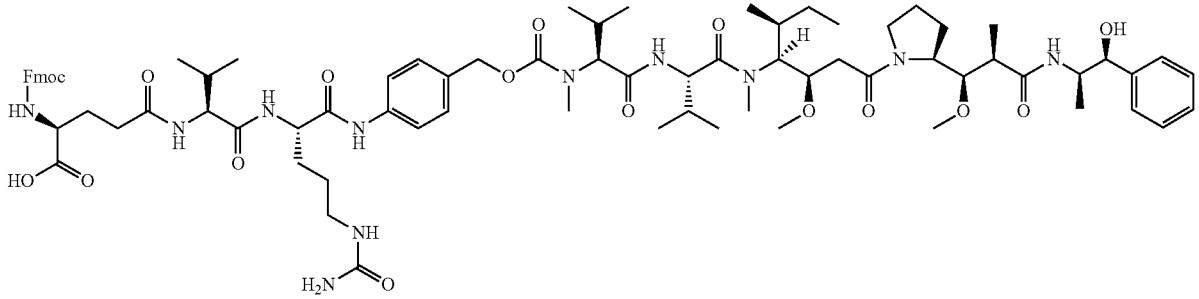

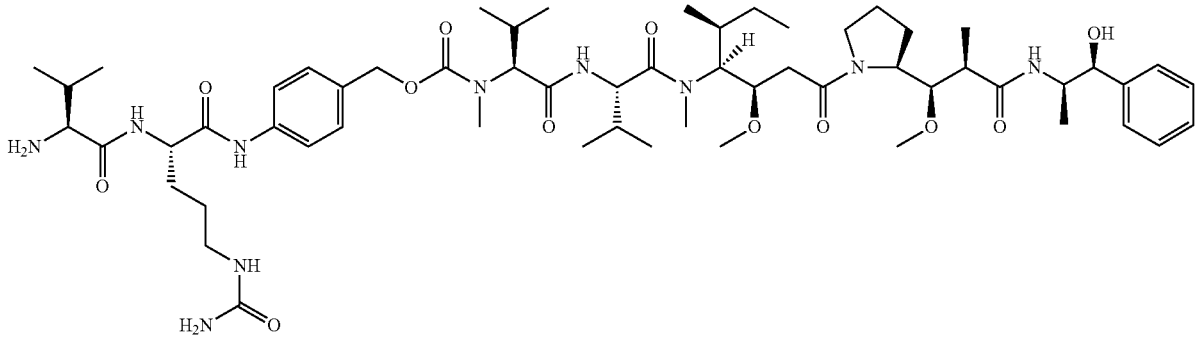

Val-Cit-PAB-MMAE

Step 5: Synthesis of Compound 6

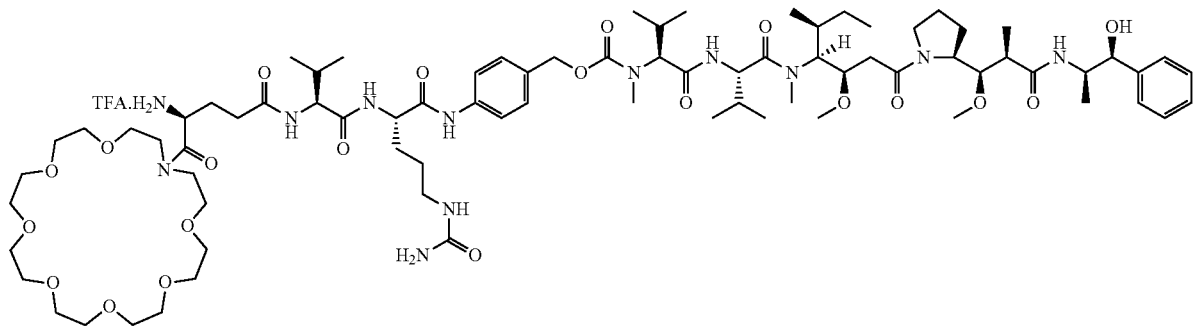

To a solution of compound 5 (15 mg) in DMF (0.5 mL) at 0° C. was added HATU (4.3 mg). The solution was stirred for 20 min at 0° C. before NMM (1.3 µL) was added and the solution was stirred for a further 10 min. To a separate solution of compound 4 (5 mg) in DMF (0.3 ml) was added NMM (1.3 µL) and the solution was stirred at room temperature for 30 min. The two solutions were then combined and additional quantities of HATU (4.3 mg) and NMM (1.3 µL) were added to the combined solution which was stirred for 16 h at room temperature. The reaction solution was concentrated in vacuo to give crude Fmoc-L-Glu-[Val-Cit-PAB-MMAE]-aza-24-crown-8 (18 mg). m/z [M+Na]+ (1831, 20%), [M+H]+ (1809, 20%), [M+2H]2+ (905, 100%). To a solution of Fmoc-L-Glu-[Val-Cit-PAB-MMAE]-aza-24-crown-8 (18 mg) in DMF (0.4 mL) was added piperidine (5 µL) and the solution was stirred for 20 min at room temperature. Additional piperidine (5 µL) was added and the solution was stirred for a further 25 min at room temperature. The reaction solution was concentrated in vacuo and the residue purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 6 as a colourless oil (8.5 mg). m/z [M+Na]+ (1609, 10%), [M+H]+ (1587, 20%), [M+2H]2+ (794, 100%).

Step 6: Synthesis of Compound 2

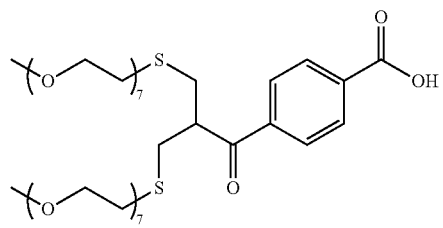

To a stirred solution of 4-[2,2-bis[(p-tolylsulfonyl)-methyl]acetyl]benzoic acid (1.5 g, Nature Protocols, 2006, 1(54), 2241-2252) in DMF (70 mL) was added alpha-methoxy-omega-mercapto hepta(ethylene glycol) (3.2 g) and triethylamine (2.5 mL). The resulting reaction mixture was stirred under an inert nitrogen atmosphere at room temperature. After 19 h, volatiles were removed in vacuo. The resulting residue was dissolved in water (2.4 mL) and purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 7 as a thick clear colourless oil (1.77 g). m/z [M+H]+ 901.

Step 7: Synthesis of Reagent 8

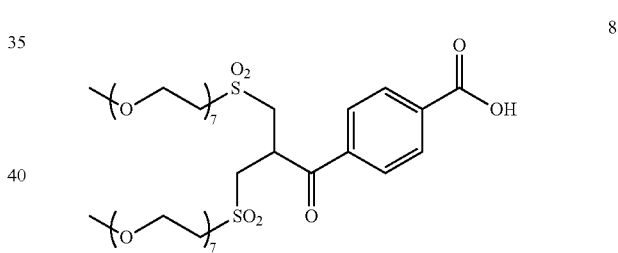

To a stirred solution of 7 (1.32 g) in methanol:water (18 mL, 9:1 v/v) at room temperature was added Oxone® (2.7 g). After 2.5 h, the volatiles were removed in vacuo and water was azeotropically removed with acetonitrile (2×15 mL). The resulting residue was dissolved in dichloromethane (3×10 mL), filtered through a column of magnesium sulfate and washed with dichloromethane (2×7 mL). The eluent and washings were combined and the volatiles were removed in vacuo to give a thick clear pale yellow oil (1.3 g). A portion of the residue (700 mg) was dissolved in water:acetonitrile (1.5 mL, 3:1 v/v), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 8 as a thick clear colourless oil (524 mg). m/z [M+H]+ 965.

Step 8: Synthesis of Reagent 1

To a solution of reagent 8 (6 mg) in DMF (0.3 mL) at 0° C. was added HATU (2.3 mg) The solution was stirred at 0°

C. for 20 min before NMM (0.6 μL) was added and the solution was stirred for a further 10 min. To a separate solution of compound 6 (8.5 mg) in DMF (0.3 mL) was added NMM (0.6 μL) and the solution was stirred at room temperature for 30 min. The two solutions were then combined and additional quantities of HATU (2.3 mg) and NMM (0.6 μL) were added and the solution was stirred at room temperature for 1 h. Further quantities of HATU (1.2 mg) and NMM (0.3 μL) were then added and the solution stirred at room temperature for 1.5 h. The reaction solution was concentrated in vacuo and the residue purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 1 as a colourless oil (10.7 mg). m/z $[M+Na]^+$ (2557, 5%), $[M+2H]^{2+}$ (1268, 40%), $[M+3H]^{3+}$ (845, 45%).

Example 2: Synthesis of Conjugation Reagent 9 Comprising the Auristatin Cytotoxic Payload, MMAE To a solution of tosyl chloride (307 mg) in dichloromethane (5 mL) was added a solution of dodecaethylene glycol (400 mg), triethylamine (255 μL) and DMAP (13 mg) in dichloromethane (5 mL) and the combined solution was stirred at room temperature for 16 h. Additional DMAP (13 mg) and triethylamine (255 μL) was added and the reaction mixture was allowed to stir at room temperature for a further 24 h. The reaction solution was concentrated in vacuo and the residue purified by reverse phase C18-column chromatography eluting with buffer A (v/v): water:5% acetonitrile: 0.05% trifluoroacetic acid and buffer B (v/v): acetonitrile: 0.05% trifluoroacetic acid (100:0 v/v to 0:100 v/v). The organic solvent was removed in vacuo and the aqueous solvent was removed by lyophilisation to give compound 10 as a colourless oil (287 mg). $^1$H NMR (400 MHz, CDCl$_3$) $\delta_H$ 7.78 (d, J=8.5 Hz, 4H), 7.32 (d, J=8.5 Hz, 4H), 4.13 (t, J=4.9 Hz, 4H), 3.66 (t, J=4.9 Hz, 4H), 3.62 (br. s, 24H), 3.61-3.58 (m, 8H), 3.56 (s, 8H), 2.42 (s, 6H). m/z $[M+Na]^+$ (877, 100%), $[M+H]^+$ (855, 75%).

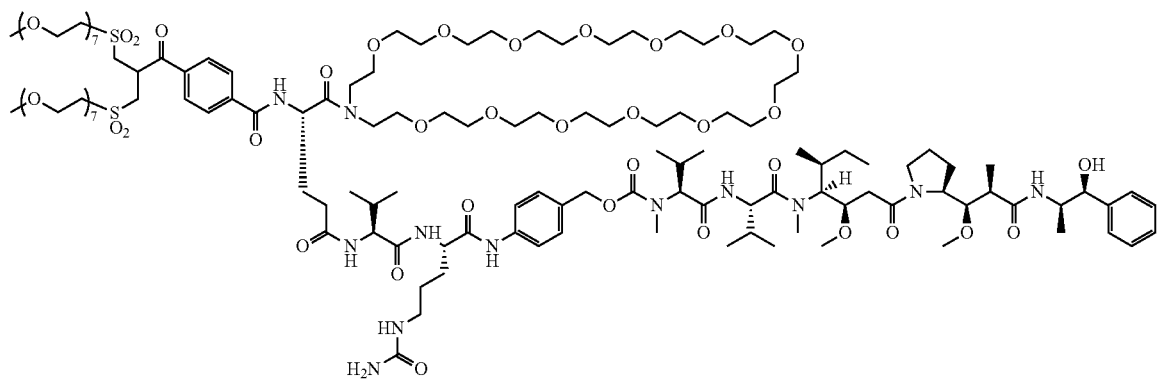

9

Step 1: Synthesis of Compound 10

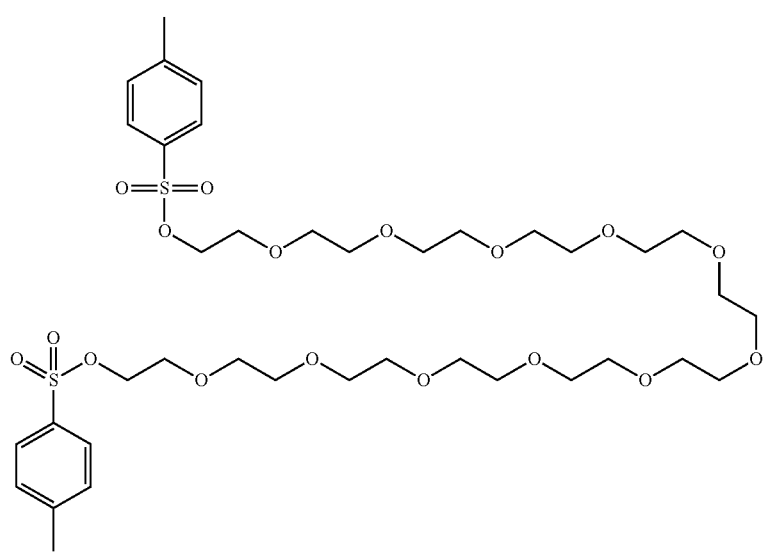

10

Step 2: Synthesis of Compound 11

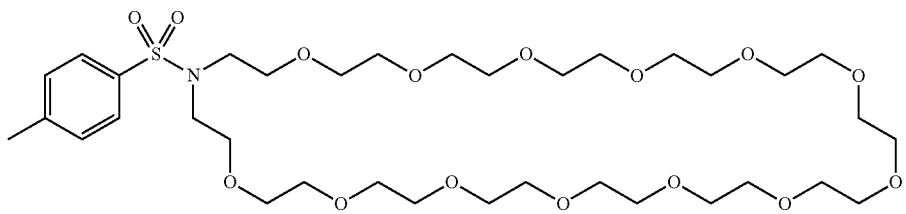

11

A solution of compound 2 (85 mg) in anhydrous THF (2 mL) was added dropwise over a period of 1 h to a solution of sodium hydride (40 mg, 60% dispersion in mineral oil) in anhydrous THF (8 mL) at room temperature. After stirring for 1 h, a solution of compound 10 (280 mg) in anhydrous THF (20 mL) was added over a period of 2 h and the reaction mixture was stirred at room temperature for 96 h. Water (30 mL) was added and the THF was removed in vacuo. The aqueous solution was extracted with chloroform (4×25 mL) and then chloroform:isopropanol (9:1 v/v, 2×25 mL). The organic phases were combined and dried over magnesium sulfate before the solution was filtered and concentrated in vacuo. The residue was then purified by reverse phase C18-column chromatography eluting with buffer A (v/v): water:55% acetonitrile:0.05% trifluoroacetic acid and buffer B (v/v):acetonitrile:0.05% trifluoroacetic acid (100:0 v/v to 0:100 v/v). The organic solvent was removed in vacuo and the aqueous solvent was removed by lyophilisation to give compound 11 as a colourless oil (58 mg). $^1$H NMR (400 MHz, CDCl$_3$) $\delta_H$ 7.68 (d, J=8.4 Hz, 2H), 7.27 (d, J=8.4 Hz, 4H), 3.66-3.52 (m, 52H), 3.35 (t, J=6.3 Hz, 4H), 2.40 (s, 3H). m/z [M+Na]$^+$ (792, 100%), [M+H]$^+$ (770, 55%).

Step 3: Synthesis of Compound 12

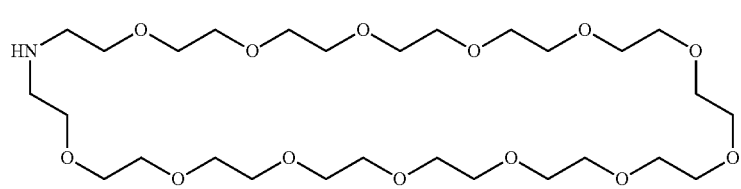

12

To a solution of compound 11 (54 mg) in anhydrous THF (3 mL) was added lithium aluminium hydride (513 μL, 1 M solution in THF) and the solution was heated at reflux for 4 h before the reaction mixture was cooled to 0° C. and quenched by the dropwise addition of water. The suspension was filtered and the precipitate washed with chloroform: ethanol (9:1 v/v, 3×6 mL). The filtrate and washings were combined and concentrated in vacuo to give compound 12 as a white solid (34 mg). m/z [M+Na]$^+$ (639, 10%), [M+H]$^+$ (617, 100%).

Step 4: Synthesis of Compound 13

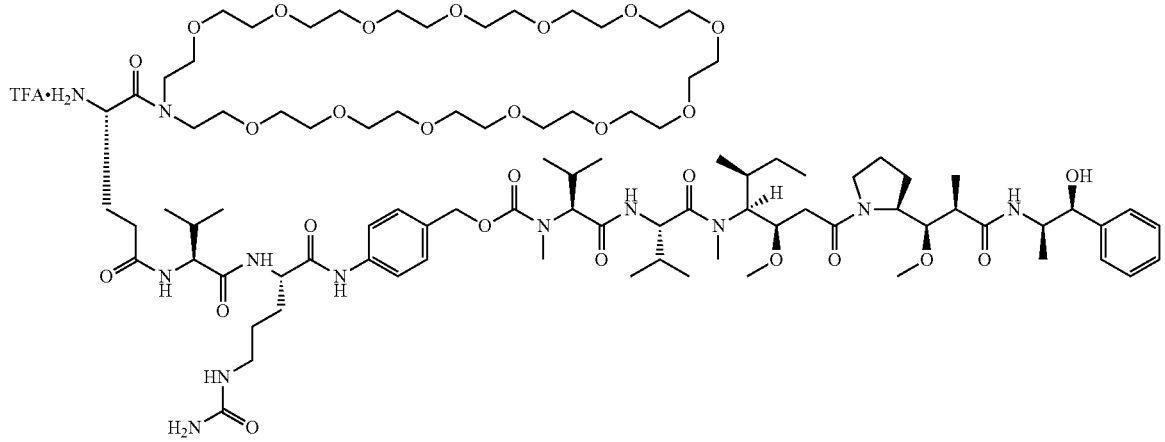

13

To a solution of compound 5 (25 mg) in DMF (0.4 mL) at 0° C. was added HATU (7 mg). The solution was stirred for 20 min at 0° C. before NMM (2 μL) was added and the solution was stirred for a further 10 min. To a separate solution of compound 12 (17 mg) in DMF (0.4 ml) was added NMM (2 μL) and the solution was stirred at room temperature for 30 min. The two solutions were then combined and additional quantities of HATU (7 mg) and NMM (2 μL) were added to the combined solution which was stirred for 1 h at room temperature. Further HATU (7 mg) and NMM (2 μL) were added and the solution stirred for 0.5 h before the reaction solution was concentrated in vacuo to give crude Fmoc-L-Glu-[Val-Cit-PAB-MMAE]-aza-42-crown-14 (35 mg). m/z [M+Na]$^+$ (2095, 25%), [M+H]$^+$ (2073, 15%, [M+2H]$^{2+}$ (1037, 100%). To a solution of crude Fmoc-L-Glu-[Val-Cit-PAB-MMAE]-aza-42-crown-14 (35 mg) in DMF (0.5 mL) was added piperidine (10 μL) and the solution was stirred for 30 min at room temperature. Additional piperidine (10 μL) was added and the solution was stirred for a further 30 min at room temperature. The reaction solution was concentrated in vacuo and the residue purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 13 as a colourless oil (22 mg). m/z [M+Na]$^+$ (1873, 10%), [M+H]$^+$ (1851, 50%), [M+2H]$^{2+}$ (926, 100%).

Step 5: Synthesis of Reagent 9

To a solution of reagent 8 (11.5 mg) in DMF (0.3 mL) at 0° C. was added HATU (3.3 mg) The solution was stirred at 0° C. for 20 min before NMM (0.9 μL) was added and the solution was stirred for a further 10 min. To a separate solution of compound 13 (15 mg) in DMF (0.3 mL) was added NMM (0.9 μL) and the solution was stirred at room temperature for 30 min. The two solutions were then combined and additional quantities of HATU (3.3 mg) and NMM (0.9 μL) were added and the solution was stirred at room temperature for 1 h. Further quantities of HATU (3.3 mg) and NMM (0.9 μL) were added and the solution stirred at room temperature for 1 h. HATU (3.3 mg) and NMM (0.92 μL) were again added and the solution was stirred at room temperature for 2 h before the reaction solution was concentrated in vacuo and the residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 9 as a colourless oil (11 mg). m/z [M+Na]$^+$ (2822, 10%), [M+H]$^+$ (2800, 20%), [M+2H]$^{2+}$ (1400, 80%), [M+3H]$^{3+}$ (933, 100%).

Example 3: Conjugation of Reagents 1 and 17 (Comparative) to Brentuximab and Anti-PSMA Antibodies to Produce Antibody Drug Conjugates (ADCs) 4 and 18 (Comparative) and 21 and 22 (Comparative), Respectively, with DAR 4

Conjugation reagents 1 and 17 were conjugated to Brentuximab or anti-PSMA antibody, giving rise to ADCs 14, 18, 21 and 22 respectively using methods analogous to those described in WO2014064423 and WO2014064424. Briefly, antibody (Brentuximab or anti-PSMA antibody) at a concentration of 5.2 mg/mL in 20 mM sodium phosphate, pH 7.5 (containing 150 mM NaCl and 20 mM EDTA) was heated to 40° C. in a heating block for 15 min. TCEP (6 eq. per mAb) was added to the mAb solution, mixed gently and incubated at 40° C. for 1 h before being allowed to cool to 22° C. Conjugation reagents were dissolved in MeCN or DMF to give a 3 mM solution. The reduced mAb solution was diluted to 4.2 mg/mL with 20 mM sodium phosphate, pH 7.5 (containing 150 mM NaCl and 20 mM EDTA). Conjugation reagent (5.6 eq. per mAb) was added to the mAb solution, the reaction was mixed gently and incubated at 22° C. for 22 h. After this the reaction was treated with 50 mM N-acetyl-L-cysteine (20 eq. over reagent) at 22° C. for 1 h. The crude conjugation mixture was analysed by hydrophobic interaction chromatography (HIC). The crude reaction was mixed with an equal volume of 50 mM sodium phosphate, pH 7 (4 M NaCl) and the resulting solution was loaded onto a ToyoPearl Phenyl-650S HIC column equilibrated with 50 mM sodium phosphate, pH 7 (2 M NaCl). The ADC was eluted from the column with a gradient of 50 mM sodium phosphate, pH 7 (20% isopropanol). Fractions containing DAR 4 ADC were pooled and concentrated (Vivaspin 20, 10 kDa PES membrane). The concentrated sample was buffer exchanged into PBS, pH 7.1-7.5, and sterile filtered (0.22 μm PVDF membranes). DAR assignments were based on A248/A280 absorption ratios. The average DAR of conjugates was calculated from the relative peak areas of individual DAR species following HIC analysis at 280 nm.

Example 4: Synthesis of Conjugation Reagent 15 (Comparative) Comprising the Auristatin Cytotoxic Payload, MMAE Conjugation reagent 5, which contains a maleimide functional grouping, was synthesised as described within WO2015057699.

fied by normal phase column chromatography eluting with dichloromethane:methanol (100:0 v/v to 80:20 v/v). The organic solvent was removed in vacuo to give Fmoc-L-Glu-[OtBu]-[PEG(24u)-OMe] as a colourless oil (84 mg). Piperidine (49 µL) was added to a solution of compound Fmoc-L-Glu-[OtBu]-[PEG(24u)-OMe] (74 mg) in DMF (2 mL) under an argon atmosphere and the resulting solution

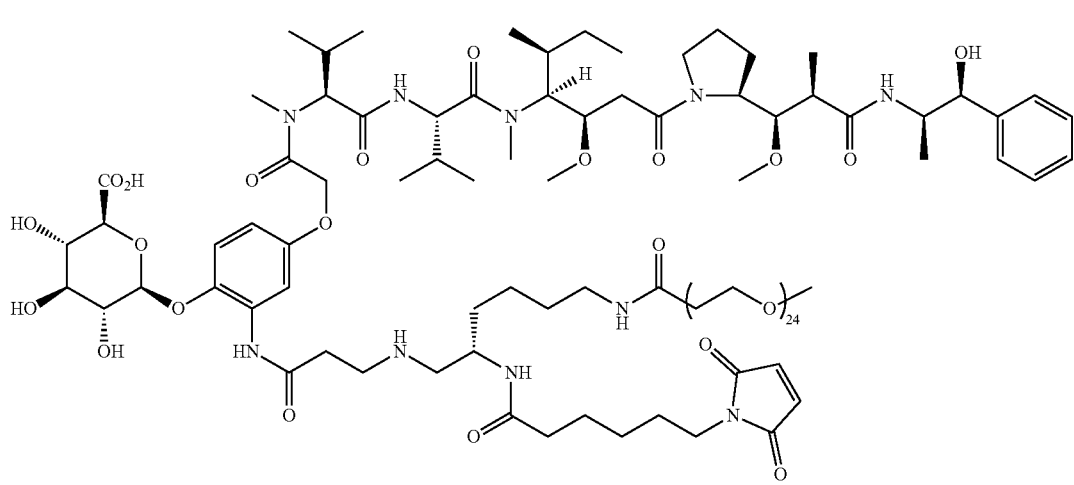

15

Example 5: Synthesis of Conjugation Reagent 17 (Comparative) Comprising the Auristatin Cytotoxic Payload, MMAE stirred at room temperature for 22 h, after which the volatiles were removed in vacuo. The resulting residue was triturated with hexane (3×0.7 mL). The organic solvent was decanted

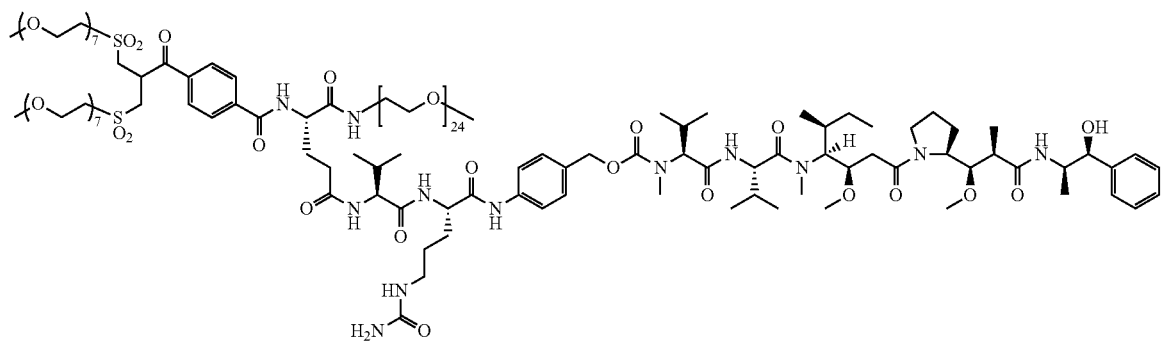

17

Step 1: Synthesis of Compound 19

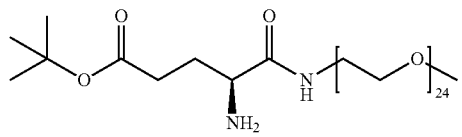

19

A solution of Fmoc-L-Glu-(OtBu)-OH (36 mg) in DMF (2 mL) was cooled to 0° C. under an argon atmosphere and (benzotriazol-1-yloxy)tris-(dimethylamino) phosphonium hexafluorophosphate (BOP) (41 mg) was added, followed by NH$_2$—PEG(24u)-OMe (100 mg) and DIPEA (19 µL). The solution was allowed to warm to room temperature and after 22 h the volatiles were removed in vacuo. The resulting residue was dissolved in dichloromethane (1 mL) and purieach time and the resulting residue dried in vacuo to give compound 19 as a white solid (61 mg). m/z [M+H]$^+$ (1274, 70%), [M+2H]$^{2+}$ (638, 100%).

Step 2: Synthesis of Reagent 20

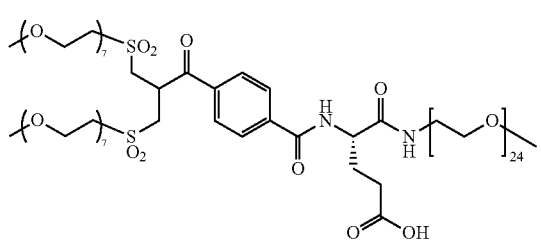

20

To a solution of reagent 8 (26.6 mg) in DMF (550 μL) cooled to 0° C. under an argon atmosphere was added HATU (10.5 mg) and the solution stirred for 0.5 h at 0° C. To this was added a solution of compound 19 (32 mg) in DMF (550 μL). The resulting solution was stirred for 5 min at 0° C. before the addition of NMM (2.9 μL) and HATU (10.5 mg). The reaction solution was allowed to stir at 0° C. for 2 h before being warmed to room temperature and stirred for a further 3.5 h. After this time the volatiles were removed in vacuo. The resulting residue was dissolved in water:acetonitrile (1.2 mL, 1:1 v/v), and purified by reverse phase C18-column chromatography eluting with buffer A (v/v): water:55% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give bis-mPEG(7u) sulfone-propanoyl-benzamide-L-Glu-[OtBu]-[PEG(24u)-OMe] as a colourless oil (30.5 mg). $^1$H NMR (400 MHz, MeOH-$\partial_4$) 8.19 (2H, d), 8.04 (2H, d), 4.83-4.71 (1H, m), 4.58 (1H, dd), 3.92-3.83 (6H, m), 3.78-3.56 (140H, m), 3.57-3.51 (6H, m), 3.40 (4H, dd), 3.36 (3H, s), 3.35 (6H, s), 2.41 (2H, t), 2.24-2.13 (1H, m), 2.10-1.98 (1H, m), 1.45 (9H, s). m/z [M+Na]$^+$ (2243, 50%), [M+H]$^+$ (2221, 40%), [M+Na+2H]$^{3+}$ (747, 100%). A solution of bis-mPEG(7u) sulfone-propanoyl-benzamide-L-Glu-[OtBu]-[PEG(24u)-OMe] (30 mg) in dichloromethane (2 mL) under an argon atmosphere was cooled to 0° C. to which trifluoroacetic acid (500 μL) was added and the resulting solution stirred for 1.5 h. The reaction mixture was allowed to warm to room temperature and stirred for a further 1 h. After this time the volatiles were removed in vacuo. The resulting residue was dissolved in water:acetonitrile (0.6 mL, 1:1 v/v), and purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 20 as a colourless oil (20 mg). $^1$H NMR (400 MHz, MeOH-$\partial_4$) 8.19 (2H, d), 8.04 (2H, d), 4.81-4.72 (1H, m), 4.59 (1H, dd), 3.92-3.84 (6H, m), 3.67-3.50 (146H, m), 3.40 (4H, dd), 3.36 (3H, s), 3.35 (6H, s), 2.48 (2H, t), 2.26-2.15 (1H, m), 2.15-2.03 (1H, m). m/z [M+2H]$^{2+}$ (1083, 60%), [M+2H+Na]$^{3+}$ (729, 100%).

Step 3: Synthesis of Conjugation Reagent 17

A solution of compound 20 (12.4 mg) in DMF (500 μL) was cooled to 0° C. under an argon atmosphere. HATU (2.4 mg) was added and the solution stirred for 0.5 h at 0° C. To this was added a solution of Val-Cit-PAB-MMAE TFA salt (7.8 mg) and NMM (0.7 μL) in DMF (500 μL), which had been stirred at room temperature for 0.5 h. After 5 min, an additional amount of HATU (1.2 mg) and NMM (0.4 μL) was added and the reaction mixture stirred at room temperature. After 2 h, an additional amount of HATU (1.2 mg) and NMM (0.4 μL) was added and the reaction mixture stirred at room temperature. After a further 1 h, the reaction solution was concentrated in vacuo and purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 17 as a colourless oil. m/z [M+H]$^+$ (3270, 12%), [M+2H]$^{2+}$ (1636, 50%), [M+3H]$^{3+}$ (1091, 100%).

Example 6: Conjugation of Reagent 15 (Comparative) to Brentuximab to Produce Antibody Drug Conjugate 16 (Comparative) with DAR 8

Conjugation reagent 1 was conjugated to Brentuximab, giving rise to ADC 16 using the methods described within WO2015057699, U.S. Pat. No. 7,090,843, Lyon et al., (2015) Nature Biotechnology, 33(7) p733-736 and Lyon et al., (2012), Methods in Enzymology, Volume 502, p123-137. Briefly, Brentuximab in 20 mM sodium phosphate buffer, pH 6.5 (150 mM NaCl, 20 mM EDTA) was reduced with TCEP (6 eq.) at 40° C. for 1 h. Conjugation of the reduced antibody with 2.0 molar equivalents of reagent 15 per free thiol was then performed. Reagent 15 was added to the mAb to give a final antibody concentration of 4 mg/mL. The solution was mixed gently and incubated at 22° C. for 2 h. After 2 h additional reagent 15 (0.2 molar equivalents) was added and the mixture was incubated for a further 1 h at 22° C. Excess reagent 15 was quenched with N-acetyl-L-cysteine (20 eq. over reagent) and the crude reaction was purified using a 1 mL ToyoPearl Phenyl-650S HIC column equilibrated with 50 mM sodium phosphate, pH 7 (2 M NaCl). The ADC was eluted from the column with a gradient of 50 mM sodium phosphate, pH 7 (20% isopropanol). Fractions containing ADC were pooled and concentrated (Vivaspin20, 10 kDa PES membrane) to give an average DAR 8 product. The concentrated sample was buffer exchanged into DPBS, pH 7.1-7.5 and sterile filtered.

ADC 16 was difficult to purify and characterise due to the heterogeneity of the reaction products (number of DAR variants), leading to poor resolution of the individual DAR species by preparative HIC. Results showed that the final reaction product contained significant quantities of DAR species both greater than and less than DAR 8. Purifying the DAR8 species completely from these higher and lower than DAR8 species would result in significantly lower yields of DAR8 in the final product.

Example 7: Comparison of Antibody Drug Conjugates 14 and 16 (Comparative) by Thermal Stress Test ADC samples 14 and 16 were each prepared at 0.5 mg/mL by dilution with DPBS pH 7.1-7.5.

The two ADC samples were incubated at 65° C. for 30 min followed by incubation in an ice bath for 5 min before Size Exclusion Chromatography (SEC). SEC was performed using a TOSOH Bioscience TSK gel Super SW 3000 column. UV absorbance at 280 nm was monitored during an isocratic elution with a 0.2 M potassium phosphate buffer, pH 6.8 (0.2 M potassium chloride and 15% isopropanol).

Tables 1a and 1b below show the conformations of ADCs 14 and 16 before and after thermal stress test, as measured by the area under the curve of each peak by Abs 280 nm, following SEC.

The results in Tables 1a and 1b show that ADC 14 remains in a non-aggregated state to a much greater extent than ADC 16 following thermal stress test. In addition, the results also show that 16 dissociates into lighter molecular weight components to a greater extent than conjugate 14.

TABLE 1a

| ADC conformation before thermal stress test (% of total ADC) | 14 | 16 |
| --- | --- | --- |
| Non-aggregated | 98.1 | 97.4 |
| Aggregated | 1.9 | 1.8 |
| Dissociated | 0 | 0.7 |

TABLE 1b

| ADC conformation after thermal stress test (% of total ADC) | 14 | 16 |
| --- | --- | --- |
| Non-aggregated | 62.0 | 11.1 |
| Aggregated | 37.4 | 71 |
| Dissociated | 0.6 | 17.9 |

Example 8: Comparison of Average DARs for ADCs 14 and 16 (Comparative) Following Incubation within Human Serum ADCs 14 and 16 were diluted to 0.1 mg/mL in human serum, 88% (v/v) serum content. Each solution was immediately sub-aliquoted into 4×0.5 mL low-bind Eppendorf tubes. Two of the Eppendorf tubes, corresponding to the '0' time points were immediately transferred to the −80° C. freezer, while the remaining samples were incubated at 37° C. for 6 d. After 6 d, the samples were removed from the freezer and/or the incubator, the conjugates purified by affinity capture (CD30-coated magnetic beads), and analysed using hydrophobic interaction chromatography (HIC). CD30 affinity capture and HIC for average DAR determination were carried out as described:

CD30 affinity capture for average DAR determination. Affinity capture was performed using streptavidin coated magnetic beads (Dynabeads-Streptavidin T1, Life Technologies). CD30 (Recombinant human CD30, Sino Biological Inc.) was biotinylated and immobilized on beads through streptavidin-biotin binding and finally blocked using skimmed milk peptides. 500 µL of the plasma sample in PBS was added to the CD30-coated beads and incubated overnight at 4° C. and finally washed using PBS. Captured antibodies were eluted using acidic elution buffer for 5 min at 4° C. The eluate was subsequently neutralized to pH 7 using sodium acetate buffer, pH 8. Eluted samples were further mixed with HIC loading buffer and analysed using hydrophobic interaction chromatography with UV detection (HIC-UV).

Hydrophobic interaction chromatography for average DAR determination. Affinity captured ADCs were analysed using hydrophobic interaction chromatography in order to determine the average drug to antibody ratio (DAR). The method consisted of a linear gradient from 100% buffer A (50 mM sodium phosphate pH 7.0, 1.5 M ammonium sulfate) to 100% buffer B (50 mM sodium phosphate pH 7.0, 20% isopropanol) in 30 min using a TOSOH TSK gel Butyl-NPR HIC separation column with detection at 280 nm.

FIG. 1 shows that after 6 days at 37° C. in human serum, conjugate 16 has lost much of its cytotoxic payload, whereas conjugate 14 remains largely unchanged, as indicated by the reduction in average DAR value of the sample. This indicates that conjugates of the invention have improved stability.

Example 9: Analysis of DAR4 ADCs 14 and 18 (Comparative) and 21 and 22 (Comparative), by In Vitro Cell Viability Assay Loss of tumour cell viability following treatment with cytotoxic drugs in vitro can be measured by growing cell lines in the presence of increasing concentrations of drug and quantifying the loss of proliferation or metabolic activity using Cell-Titer Glo® Luminescent reagent (Promega). The protocol for PSMA and CD30 overexpressing cell lines describes cell seeding, drug treatment and determination of the cell viability in reference to untreated cells based on ATP synthesis, which is directly correlated to the number of cells present in the well.

The cell lines listed in Table 2 were maintained following the suppliers' recommendations.

TABLE 2

| Cell line | Antigen | Source | Growth medium |
| --- | --- | --- | --- |
| LNCaP clone FGC | PSMA | ECACC, Cat. 89110211 | RPMI-1640 medium (Life Technologies ®), 10% fetal bovine serum, 100 U/mL Penicillin and 100 ug/mL Streptomycin |
| C4-2 | PSMA | | |
| Karpas-299 | CD30 | Dr Abraham Karpas at the University of Cambridge | |

Adherent PSMA-positive LNCaP and C4-2 cells were detached with TrypLE and resuspended in complete medium. Cells were counted using disposable Neubauer counting chambers and cell density adjusted to $10 \times 10^4$ cells/mL for LNCaP and $2 \times 10^4$ cells/mL for C4-2, respectively. The cells were seeded (100 µL/well) into poly-D-Lysine coated opaque-walled 96-well white plates and incubated for 24 h at 37° C. and 5% $CO_2$.

Human T cell lymphoma Karpas 299 cells were counted and adjusted to a cell density of $5 \times 10^4$ cells/mL in complete growth medium. Cells were seeded (50 µL/well) into opaque-walled 96-well plates and incubated for 24 h at 37° C. and 5% $CO_2$.

Eight point serial dilutions of each compound were prepared in the relevant culture medium. Cells were treated with the compounds and concentration ranges are specified in Table 3.

TABLE 3

| Cell line | Drug-conjugate | Concentration range |
|---|---|---|
| Karpas 299 | 14 | 1 nM-0.06 pM |
| Karpas 299 | 18 (comparative) | 0.5 nM-0.2 pM |
| LNCaP & C4-2 | 21 | 10 nM-5 pM |
| LNCaP & C4-2 | 22 (comparative) | 10 nM-5 pM |
| LNCaP & C4-2 | MMAE (free drug) | 10 nM-5 pM |

The medium from the plate containing the adherent LNCaP or C4-2 cells was removed and replaced by 100 µL/well of the 1× serially diluted compounds. Karpas-299 cells were treated by addition of 50 µL/well of the 2× serially diluted compounds. The cells were then incubated at 37° C. and 5% $CO_2$ for a further 96 h.

The cell viability assay was carried out using the Cell-Titer Glo® Luminescence reagent, as described by the manufacturer's instructions, (Promega Corp. Technical Bulletin TB288; Lewis Phillips G. D, Cancer Res 2008; 68:9280-9290).

Luminescence was recorded using a Molecular Devices Spectramax i3x plate reader and data subsequently analysed using GraphPad Prism four parameter non-linear regression model. Viability was expressed as % of untreated cells and calculated using the following formula:

$$\% \text{ Viability} = 100 \times \frac{Luminescence_{Sample} - Luminescence_{No\ cell\ Control}}{Luminescence_{Untreated} - Luminescence_{No\ cell\ Control}}$$

The % viability was plotted against the logarithm of drug concentration in nM to extrapolate the $IC_{50}$ values. $IC_{50}$ values indicating the anti-proliferative effects of the drug conjugates are summarised in Table 4. These indicate that conjugates of the invention have improved potency.

TABLE 4

| Cell line | Drug-conjugate | $IC_{50}$ (nM) |
|---|---|---|
| Karpas 299 | 14 | 0.04 |
| Karpas 299 | 18 (comparative) | 0.06 |
| LNCaP | 21 | 0.61 |
| LNCaP | 22 (comparative) | 0.76 |
| LNCaP | MMAE (free drug) | 2.14 |
| C4-2 | 21 | 0.19 |
| C4-2 | 22 (comparative) | 0.27 |
| C4-2 | MMAE (free drug) | 0.71 |

Example 10: Synthesis of Conjugation Reagent 23 (Comparative) Comprising the Auristatin Cytotoxic Payload, MMAE

23

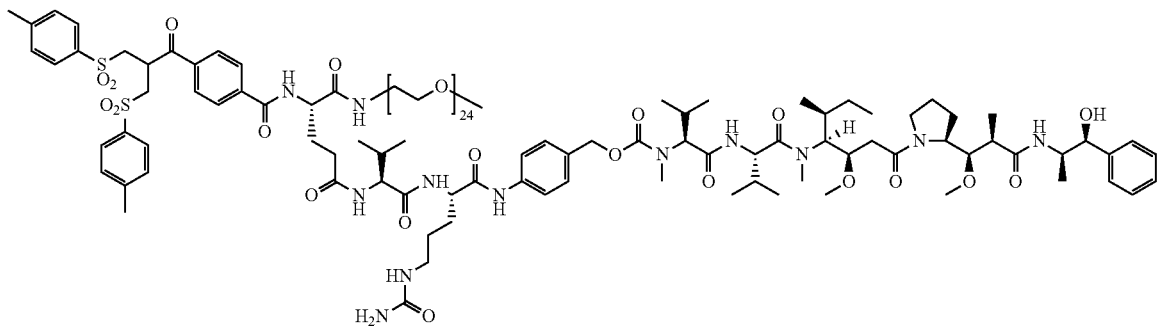

Step 1: Synthesis of Reagent 24

24

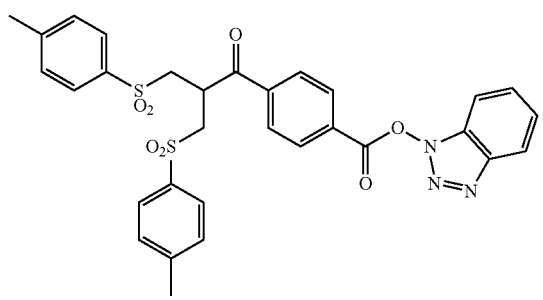

A solution of 4-[2,2-bis[(p-tolylsulfonyl)-methyl]acetyl] benzoic acid (1.0 g) was added to N-hydroxybenzotriazole hydrate (306 mg) in anhydrous THF (10 mL) under a nitrogen atmosphere. The resulting solution was cooled to 0° C. and diisopropylcarbodiimide (310 µL) was added dropwise. The reaction mixture was stirred for 20 min at 0° C. before being warmed to room temperature. Additional anhydrous THF (10 mL) was added to the reaction mixture after 1 h. After 18 h, the formed precipitate was filtered and washed with cold THF (2×5 mL) before being dried in vacuo. The solid was stirred with MeOH (10 mL) for 1 h at room temperature, collected by filtration and washed sequentially with MeOH (2×5 mL) and $Et_2O$ (5 mL). The solid was then dried in vacuo to give compound 24 as a white solid (1.1 g). m/z [M+H]⁺ (618, 100%).

Step 2: Synthesis of Reagent 25

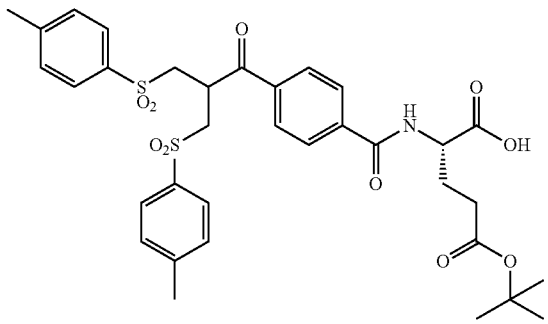

To a stirred suspension of L-Glutamic acid 5-tert-butyl ester (198 mg) in anhydrous DMF (20 mL) under a nitrogen atmosphere was added NMM (107 µL). The reaction mixture was cooled to 0° C. before reagent 24 (603 mg) was added. The resulting suspension was stirred at 0° C. for 1 h, after which the reaction mixture was allowed to warm to room temperature. After 19 h, the resulting solution was concentrated in vacuo and purified by reverse phase C18-column chromatography, eluting with buffer A (v/v): water: 5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give the reagent 25 as a white solid (198 mg). ¹H NMR (400 MHz, CDCl₃) δ 7.98 (1H, d), 7.86 (2H), 7.71-7.65 (6H, m), 7.36 (4H, d), 4.68 (1H, ddd), 4.34 (1H, q), 3.62 (2H, ddd), 3.50 (2H, ddd), 2.69 (1H ddd), 2.55-2.45 (1H, m), 2.48 (6H, s), 2.34-2.16 (2H, m), 1.46 (9H, s); m/z [2M+H]⁺ (1371,74%), [2M+H-tBu]⁺ (1315, 70%), [M+H-tBu]⁺ (630, 100%).

Step 3: Synthesis of Reagent 26

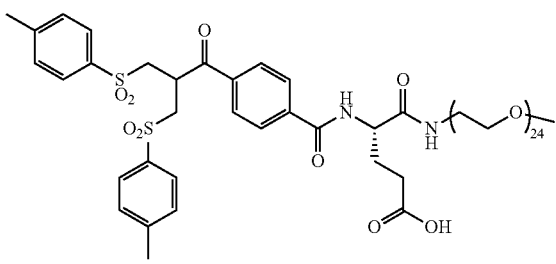

Reagent 25 (50 mg) and BOP (40 mg) were dissolved in anhydrous DMF (3 mL), cooled to 0° C. and added to a solution of NH₂—PEG(24u)-OMe (99 mg) and NMM (10 µL) in anhydrous DMF (2 mL). The reaction mixture was stirred at 0° C. and after 4 h, additional amounts of BOP (10 mg) and NMM (2.5 µL) were added to the reaction mixture which was stirred for a further 15 min before being stored at −20° C. for 18 h. The reaction mixture was then concentrated in vacuo and purified by reverse phase C18-column chromatography, eluting with buffer A (v/v): water:5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give bis-tolylsulfonyl-propanoyl-benzamide-L-Glu-[OtBu]-[PEG(24u)-OMe] as a colourless oil (128 mg). m/z [M+H]⁺ (1757, 100%), [M+2H]²⁺ (879, 100%). Bis-tolylsulfonyl-propanoyl-benzamide-L-Glu-[OtBu]-[PEG(24u)-OMe] (126.5 mg) was dissolved in formic acid (2.5 mL) and stirred under a nitrogen atmosphere at room temperature. After 20 h, the reaction mixture was concentrated in vacuo and dried under high vacuum for 18 h to give reagent 26 as a colourless oil (122 mg, assumed quantitative yield). m/z [M+Na]⁺ (1723, 15%), [M+H]⁺ (1700, 100%).

Step 4: Synthesis of Reagent 23

A solution of reagent 26 (13 mg), HATU (4.1 mg) and Val-Cit-PAB-MMAE.TFA salt (9 mg) in anhydrous DMF (1 mL) under an argon atmosphere was cooled to 0° C. To this was added NMM (2 µL). After 1 h, an additional amount of HATU (4.1 mg) and NMM (2 µL) was added, and after a further 1.5 h the solution was stored at −20° C. for 72 h. The reaction solution was concentrated in vacuo, dissolved in acetonitrile (1 ml) and purified by reverse phase C18-column chromatography eluting with buffer A (v/v): water: 5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 23 as a thick clear colourless oil (11.4 mg). m/z [M+H]⁺ (2805, 20%), [M+2H]²⁺ (1403, 75%), [M+3H]³⁺ (936, 100%).

Example 11: Synthesis of Conjugation Reagent 27 (Comparative) Comprising the Auristatin Cytotoxic Payload, MMAE

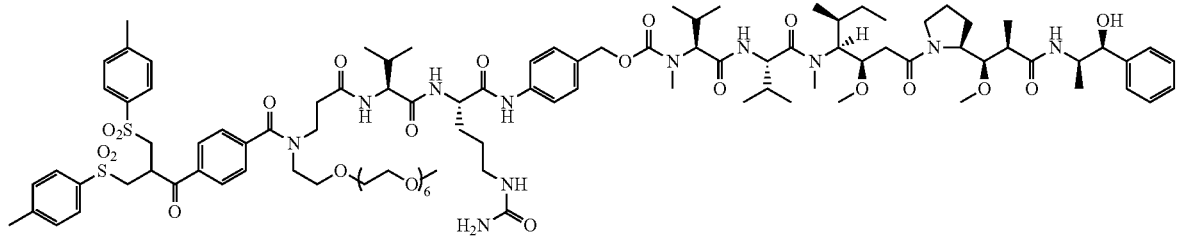

Step 1: Synthesis of Compound 28

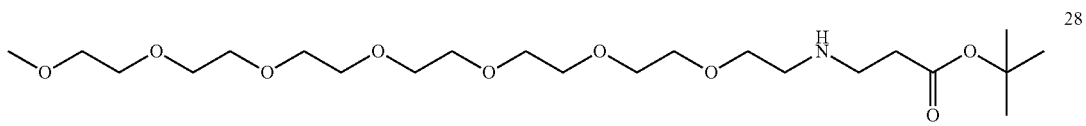 [SMILES: COCCOCCOCCOCCOCCOCCOCCNCCC(=O)OC(C)(C)C]

To a solution of NH$_2$—PEG(7u)-OMe (300 mg) in ethanol (2.5 mL) was added tert-butyl acrylate (194 μL) and the reaction mixture was stirred at room temperature for 72 h. The solution was concentrated in vacuo and purified by normal phase chromatography eluting with dichloromethane:methanol (100:0 v/v to 70:30 v/v). The solvent was removed in vacuo to give compound 28 as a pale yellow oil (324 mg). m/z [M+H]$^+$ (468, 100%).

Step 2: Synthesis of reagent 29

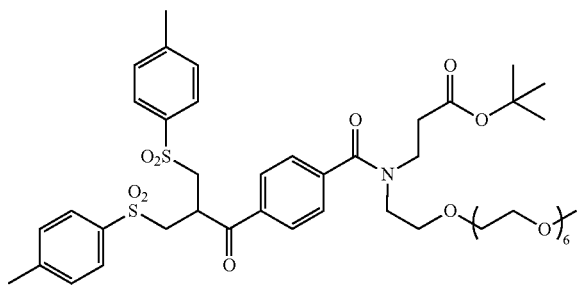

To a solution of 4-[2,2-bis[(p-tolylsulfonyl)-methyl]acetyl]benzoic acid (257 mg) in anhydrous DMF (2.5 mL) at 0° C. was added HATU (204 mg) and the reaction mixture was stirred at 0° C. for 10 min. NMM (57 μL) was added and the reaction solution was stirred for a further 20 min at 0° C. Additional HATU (102 mg) and NMM (29 μL) were added and the solution was warmed to room temperature and left to stir for 30 min. After this time, a solution of compound 28 (200 mg) in anhydrous DMF (2.5 mL) was added. The reaction mixture was stirred for 5 h. The solution was then concentrated in vacuo and purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 2 as a colourless solid (173 mg). m/z [M+Na]$^+$ (973, 40%) [M+H]$^+$ (951, 100%), [M+H–tBu]$^+$ (895, 90%).

Step 3: Synthesis of Reagent 30

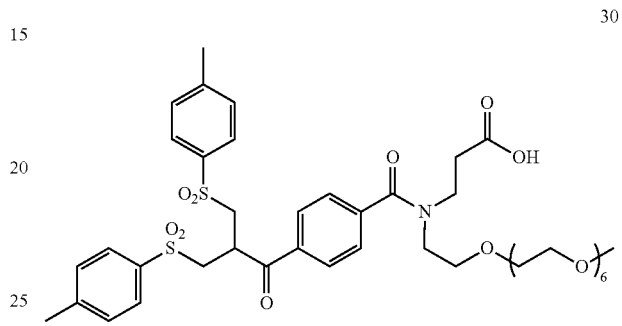

To a solution of reagent 29 (160 mg) in dichloromethane (1.6 mL) at 0° C. was added trifluoroacetic acid (0.5 mL) and the solution was stirred at 0° C. for 1 h and then stored at 4° C. for 16 h. The volatiles were then removed in vacuo, the residue was dissolved in acetonitrile (1 mL) and diluted with aqueous buffer (v/v): water:5% acetonitrile:0.05% trifluoroacetic acid (5 mL). The solvent was then removed by lyophilisation to give reagent 30 as an amber oil (quantitative yield). m/z [M+Na]$^+$ (916, 50%), [M+H]$^+$ (894, 100%).

Step 4: Synthesis of Reagent 27

To a solution of reagent 30 (15 mg) in anhydrous DMF (0.6 mL) at 0° C. was added HATU (7.3 mg) and the reaction mixture was stirred at 0° C. for 20 min. NMM (2 μL) was added and the solution was stirred for a further 20 min at 0° C. Additional HATU (7.3 mg) and NMM (2 μL) were then added, the solution was warmed to room temperature and stirred for 30 min. A separate solution of Val-Cit-PAB-MMAE.TFA salt (21.8 mg) and NMM (2 μL) in anhydrous DMF (0.6 mL) which had previously been stirred at room temperature for 10 min, was then added to the reaction solution. After stirring at room temperature for 3 h, the reaction solution was concentrated in vacuo and purified by reverse phase C18-column chromatography eluting with buffer A (v/v): water:55% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 2 as a white solid (23.7 mg). m/z [M+H]$^+$ (2000, 10%), [M+2H]$^{2+}$ (1000, 100%).

Example 12: Conjugation of Reagents 9 and 27 (Comparative) to Brentuximab to Produce Antibody Drug Conjugates (ADCs) 31 and 32 (Comparative) Respectively, with DAR 4

Conjugation reagents 9 and 27 (comparative) were conjugated to Brentuximab giving rise to ADCs 31 and 32 (comparative) respectively, using a method analogous to that described in Example 3. Briefly, Brentuximab (5.0 mg/mL in 20 mM sodium phosphate, 150 mM NaCl, 20 mM EDTA, pH 7.5) was heated to 40° C. in a heating block for 15 min. TCEP (6 eq. per mAb) was added to the mAb solution, mixed gently and incubated at 40° C. for 1 h before being allowed to cool to 22° C. Conjugation reagent 9 was dissolved in acetonitrile and conjugation reagent 2 was dissolved in DMF to give 3 mM and 1.6 mM stock solutions respectively. The reduced mAb solutions were diluted to approximately 4.3 mg/mL with 20 mM sodium phosphate, 150 mM NaCl, 20 mM EDTA, pH 7.5. Conjugation reagents (5.6 to 6.0 eq. per mAb) were added to the reduced mAb solutions to give a final antibody concentration of 4 mg/mL. The reaction solutions were mixed gently and incubated at 22° C. for 16 to 24 h. After this time, each reaction solution was treated with 50 mM N-acetyl-L-cysteine (20 eq. over reagent) at 22° C. for 1 h. Each crude conjugation mixture was analysed by hydrophobic interaction chromatography (HIC). The crude reactions were mixed with an equal volume of 50 mM sodium phosphate, 4 M NaCl, pH 7 and the resulting solutions loaded onto a ToyoPearl Phenyl-650S HIC column equilibrated with 50 mM sodium phosphate, 2 M NaCl, pH 7. The ADCs were eluted from the column with a gradient of 50 mM sodium phosphate, pH 7 (20% isopropanol). Fractions containing DAR 4 ADC were pooled and concentrated (Vivaspin 20, 10 kDa PES membrane). The concentrated samples were buffer exchanged into PBS, pH 7.1-7.5, and sterile filtered (0.22 μm PVDF membranes).

Example 13: Synthesis of Conjugation Reagent 33 Comprising a Duocarmycin Cytotoxic Payload

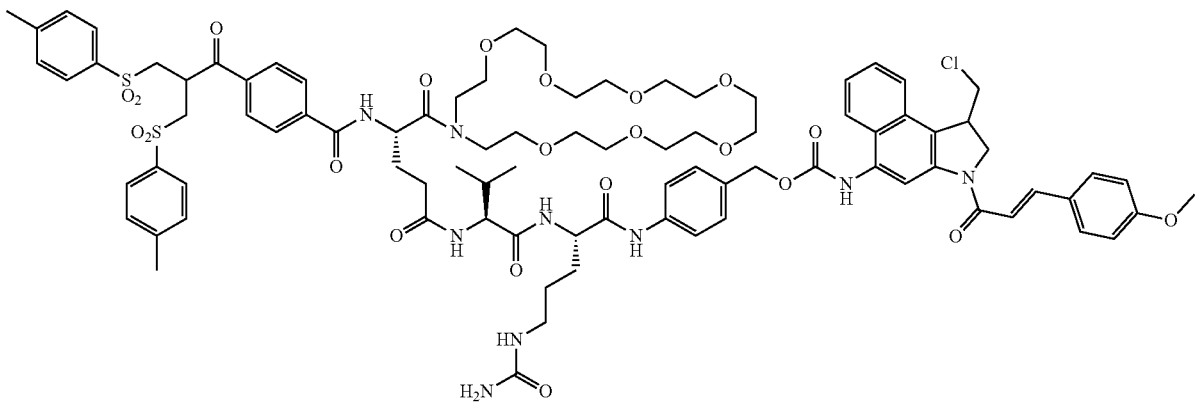

33

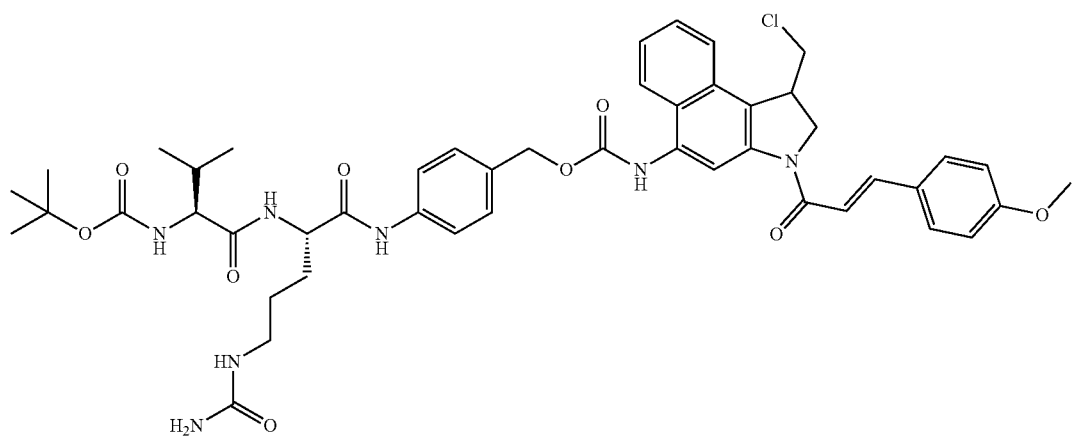

Boc-Val-Cit-PAB-Duocarmycin

Step 1: Synthesis of Compound 34

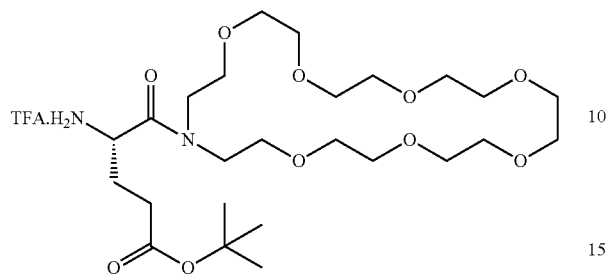

To a solution of Fmoc-Glu(OtBu)-OH (78 mg) in anhydrous DMF (500 μL) at 0° C. was added HATU (108 mg) and NMM (34 μL) and the mixture was stirred at 0° C. for 10 min. To this was added a solution of compound 4 (44 mg) in anhydrous DMF (500 μL) and the mixture was stirred at 0° C. under an argon atmosphere for 15 min. The reaction mixture was then concentrated in vacuo and the residue dissolved in anhydrous DMF (500 μL). Piperidine (70 μL) was added and the solution stirred for 90 min at room temperature. The reaction solution was concentrated in vacuo and purified by reverse phase C18-column chromatography, eluting with buffer A (v/v): water:5% acetonitrile: 0.05% trifluoroacetic acid and buffer B (v/v): acetonitrile: 0.05% trifluoroacetic acid (100:0 v/v to 0:100 v/v). The organic solvent was removed in vacuo and the aqueous solvent removed by lyophilisation to give compound 34 as an orange oil (44 mg). m/z [M+H]$^+$ (537, 45%).

Step 2: Synthesis of Reagent 35

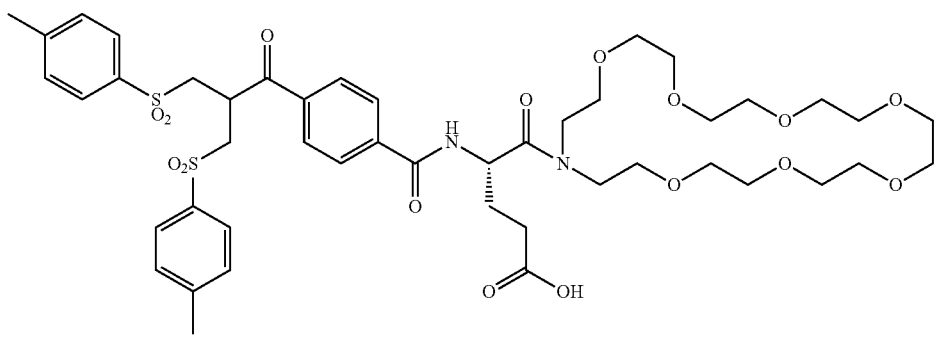

To a solution of 4-[2,2-bis[(p-tolylsulfonyl)-methyl] acetyl]benzoic acid (37.5 mg) in anhydrous DMF (500 μL) at 0° C. was added HATU (65 mg) and NMM (20 μL) and the mixture was stirred at 0° C. for 10 min. To this was added a solution of compound 34 (44.3 mg) in anhydrous DMF (500 μL) and the mixture was stirred at 0° C. under an argon atmosphere for 1 h. The reaction mixture was then concentrated in vacuo, the residue dissolved in DMF (1 mL) and purified by reverse phase C18-column chromatography, eluting with buffer A (v/v): water:0.05% trifluoroacetic acid and buffer B (v/v): acetonitrile:0.05% trifluoroacetic acid (60:40 v/v to 0:100 v/v). The solvent was removed by lyophilisation to give bis-tolylsulfonyl-propanoyl-benzamide-L-Glu-(OtBu)-aza-24-crown-8 as a white solid (28.5 mg). m/z [M+Na]$^+$ (1041, 20%), [M+H]$^+$ (1019, 5%). To a solution of bis-tolylsulfonyl-propanoyl-benzamide-L-Glu-(OtBu)-aza-24-crown-8 (26.5 mg) in anhydrous dichloromethane (1 mL) was added trifluoroacetic acid (500 μL) and the solution stirred at room temperature under an argon atmosphere for 1 h. The volatiles were removed in vacuo to give reagent 35 as a white solid (assumed quantitative yield). m/z [M+Na]$^+$ (985, 35%), [M+H]$^+$ (963, 30%).

Step 3: Synthesis of Compound 3

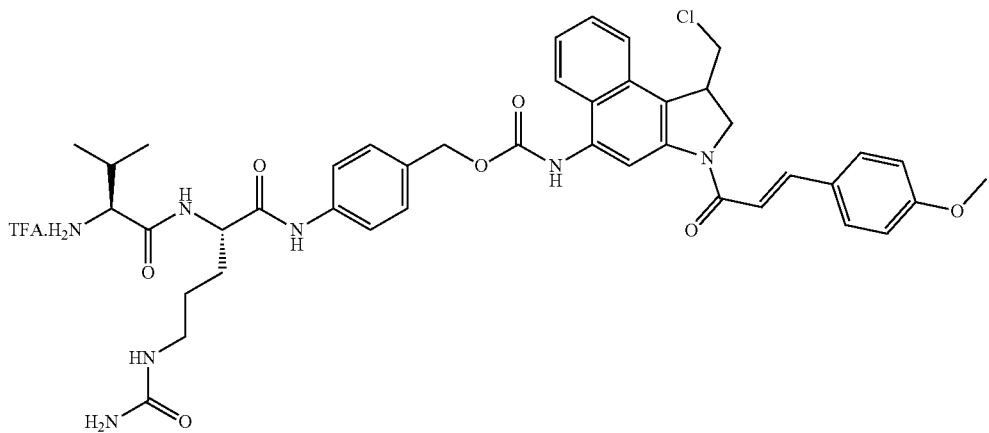

36

To a suspension of Boc-Val-Cit-PAB-Duocarmycin (Abzena, TCRS, 17 mg) in anhydrous dichloromethane (2 mL) at 0° C. was added trifluoroacetic acid (1 mL) and the resulting solution stirred at 0° C. for 75 min. The volatiles were then removed in vacuo to give compound 36 as a yellow solid (assumed quantitative yield). m/z [M+H]$^+$ (798, 100%).

Step 3: Synthesis of Reagent 33

To a solution of reagent 35 (13.4 mg) in anhydrous DMF (500 μL) at 0° C. was added HATU (13.2 mg) and NMM (4 μL) and the mixture stirred at 0° C. for 10 min. To this was added a solution of compound 36 (12.7 mg) in anhydrous DMF (500 μL) and the mixture was stirred at 0° C. under an argon atmosphere for 20 min. Additional quantities of HATU (7.9 mg) and NMM (2.6 μL) were added and the reaction mixture stirred for a further 80 min. The solution was then concentrated in vacuo and purified by reverse phase C18-column chromatography, eluting with buffer A (v/v): water:55% acetonitrile:0.05% trifluoroacetic acid and buffer B (v/v): acetonitrile:0.05% trifluoroacetic acid (100:0 v/v to 0:100 v/v). The solvent was removed by lyophilisation to give reagent 33 as a yellow solid (5.1 mg). m/z [M+Na]$^+$ (1766, 60%), [M+H]$^+$ (1744, 70%), [M+Na+H]$^{2+}$ (884, 90%), [M+2H]$^{2+}$ (872, 100%).

Example 14: Synthesis of Conjugation Reagent 37 (Comparative) Comprising a Duocarmycin Cytotoxic Payload

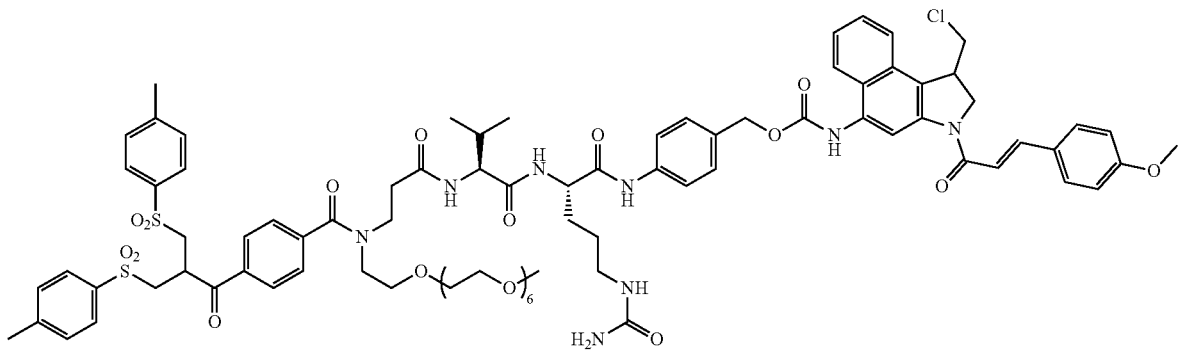

37

To a solution of reagent 30 (14.1 mg) in anhydrous DMF (500 µL) at 0° C. was added HATU (24 mg) and NMM (7.6 µL) and the mixture stirred at 0° C. for 5 min. To this was added a solution of compound 36 (14.4 mg) in anhydrous DMF (500 µL) and the mixture stirred at 0° C. under an argon atmosphere for 40 min. The solution was then concentrated in vacuo, the residue dissolved in water:acetonitrile (3:7 v/v, 1 mL) and purified by reverse phase C18-column chromatography eluting with buffer A (v/v): water: 55% acetonitrile:0.05% trifluoroacetic acid and buffer B (v/v): acetonitrile:0.05% trifluoroacetic acid (100:0 v/v to 0:100 v/v). The solvent was removed by lyophilisation to give reagent 37 as a yellow solid (8.9 mg). m/z [M+Na]$^+$ (1696, 10%), [M+H]$^+$ (1675, 50%), [M+Na+H]$^{2+}$ (848, 40%), [M+2H]$^{2+}$ (838, 85%).

Example 15: Conjugation of Reagents 33 and 37 (Comparative) to Brentuximab to Produce Antibody Drug Conjugates (ADCs) 38 and 39 (Comparative) Respectively, with DAR 4

Conjugation reagents 3 and 37 (comparative) were conjugated to Brentuximab, giving rise to ADCs 38 and 39 (comparative) respectively, using a method analogous to that described in Example 3. Briefly, Brentuximab (8.5 mg/mL in 20 mM sodium phosphate, 150 mM NaCl, 20 mM EDTA, pH 7.5) was heated to 40° C. in a heating block for 15 min. TCEP (6 eq. per mAb) was added to the mAb solution, mixed gently and incubated at 40° C. for 1 h before being allowed to cool to 22° C. Conjugation reagents were dissolved in propylene glycol to give 0.3 mM solutions. Conjugation reagents (5.6 eq. per mAb) were then added to the mAb solutions and the reactions mixed gently and incubated at 22° C. for 42 to 78 h, during which time additional reagents (up to 1.2 eq. per mAb) were added to the reactions as required. The crude reaction solutions were then mixed with an equal volume of 50 mM sodium phosphate, 4 M NaCl, pH 7, and 5 times the volume of the crude reaction mixture of 50 mM sodium phosphate, 2 M NaCl, pH 7. The resulting solutions were loaded onto a ToyoPearl Phenyl-650S HIC column equilibrated with 50 mM sodium phosphate, 2 M NaCl, pH 7. The ADCs were eluted from the column with a gradient of 50 mM sodium phosphate, pH 7 (20% isopropanol). Fractions containing DAR 4 ADC were pooled and concentrated (Vivaspin 20, 30 kDa PES membrane), prior to being buffer exchanged into PBS, pH 7.1- 7.5, and sterile filtered (0.22 µm PVDF membranes). The samples were further purified using a Superdex 200 pg SEC column by isocratic elution with PBS, pH 7.1-7.5 (10 or 20% isopropanol). Fractions containing DAR 4 ADC were pooled and concentrated (Vivaspin 20, 30 kDa PES membrane) prior to being buffer exchanged into PBS, pH 7.1-7.5, and sterile filtered (0.22 µm PVDF membranes).

Example 16: Synthesis of Conjugation Reagent 40 Comprising the Auristatin Cytotoxic Payload, MMAE

40

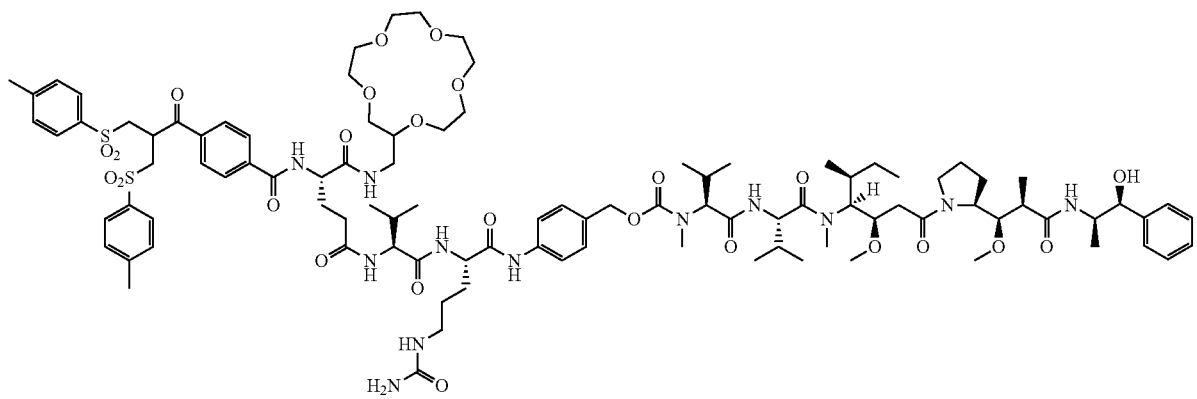

Step 1: Synthesis of Compound 4

41

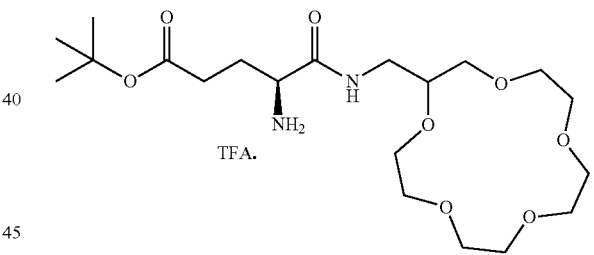

To a solution of Fmoc-Glu(OtBu)-OH (469 mg) in anhydrous DMF (8 mL) at 0° C. was added HATU (419 mg) and the mixture was stirred at 0° C. for 20 min. NMM (121 µL) was then added and the solution stirred at 0° C. for a further 15 min. To a separate solution of 2-aminomethyl-15-crown-5 (250 mg) in anhydrous DMF (2 mL) was added NMM (121 µL) and the solution stirred at 0° C. for 20 min. The two solutions were then combined, additional quantities of HATU (419 mg) and NMM (121 µL) were added and the mixture stirred at room temperature for 3 h. The reaction solution was then concentrated in vacuo and purified by reverse phase C18-column chromatography, eluting with buffer A (v/v): water:0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give Fmoc-L-Glu(OtBu)-amidomethyl-15-crown-5 as a white solid (440 mg). m/z [M+Na]$^+$ (679, 25%), [M+H]$^+$ (657, 30%), [M+H−tBu]$^+$ (601, 100%). To a solution of Fmoc-L-Glu(OtBu)-amidomethyl-15-crown-5 (440 mg) in dichloromethane (20 mL) was added piperidine (463 μL) and the solution stirred at room temperature for 3.5 h. Additional piperidine (198 μL) was added and the mixture stirred at room temperature for a further 1.5 h. The reaction mixture was then concentrated in vacuo and the residue suspended in acetonitrile (4 mL). The acetonitrile mixture was extracted with hexane (50 mL) before the acetonitrile layer was reduced in vacuo to give an oily residue. The residue was then purified by reverse phase C18-column chromatography, eluting with buffer A (v/v): water:0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give reagent 41. m/z [M+Na]$^+$ (457, 10%), [M+H]$^+$ (435, 100%), [M+H−tBu]$^+$ (379, 30%).

Step 2: Synthesis of Reagent 42

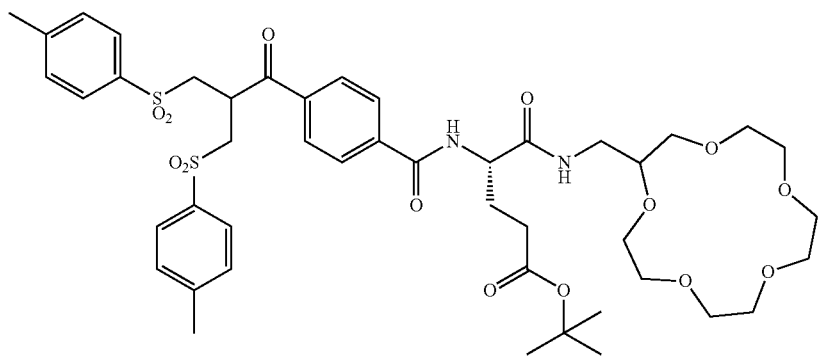

To a solution of compound 24 (82 mg) in anhydrous DMF (2 mL) was added compound 41 (50 mg) and NMM (12.7 μL) and the mixture stirred at room temperature under an argon atmosphere for 2 h. The reaction solution was then concentrated in vacuo, the residue dissolved in acetonitrile (500 μL) and purified by reverse phase C18-column chromatography, eluting with buffer A (v/v): water:0.05% trifluoroacetic acid and buffer B (v/v): acetonitrile:0.05% trifluoroacetic acid (70:30 v/v to 0:100 v/v). The organic solvent was removed in vacuo and the aqueous solvent removed by lyophilisation to give reagent 42 as a white solid (37.4 mg). m/z [M+Na]$^+$ (939, 80%), [M+H]$^+$ (917, 100%), [M+H−tBu]$^+$ (861, 50%).

Step 3: Synthesis of Reagent 43

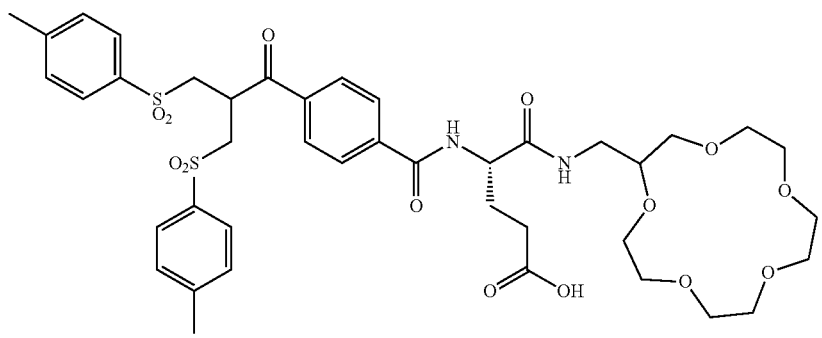

To a solution of reagent 42 (36 mg) in anhydrous dichloromethane (2 mL) was added trifluoroacetic acid (1 mL). The solution was stirred at room temperature for 80 min before the reaction mixture was concentrated in vacuo. The residue was then dissolved in acetonitrile:water (1:2 v/v, 1.5 mL) and the solvent removed by lyophilisation to give reagent 43 as a white solid (assumed quantitative yield). m/z [M+Na]$^+$ (883, 75%), [M+H]$^+$ (861, 100%).

Step 4: Synthesis of Reagent 40

To a solution of reagent 43 (5.6 mg) in anhydrous DMF (300 μL) at 0° C. was added HATU (2.4 mg) and the mixture stirred at 0° C. for 20 min. NMM (1 μL) was added and the solution stirred at 0° C. for a further 10 min. To a separate solution of Val-Cit-PAB-MMAE.TFA salt (6.6 mg) in anhydrous DMF (300 μL) at 0° C. was added NMM (1 μL) and the solution stirred at 0° C. for 30 min. The two solutions were then combined, additional quantities of HATU (2.4 mg) and NMM (1 μL) were added and the mixture allowed to warm to room temperature under stirring for 3.25 h. The reaction solution was then concentrated in vacuo, the residue dissolved in acetonitrile:DMSO (6:1 v:v, 350 μL) and purified by reverse phase C18-column chromatography, eluting with buffer A (v/v): water:0.05% trifluoroacetic acid and buffer B (v/v): acetonitrile:0.05% trifluoroacetic acid (70:30 v/v to 0:100 v/v). The organic solvent was removed in vacuo and the aqueous solvent removed by lyophilisation to give reagent 40 as a white solid (7 mg). m/z [M+Na]$^+$ (1989, 20%), [M+H]$^+$ (1967, 30%), [M+2Na]$^{2+}$ (1006, 30%), [M+H+Na]$^{2+}$ (995, 90%), [M+2H]$^{2+}$ (984, 100%).

Example 17: Synthesis of Conjugation Reagent 44 Comprising the Auristatin Cytotoxic Payload, MMAE

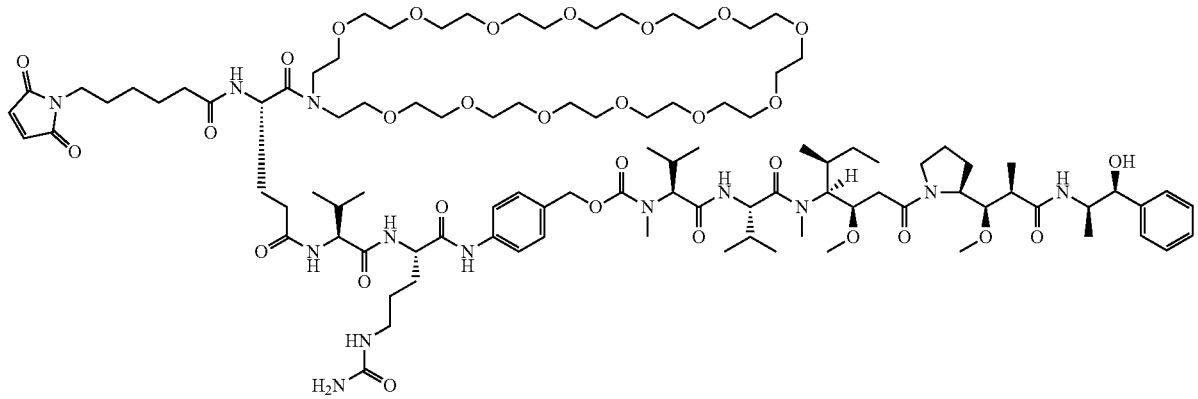

44

Step 1: Synthesis of Compound 45

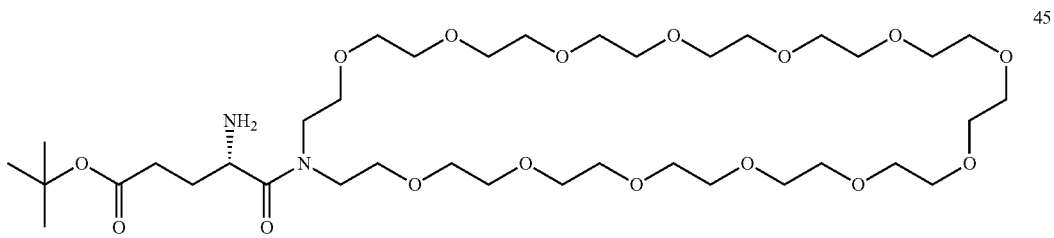 [SMILES: CC(C)(C)OC(=O)CC[C@H](N)C(=O)N1CCOCCOCCOCCOCCOCCOCCOCCOCCOCCOCCOCCOCCOCC1]

45

To a solution of Fmoc-Glu(OtBu)-OH (216 mg) in anhydrous DMF (8 mL) at 0° C. was added HATU (193 mg) and the mixture stirred at 0° C. for 20 min. NMM (56 µL) was added and the solution stirred at room temperature for a further 15 min. To a separate solution of compound 12 (284 mg) in anhydrous DMF (2 mL) was added NMM (56 µL) and the solution was stirred at 0° C. for 20 min. The two solutions were then combined, additional quantities of HATU (192 mg) and NMM (56 µL) were added and the mixture stirred at room temperature for 3.5 h. The reaction solution was then concentrated in vacuo before the residue was dissolved in ethyl acetate (50 mL). The solution was then washed with saturated sodium hydrogen carbonate solution (2×10 mL), followed by saturated brine solution (10 mL). The organic phase was then concentrated in vacuo to give crude Fmoc-L-Glu(OtBu)-aza-42-crown-14. m/z [M+Na]$^+$ (1046, 20%), [M+H]$^+$ (1023, 100%). To a solution of crude Fmoc-L-Glu(OtBu)-aza-42-crown-14 in DMF (7 mL) was added piperidine (320 µL) and the solution stirred at room temperature for 2 h. The reaction mixture was then concentrated in vacuo and purified by reverse phase C18-column chromatography, eluting with buffer A (v/v): water: 0.05% trifluoroacetic acid and buffer B (v/v): acetonitrile: 0.05% trifluoroacetic acid (95:5 v/v to 0:100 v/v). The organic solvent was removed in vacuo and the aqueous solvent removed by lyophilisation. The solid residue was then triturated with hexane (3×10 mL), the solid isolated by filtration and then dried in vacuo to give compound 45 as an off-white solid (201 mg). m/z [M+H]$^+$ (801, 100%).

Step 2: Synthesis of Reagent 46

To a solution of compound 45 (86 mg) in anhydrous dichloromethane (3 mL) was added N-succinimidyl 6-maleimidohexanoate (47 mg) and the solution stirred at room temperature. DIPEA (3×19 µL) was added to the reaction solution after 17.5, 22.5 and 24 h. The solution was then stirred for a further 18 h at room temperature before the reaction mixture was concentrated in vacuo, the residue dissolved in acetonitrile:DMSO (2:1 v/v) and purified by reverse phase C18-column chromatography, eluting with buffer A (v/v): water:0.05% trifluoroacetic acid and buffer B (v/v): acetonitrile:0.05% trifluoroacetic acid (90:10 v/v to 0:100 v/v). The organic solvent was removed in vacuo and the aqueous solvent removed by lyophilisation to give reagent 46 as a white solid (38 mg). m/z [M+Na]$^+$ (1016, 30%), [M+H]$^+$ (994, 20%).

Step 3: Synthesis of Reagent 47

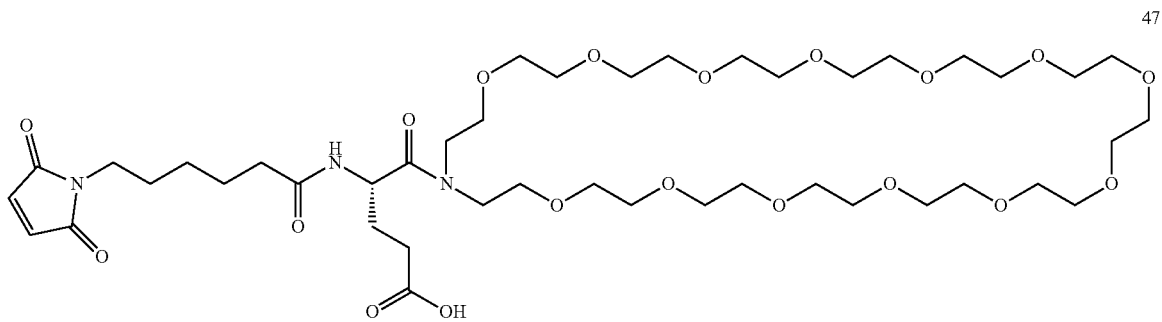

47

To a solution of reagent 46 (32 mg) in anhydrous dichloromethane (1.4 mL) was added trifluoroacetic acid (375 µL) and the solution stirred at room temperature for 2.5 h. Additional trifluoroacetic acid (375 µL) was then added and the solution stirred at room temperature for a further 2 h before the solution was concentrated in vacuo and the residue dried under high vacuum for 18 h. The residue was then dissolved in water (1 mL) and the solvent removed by lyophilisation to give reagent 47 as a colourless solid (assumed quantitative yield). m/z [M+Na]$^+$ (960, 20%), [M+H]$^+$ (938, 20%).

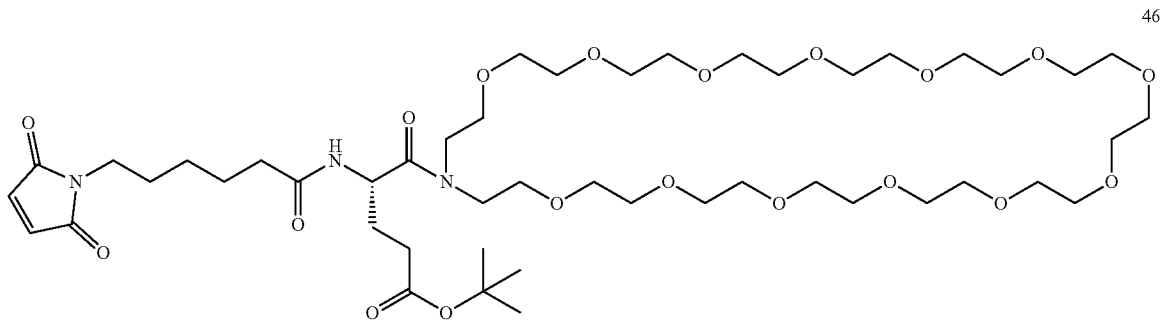 [SMILES: CC(C)(C)OC(=O)CC[C@H](NC(=O)CCCCCN1C(=O)C=CC1=O)C(=O)N1CCOCCOCCOCCOCCOCCOCCOCCOCCOCCOCCOCCOCCOCC1]

46

Step 4: Synthesis of Reagent 44

To a solution of reagent 47 (33.3 mg) in anhydrous DMF (750 µL) at 0° C. was added HATU (14.8 mg) and the mixture stirred at 0° C. for 20 min. NMM (4.3 µL) was added and the solution stirred at 0° C. for a further 15 min.

To a separate solution of Val-Cit-PAB-MMAE.TFA salt (45.7 mg) in anhydrous DMF (500 μL) at 0° C. was added NMM (4.3 μL) and the solution stirred at 0° C. for 25 min. The two solutions were then combined, additional quantities of HATU (14.8 mg) and NMM (4.3 μL) were added and the mixture allowed to warm to room temperature under stirring for 3.5 h. The solution was then concentrated in vacuo and purified by reverse phase C18-column chromatography, eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give reagent 44 as a white solid (48.3 mg). m/z [M+Na]$^+$ (2066, 20%), [M+H]$^+$ (2044, 25%), [M+H+Na]$^{2+}$ (1033, 50%), [M+2H]$^{2+}$ (1022, 100%).

Example 18: Synthesis of Conjugation Reagent 48 Comprising the Auristatin Cytotoxic Payload, MMAE

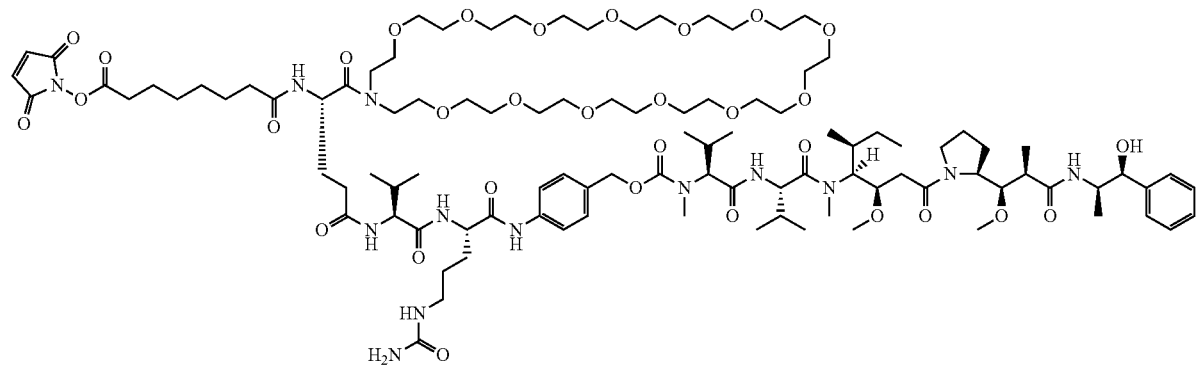

To a stirred solution of compound 13 (21.8 mg) in anhydrous DMF (500 μL) was added NMM (7.8 μL). This solution was then added dropwise over a period of 20 min to a stirred solution of suberic acid bis(N-hydroxysuccinimide ester) (43.8 mg) in anhydrous DMF (1.5 mL) at room temperature under an argon atmosphere. The reaction mixture was then stirred at room temperature for 20 h before the solution was concentrated in vacuo and purified by reverse phase C18-column chromatography, eluting with buffer A (v/v): water:0.05% trifluoroacetic acid and buffer B (v/v): acetonitrile:0.05% trifluoroacetic acid (90:10 v/v to 0:100 v/v). The organic solvent was removed in vacuo and the aqueous solvent removed by lyophilisation to give reagent 48 as a white solid (15.2 mg). m/z [M+Na]$^+$ (2126, 10%), [M+H]$^+$ (2104, 20%), [M+2Na]$^{2+}$ (1074, 50%), [M+Na+H]$^{2+}$ (1063, 50%) [M+2H]$^{2+}$ (1052, 100%).

Example 19: Conjugation of Reagent 44 to Brentuximab to Produce Antibody Drug Conjugate (ADC) 49 with DAR 4.6

Conjugation reagent 44 was conjugated to Brentuximab, giving rise to ADC 49, using a method analogous to that described within Example 6. Briefly, Brentuximab in 20 mM sodium phosphate buffer, 150 mM NaCl, 20 mM EDTA, pH 7.5, was reduced with TCEP (2 eq. per mAb) at 40° C. for 1 h. Conjugation of the reduced antibody with reagent 44 (6 eq. per mAb) was then performed. Reagent 44 was dissolved in acetonitrile to give a 4.8 mM stock solution. The reduced mAb solution was diluted to 4.2 mg/mL with 20 mM sodium phosphate buffer, 150 mM NaCl, 20 mM EDTA, pH 7.5. Reagent 44 and additional acetonitrile were added to the mAb solution to give a final antibody concentration of 4 mg/mL. The solution was mixed gently and incubated at 22° C. for 1 h. Excess reagent 44 was quenched with N-acetyl-L-cysteine (20 eq. over reagent) and the crude reaction mixture purified using an hydroxyapatite column equilibrated with 10 mM sodium phosphate, pH 6.7. The ADC was eluted from the column with a gradient of 10 mM sodium phosphate, 2 M NaCl, pH 6.7. Fractions containing ADC were pooled and concentrated (Vivaspin 20, 30 kDa PES membrane) and the concentrated sample was buffer exchanged into DPBS, pH 7.1-7.5 and sterile filtered. An average DAR of 4.6 was assigned to the conjugate using the method described in Example 3.

Example 20: Conjugation of Reagent 48 to Brentuximab to Produce Antibody Drug Conjugate (ADC) 50

Conjugation reagent 4 was conjugated to Brentuximab, giving rise to ADC 50. Briefly, reagent 48 was dissolved in DMF to give a 5.3 mM stock solution. To a Brentuximab solution (4.4 mg/mL in 20 mM sodium phosphate buffer, 150 mM NaCl, 20 mM EDTA, pH 7.5) was added reagent 48 (10 eq. per mAb) and additional DMF to give a final antibody concentration of 4 mg/mL. The solution was mixed gently and incubated at 22° C. for 1 h. The crude reaction solution was purified using an hydroxyapatite column equilibrated with 10 mM sodium phosphate, pH 6.7. The ADC was eluted from the column with a gradient of 10 mM sodium phosphate, 2 M NaCl, pH 6.7. Fractions containing ADC were pooled and concentrated (Vivaspin 20, 30 kDa PES membrane) and the concentrated sample was buffer exchanged into DPBS, pH 7.1-7.5 and sterile filtered. An average DAR of 4.1 for the conjugate was calculated from the relative peak intensities of the individual DAR species following mass spectrometry.

Example 21: Conjugation of Reagent 40 to Brentuximab to Produce Antibody Drug Conjugate (ADC) 51 with DAR 4

Conjugation reagent 40 was conjugated to Brentuximab giving rise to ADC 51 using a method analogous to that described in Example 3. Briefly, Brentuximab (5.2 mg/mL in 20 mM sodium phosphate, 150 mM NaCl, 20 mM EDTA, pH 7.5) was heated to 40° C. in a heating block for 15 min. TCEP (6 eq. per mAb) was added to the mAb solution, mixed gently and incubated at 40° C. for 1 h before being allowed to cool to 22° C. Conjugation reagent 40 was dissolved in DMF to give a 1.5 mM solution. Reagent 40 (5.6 eq. per mAb) was added to the mAb solution and the reaction was mixed gently and incubated at 22° C. for 16 h. The crude reaction mixture was mixed with an equal volume of 50 mM sodium phosphate, 4 M NaCl, pH 7 buffer and the resulting solution loaded onto a ToyoPearl Phenyl-650S HIC column equilibrated with 50 mM sodium phosphate, 2 M NaCl, pH 7. The ADC was eluted from the column with a gradient of 50 mM sodium phosphate, pH 7 (20% isopropanol). Fractions containing DAR 4 ADC were pooled and concentrated (Vivaspin 20, 30 kDa PES membrane) before the concentrated sample was buffer exchanged into PBS, pH 7.1-7.5, and sterile filtered (0.22 µm PVDF membranes).

Example 22: Analysis of ADC 31 by In Vitro Cell Viability Assay

Brentuximab conjugate 31, containing the payload MMAE, was prepared as described within Example 12. The cell viability assay using Karpas-299 cells was performed as described within Example 9. Concentration ranges used are described in Table 5. IC50 values obtained are listed in Table 6.

TABLE 5

| Cell line | Drug-conjugate | Concentration range |
|---|---|---|
| Karpas 299 | 31 | 0.4 nM-0.7 pM |
| Karpas 299 | MMAE (Free Drug) | 2.5 nM-1 pM |

TABLE 6

| Cell line | Drug-conjugate | $IC_{50}$ (nM) |
|---|---|---|
| Karpas 299 | 31 | 0.02 |
| Karpas 299 | MMAE (Free Drug) | 0.15 |

The IC50 value obtained for conjugate 31 shows that the ADC of the invention has potent cell killing properties in vitro.

Example 23: Analysis of ADC 38 by In Vitro Cell Viability Assay

Brentuximab conjugate 38, containing a duocarmycin payload, was prepared as described within Example 15. The cell viability assay using Karpas-299 cells was performed as described within Example 9. The concentration range used for the conjugate was 50 nM-0.6 pM and the IC50 value obtained was 0.14 nM.

The IC50 value obtained for conjugate 38 shows that the ADC of the invention has potent cell killing properties in vitro.

Example 24: Analysis of ADCs 49, 50 and 51 by In Vitro Cell Viability Assay

Brentuximab conjugates 49, 50 and 51, containing the payload MMAE, were prepared as described within Examples 19, 20 and 21 respectively. The cell viability assay using Karpas-299 cells was performed as described within Example 9. Concentration ranges used for each conjugate are described in Table 7. IC50 values obtained for each conjugate are listed in Table 8.

TABLE 7

| Cell line | Drug-conjugate | Concentration range |
|---|---|---|
| Karpas 299 | 49 | 1.0 nM-0.5 pM |
| Karpas 299 | 50 | 1.0 nM-0.5 pM |
| Karpas 299 | 51 | 1.0 nM-0.5 pM |
| Karpas 299 | MMAE (Free Drug) | 2.5 nM-1 pM |

TABLE 8

| Cell line | Drug-conjugate | $IC_{50}$ (nM) |
|---|---|---|
| Karpas 299 | 49 | 0.02 |
| Karpas 299 | 50 | 0.04 |
| Karpas 299 | 51 | 0.03 |
| Karpas 299 | MMAE (Free Drug) | 0.20 |

IC50 values obtained show that ADCs of the invention have potent cell killing properties in vitro.

Example 25: Karpas-299 Mouse Xenograft Studies Comparing Brentuximab-Drug Conjugates 14, 31, 32 (Comparative) and Adcetris® (Comparative)

Healthy female CB17-SCID mice (CBySmn.CB17-Prkdcscid/J, Charles River Laboratories) with an average body weight of 18.1 g were used for cell inoculation (Day 0). 24 to 72 h prior to tumour cell injection, the mice were γ-irradiated (1.44 Gy, $^{60}$Co). The animals were maintained in SPF health status according to the FELASA guidelines in housing rooms under controlled environmental conditions.

Tumours were induced by subcutaneous injection of $10^7$ Karpas-299 cells (T-anaplastic large cell lymphoma, ALCL) in 200 µL of RPMI 1640 into the right flank. Tumours were measured twice a week with calipers, and the volume was estimated using the formula:

$$\text{Tumour Volume (mm}^3\text{)} = \frac{\text{width}^2 \times \text{length}}{2}$$

Twelve days after tumour implantation (Day 12), the animals were randomised into groups of eight mice using Vivo manager® software (211 mm$^3$ mean tumour volume) and treatment was initiated. The animals from the vehicle group received a single intravenous (i.v.) injection of PBS. The treated groups were dosed with a single i.v. injection of ADC at 0.8 mg/kg, or Adcetris© (brentuximab vedotin) at 1 mg/kg.

Treatment tolerability was assessed by bi-weekly body weight measurement and daily observation for clinical signs of treatment-related side effects. Mice were euthanized when a humane endpoint was reached (e.g. 1,600 mm$^3$ tumour volume) or after a maximum of 9 weeks post-dosing. Asterisks within the graphs indicate where animals were euthanized.

The mean tumour volumes±standard error for each treatment are represented in FIGS. 2*a*, 3*a*, 4*a* and 5*a*, whereas individual tumour volumes for each treatment are represented in FIGS. 2*b*, 3*b*, 4*b* and 5*b*. All compounds were well tolerated.

Mice were dosed with 0.8 mg/kg of ADC 14, 31 or 32 or 1 mg/kg Adcetris® at day 12 post-tumour induction. Adcetris© was used at a higher dose to ensure that a reduction in tumour volume could be observed for this group. Each cohort dosed showed an initial reduction in tumour volume up to approximately day 20. However, after day 20, animals dosed with Adcetris® (comparative), displayed tumour re-growth in 7/8 animals, as shown by the increased average tumour volume and the individual tumour volumes in FIGS. 2a and 2b, respectively. The graph showing the mean tumour volume for this cohort (FIG. 2a) was no longer plotted when half of the animals had been euthanized due to tumour volume being greater than 1600 mm$^3$, in accordance with accepted practice. In this group, only 1/8 animals had no measureable tumour by the end of the study at day 71.

Figure 3A:
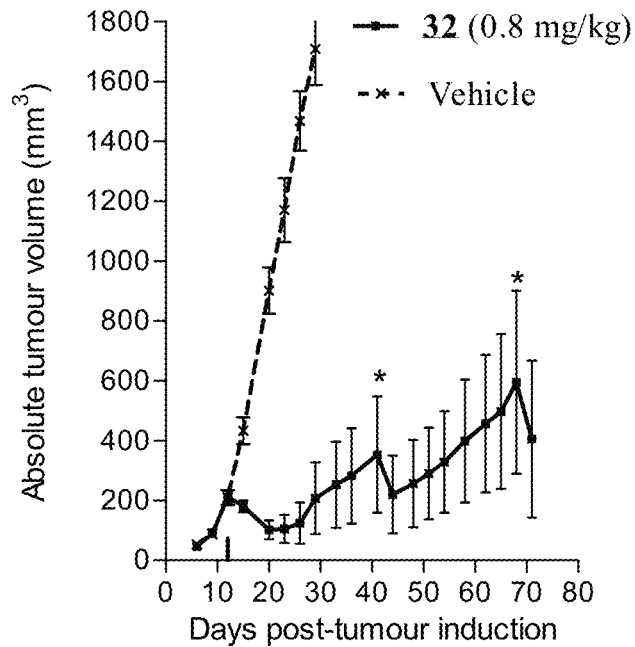
FIGS. 3A-3B show the results of mouse xenograft studies, with FIG. 3A showing (a) a plot of mean tumour volume±standard error over time in CB17-SCID mice following administration of vehicle or conjugate 32 (comparator) at 0.8 mg/kg on day 12 following tumour implantation.
Figure 3B:
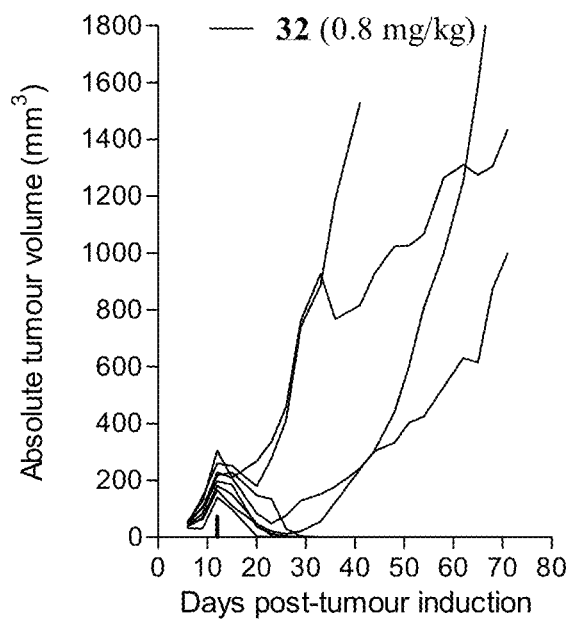

For ADC 32 (comparative), 4/8 animals had tumour re-growth after day 22 post-tumour induction. This is shown in FIGS. 3a and 3b, which display an increase in average and individual tumour volumes from day 22 to day 71. Within this group, two mice were euthanized at days 41 and 68 (as indicated by an asterisk), as their tumour volumes had reached the maximum allowable size for this model. Only 4/8 animals displayed no measureable tumour at day 71.

Figure 4A:
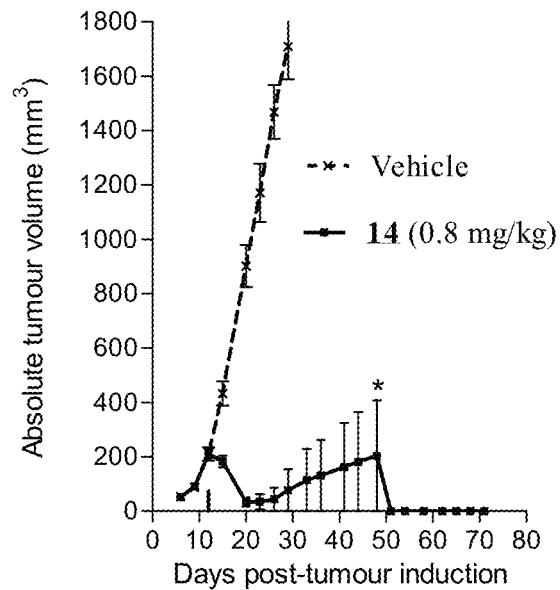
FIGS. 4A-4B show the results of mouse xenograft studies, with FIG. 4A showing (a) a plot of mean tumour volume±standard error over time in CB17-SCID mice following administration of vehicle or conjugate 14 at 0.8 mg/kg on day 12 following tumour implantation.
Figure 4B:
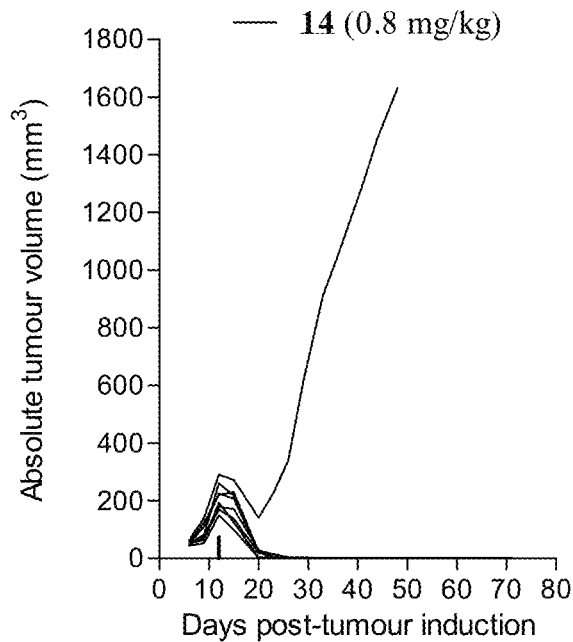
Figure 5A:
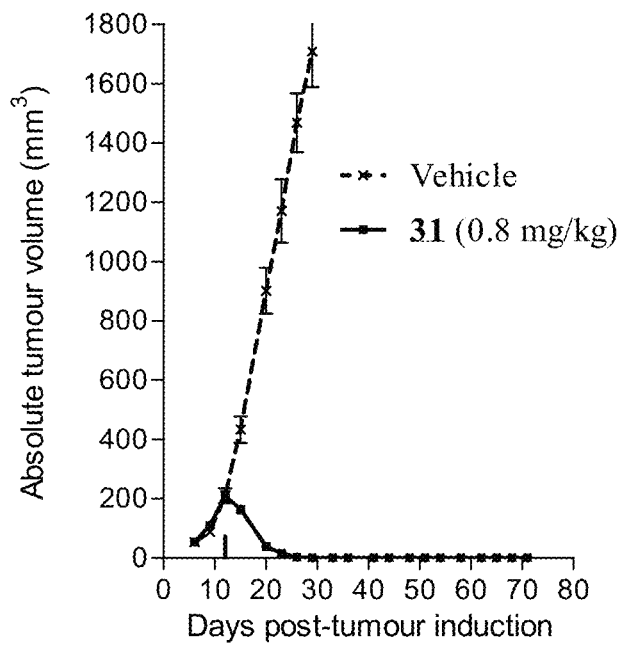
FIGS. 5A-5B show the results of mouse xenograft studies, with FIG. 5A showing (a) a plot of mean tumour volume±standard error over time in CB17-SCID mice following administration of vehicle or conjugate 31 at 0.8 mg/kg on day 12 following tumour implantation.
Figure 5B:
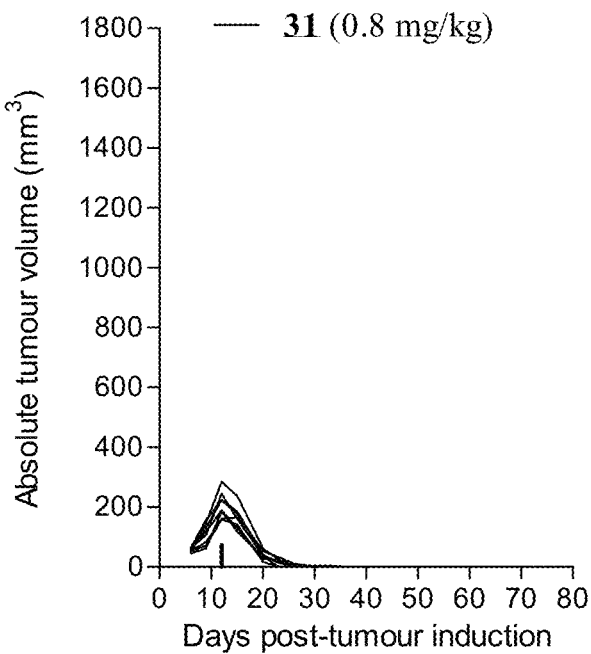

For ADC 14, the response rate was markedly better than ADC 32 (comparative), with 7/8 animals showing no measureable tumour volume at the end of the study at day 71 (see FIGS. 4a and 4b). Only one mouse showed any tumour re-growth, which was euthanized at day 48 post-tumour induction (as indicated by an asterisk). Even more impressively, for the cohort dosed with ADC 31, no animals showed any tumour re-growth at all after dosing. 8/8 animals survived to the end of the study at day 71 with no measureable tumour (see FIGS. 5a and 5b).

From these studies it is clear that ADCs of the invention are more efficacious than comparative ADCs of the prior art, with both 14 and 31 displaying better tumour-killing potencies than 32 and Adcetris©.

Further Inventive Aspects

While working in this area, the inventors have found that particularly advantageous results can be obtained when using a particular form of conjugation technology for conjugating a therapeutic, diagnostic and labelling agent to a peptide or protein. Accordingly, disclosed herein is an invention described by the following clauses.

1. A conjugate comprising a protein or peptide conjugated to a therapeutic, diagnostic or labelling agent via a linker, characterised in that the linker includes at least two ~(CH$_2$—CH$_2$—O—)~ units within a ring, and also includes a portion:

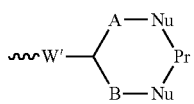

(III)

in which W' represents an electron withdrawing group or a group obtained by reduction of an electron withdrawing group, each of A and B independently represents a C$_{1-5}$alkylene or alkenylene chain, and Pr represents said protein or peptide bonded to A and B via nucleophiles Nu.

2. A conjugate as described in clause 1, which includes a portion:

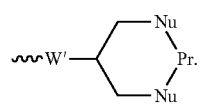

(IIIa)

3. A conjugate as described in either clause 1 or clause 2, in which each Nu represents a sulfur atom present in a cysteine residue in the protein or peptide Pr; or in which each Nu represents an imidazole group present in a polyhistidine tag attached to the protein or peptide Pr.

4. A conjugate as described in any one of the preceding clauses, in which W' represents a —CO— or —CH(OH)— group.

5. A conjugate as described in any one of the preceding clauses, which includes within said ring a unit of the formula ~(CH$_2$—CH$_2$—O—)$_x$~ in which x is a number of at least 2.

6. A conjugate as described in clause 5, in which x is from 2 to 50.

7. A conjugate as described in any one of the preceding clauses, in which the ring is attached via a single tethering atom within the ring to the rest of the linker at a single point or at two or more points; or in which the ring is attached via two or more tethering atoms within the ring to the rest of the linker at a single point or at two or more points.

8. A conjugate as claimed in claim 7, in which said ring has the formula:

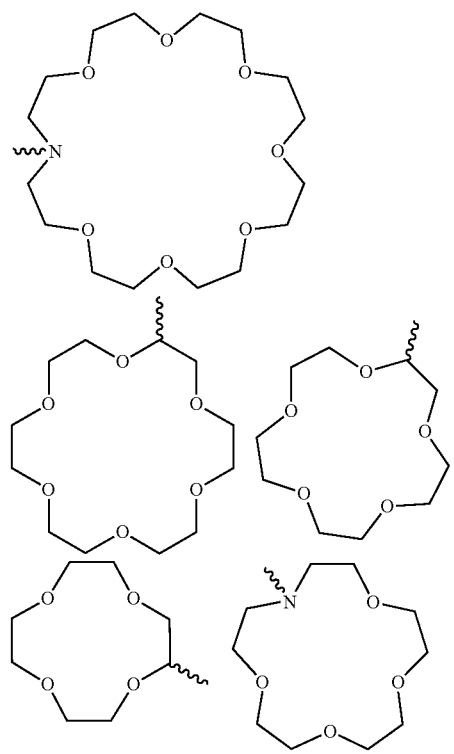

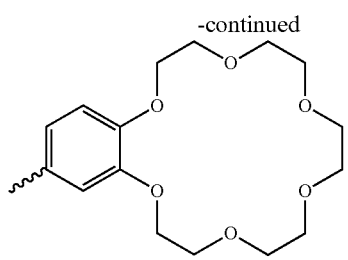

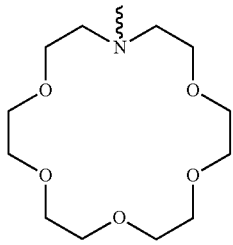

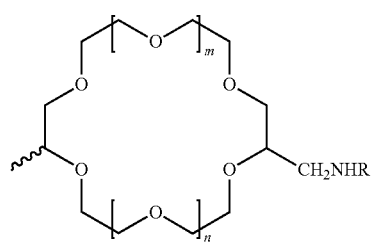

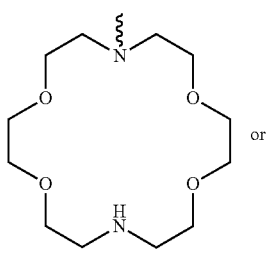

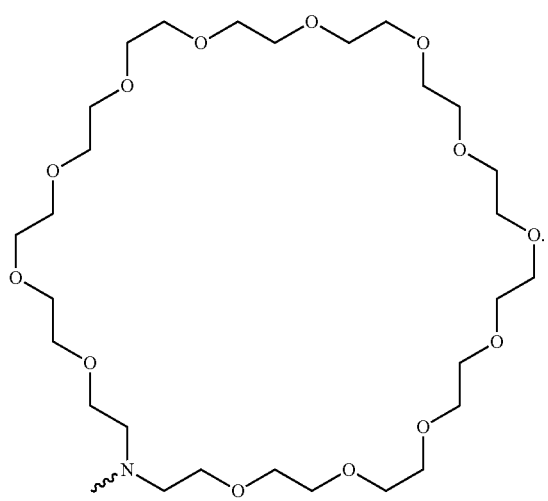

9. A conjugate as described in clause 7, in which the ring is attached via two or more tethering atoms within the ring to the rest of the linker at two or more points.

10. A conjugate as described in clause 9, in which said ring has the formula:

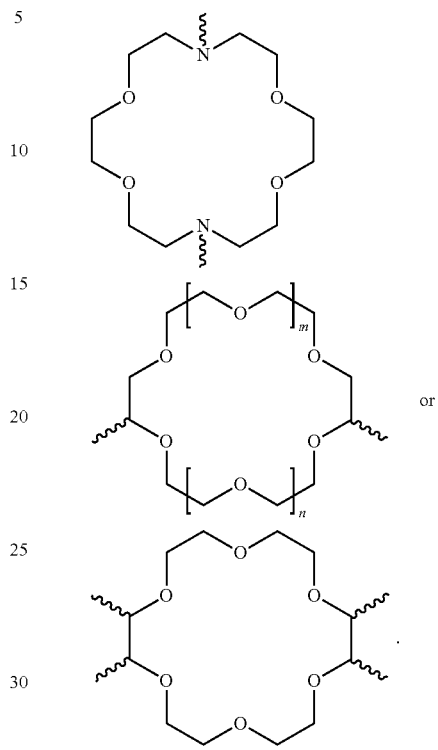

11. A conjugate as described in any one of the preceding clauses, which comprises an optionally substituted aryl or heteroaryl group immediately adjacent the group of formula III or IIIa; and which linker also includes a —NR$^a$·C(O)— or —C(O)·NR$^a$— group adjacent said aryl or heteroaryl group; wherein R$^a$ represents C$_{1-4}$ alkyl or hydrogen.

12. A conjugate as described in any one of the preceding clauses, which includes a therapeutic agent.

13. A conjugate as described in any one of the preceding clauses, in which the protein or peptide is an antibody or an antibody fragment.

14. A conjugating reagent comprising a functional group capable of reacting with a protein or peptide, which reagent also comprises a therapeutic, diagnostic or labelling agent and a linker which includes at least two ~(CH$_2$—CH$_2$—O—)~ units within a ring, and in which said functional group has the formula:

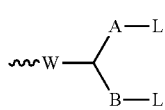

(I)

in which W represents an electron-withdrawing group; each of A and B independently represents a C$_{1-5}$alkylene or alkenylene chain; and either each L independently represents a leaving group, or both Ls together represent a leaving group; or

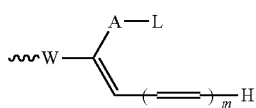
(II)

in which W and A have the meanings given above, L represents a leaving group, and m is 0 to 4.

15. A conjugating reagent as described in clause 14, in which said functional group has the formula:

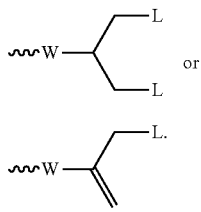
(Ia)

or (IIa)

16. A conjugating reagent as described in either clause 14 or clause 15, in which W represents a —CO— group.
17. A conjugating reagent as described in any one of clauses 14 to 16, which includes a feature according to any one of clauses 2 to 11.
18. A conjugating reagent as described in any one of clauses 14 to 17, in which the or each leaving group includes a portion —(CH$_2$CH$_2$O)$_n$— in which n is a number of two or more.
19. A conjugating reagent as described in clause 18, in which the or each leaving group has the formula —SP or —SO$_2$P, in which P represents a group which includes a portion —(CH$_2$CH$_2$O)$_n$— in which n is a number of two or more.
20. A process for the preparation of a conjugate as described in any one of clauses 1 to 13, which comprises reacting a protein or peptide with a conjugating reagent as described in any one of clauses 14 to 19.
21. A pharmaceutical composition which comprises a conjugate as described in any one of clauses 1 to 13, in which the payload is a therapeutic agent, together with a pharmaceutically acceptable carrier, and optionally together with a further active ingredient.

DETAILED DESCRIPTION OF THIS INVENTIVE ASPECT

The reagent of the invention may be represented schematically by the formula:

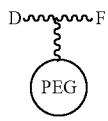

in which D represents the therapeutic, diagnostic or labelling agent, F represents a functional grouping capable of bonding to a protein or peptide, and

represents a ring which includes at least two ethylene glycol, ~(CH$_2$—CH$_2$—O—)~, units. The functional grouping F is capable of reacting with a protein or peptide as explained in more detail below.

The conjugate of the invention may be represented schematically by the formula:

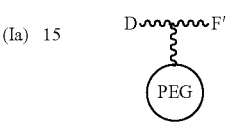

in which D represents the therapeutic, diagnostic or labelling agent, F' represents the protein or peptide bonded to the remainder of the conjugate via a protein or peptide bonding portion of the linker, and

represents a ring which includes at least two ethylene glycol, ~(CH$_2$—CH$_2$—O—)~, units.

The Polyethylene Glycol Ring

Throughout, "polyethylene glycol ring" should be understood to mean a ring which includes at least two ethylene glycol, ~(CH$_2$—CH$_2$—O—)~, units. The ring may include two or more separate ~(CH$_2$—CH$_2$—O—)~ units, or it may include one or more units of the formula ~(CH$_2$—CH$_2$—O—)$_x$~ in which x is a number of at least 2. The ring may contain one or more additional atoms to complete the cyclic structure. Additional atoms may for example be nitrogen, carbon, oxygen, sulfur, silicon and/or phosphorus atoms.

The ring may be attached via a single tethering atom within the ring to the rest of the linker at a single point, or it may be attached at two or more points. Alternatively, the ring may be attached via two or more tethering atoms within the ring to the rest of the linker at a single point, or it may be attached at two or more points. Tethering atoms may for example be nitrogen, carbon, phosphorus or silicon atoms, especially nitrogen and/or carbon atoms, and the atoms present at the point of attachment to the rest of the linker may for example be nitrogen or carbon atoms.

The following are schematic drawings of possible forms of attachment of the ring to the rest of the linker in conjugates or reagents of the invention, T representing a tethering atom in the ring, and PEG representing at least two ~(CH$_2$—CH$_2$—O—)~ units:

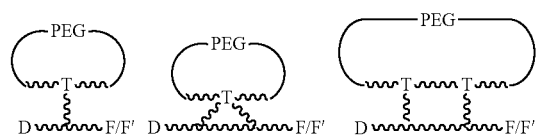

-continued

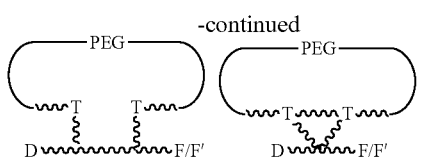

Specific examples of suitable rings include the following, where the symbol ~ indicates a point of incorporation of the ring into the linker:

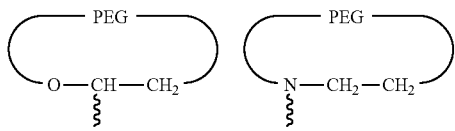

Preferably the ring is attached via a single tethering atom in the ring to the rest of the linker at a single point. In another preferred embodiment, the ring is attached via two or more tethering atoms within the ring to the rest of the linker at two or more points.

The ring may for example consist of ~($CH_2$—$CH_2$—O—)$_x$~ units in which x is at least 2, preferably from 2 to 20. Alternatively, the ring may contain ~($CH_2$—$CH_2$—O—)$_x$~ units in which x is at least 2, preferably from 2 to 50, especially from 2 to 20, but may also include one or more additional atoms as mentioned above, or may be derivatised in some other way.

Conjugates and reagents may be readily synthesised from crown ethers. Crown ethers are cyclic oligomers of ethylene glycol, and many different crown ethers are known, some of which consist entirely of ethylene glycol units, and some of which contain additional atoms within the ring. For example, aza-crown ethers contain a nitrogen atom, while diaza-crown ethers contain two nitrogen atoms. Many crown ethers are commercially available, and these provide convenient starting points for synthesis of the conjugates and reagents according to the invention. Crown ethers carrying functional groups through which they may be reacted with other compounds are known, for example crown ethers carrying carboxy, hydroxy, amino, or aldehyde groups are known, as are crown ethers fused to a benzene ring optionally carrying a functional group such as a carboxy, hydroxy, amino, isocyanate, nitro or aldehyde group.

Crown ethers are known to chelate cations, and perfluoro crown ethers have been described within U.S. Pat. No. 4,838,274 for use in MRI. Therefore the conjugates of the invention may be used in applications within imaging techniques such as MRI or PET.

Typical crown ethers which can be incorporated into the conjugates and reagents according to the invention include the structures shown below.

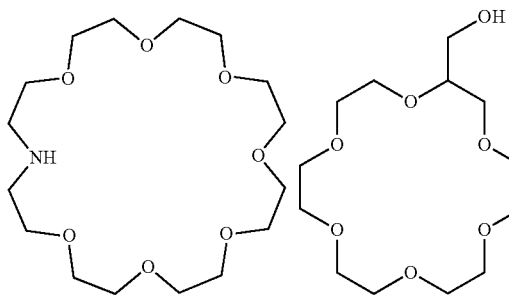

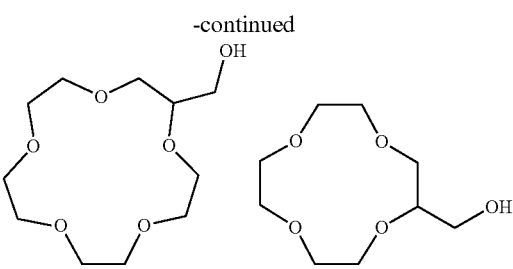

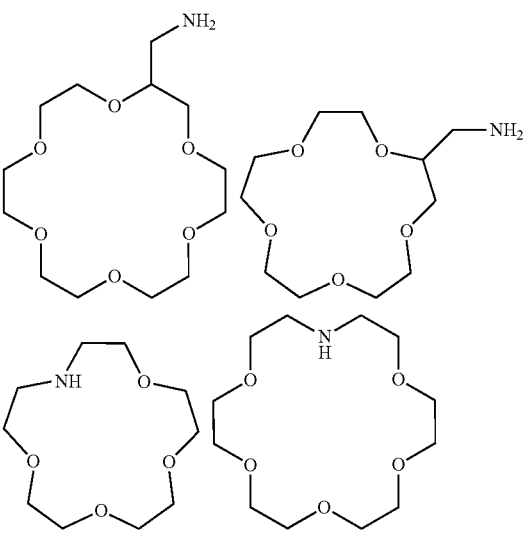

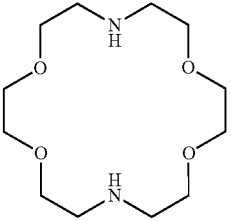

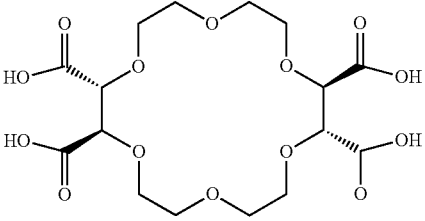

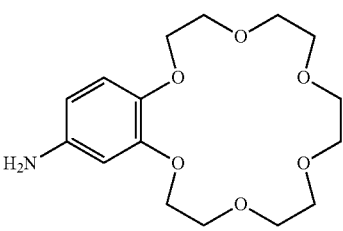

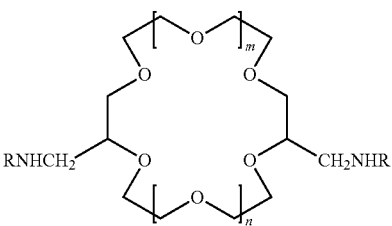

-continued

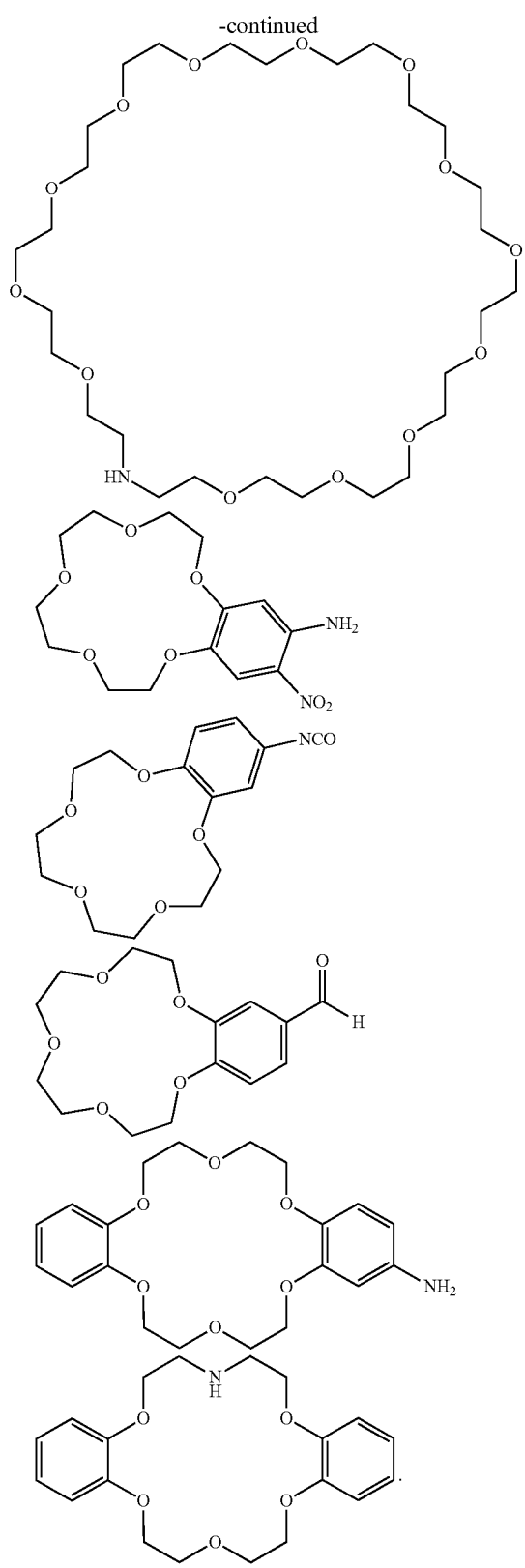

These may be incorporated into the linker of the conjugates and reagents of the invention by reaction through atoms, especially nitrogen atoms, present within the ring, or via groups, for example hydroxy, amino, carboxy, aldehyde, isocyanate or nitro groups, present on a side-chain. Rings having two functional groups or atoms can be attached to the rest of the linker of conjugates and reagents of the invention at two separate attachment points, hence being incorporated into the backbone of the linker. Typical linkages are as shown below:

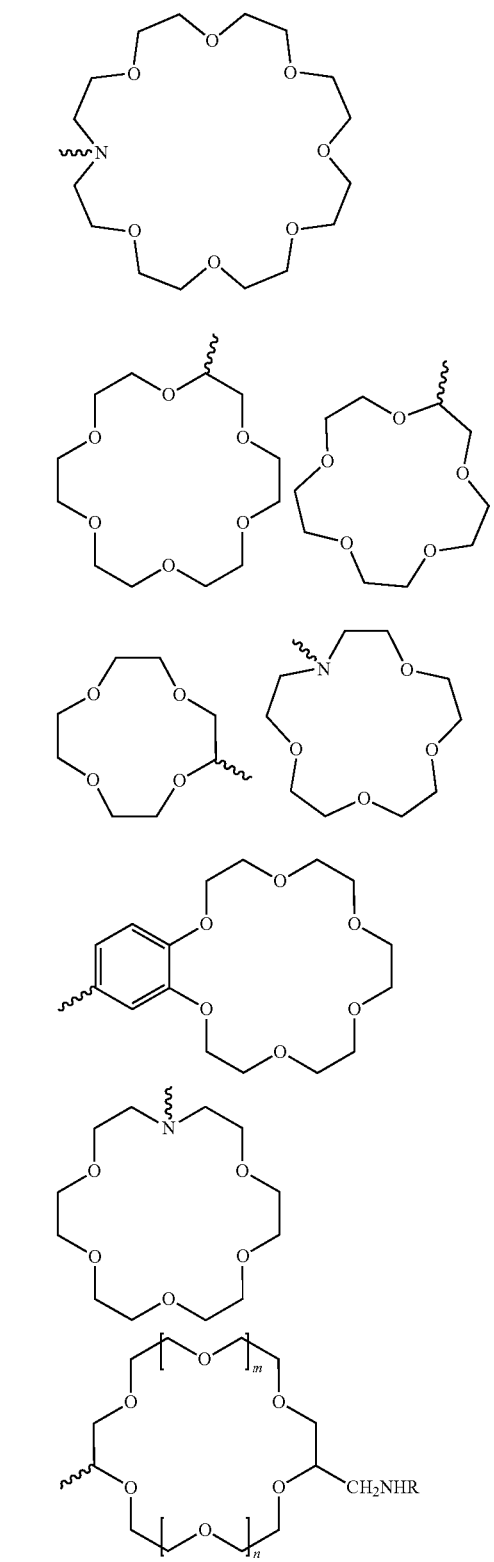

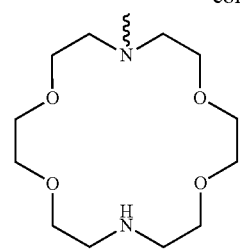

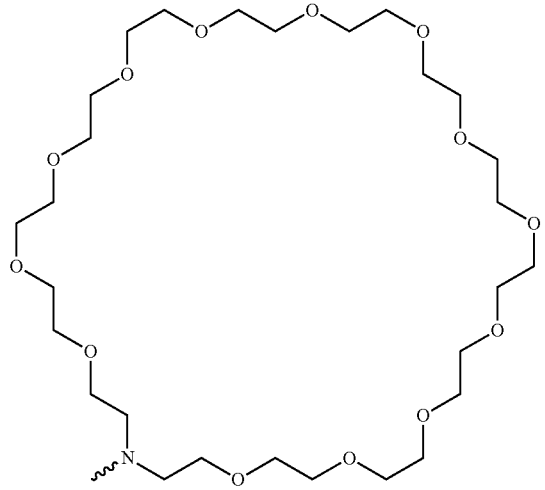

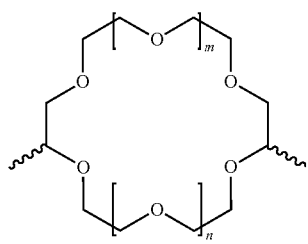

or

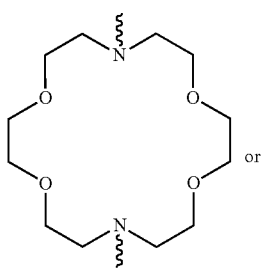

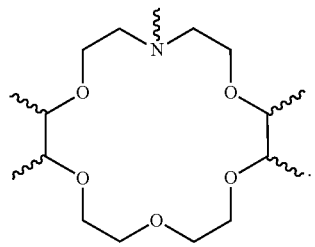

In addition to rings derived from crown ethers, rings derived from cryptands may be used in the present invention. Such rings are described for example in US 2014/0072900, and include the following:

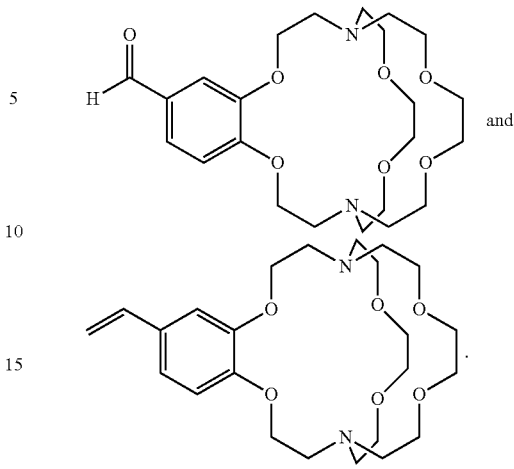

As an alternative to synthesising the conjugates and reagents of the invention starting from crown ethers or cryptands, it is possible to prepare a conjugate or reagent having a PEG chain attached at one end to the rest of the linker, and then to react the free end of the chain with a functional group present elsewhere on the linker, using conventional chemistry. In yet another alternative synthesis method, it is possible to prepare a conjugate or reagent containing two pendant PEG chains, and then to create a loop by reaction of appropriate reactive groups on each of the chains. Alkene and alkyne ring-closing metathesis may for example be used. All such methods of synthesis would be known to the skilled person, and permit the preparation of a very wide range of conjugates and reagents according to the invention, including ones in which the ring is incorporated into the backbone of the linker.

The conjugates and reagents of the invention may contain one ring including at least two ~(CH$_2$—CH$_2$—O—)~ units, or they may contain two or more such rings. The ring may be monocyclic, or it may be bi- or multi-cyclic. Two or more rings may be attached to or incorporated into the backbone of the linker, or they may be attached to each other, thus:

It will be understood that many different sizes and structures of rings are possible. The important feature of the invention is that a PEG chain forms part of a cyclic structure: this chain is not a linear PEG chain which forms part of the backbone of the linker, neither is it a pendant PEG chain which is tethered at one end to the linker but which has a free untethered end.

In one preferred embodiment, all of the PEG in the conjugate or reagent according to the invention is present within one or more rings. In another embodiment, PEG may also be present elsewhere in the linker, specifically in the backbone of the linker or in a group linking the ring to the backbone of the linker, and this is discussed in more detail below.

The total number of ~(CH$_2$—CH$_2$—O—)~ units present in the conjugates and reagents of the invention will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications.

As with the total quantity of PEG present in the conjugates or reagents of the invention, the number of ~($CH_2$—$CH_2$—O—)~ units present in the ring will depend on the intended application. For example the cyclic PEG portion may have a molecular weight up to 3,000 g/mole. However, cyclic groups containing as few as 2 ethylene glycol units, for example from 2 to 50 ethylene glycol units, are useful for some applications, and are present as a cyclic PEG group in one preferred embodiment of the invention. PEG-containing rings with 2, 3, 4, 5, 6, 7, 8, 9, 10, 11, 12, 13, 14, 15, 16, 17, 18, 19 or 20 repeat units, or 24, 36, 40 or 48 repeat units, may for example be used.

Conjugating Reagents and Processes

The conjugating reagent according to the invention is capable of reacting with two nucleophiles. If two or more leaving groups are present, these may be the same or different. Alternatively, a conjugating reagent may contain a single group which is chemically equivalent to two leaving groups and which single group is capable of reacting with two nucleophiles.

Nucleophilic groups include sulfur atoms and amine groups, and nucleophilic groups in proteins are for example provided by cysteine, lysine or histidine residues. In one preferred embodiment of the invention, a nucleophilic group is a sulfur atom present in a cysteine residue present in the protein. Such structures may be obtained by reduction of a disulfide bond present in the protein. In another embodiment, a nucleophilic group may be an imidazole group present in a histidine residue present in a polyhistidine tag attached to the protein.

The conjugating reagent contains the functional grouping F:

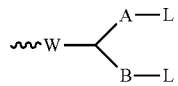
(I)

in which W represents an electron-withdrawing group, for example a keto group, an ester group —O—CO—, or a sulfone group —$SO_2$—; each of A and B independently represents a $C_{1-5}$alkylene or alkenylene chain; and either each L independently represents a leaving group, or both Ls together represent a leaving group. When reagents containing such groups react with proteins, a first leaving group L is lost to form in situ a conjugating reagent containing a functional grouping of formula:

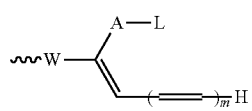
(II)

in which m is 0 to 4, which reacts with a first nucleophile. The second leaving group L is then lost, and reaction with a second nucleophile occurs. As an alternative to using a reagent containing the functional grouping I as starting material, reagents containing the functional grouping II may be used, as the functional groupings I and II are chemical equivalents of each other.

These conjugating reagents of the invention are of the general type disclosed in WO 2005/007197 and WO 2010/100430. Such reagents may for example be used to target two sulfur atoms obtained by reduction of a disulfide bond in a protein, or imidazole groups present in histidine residues present in a polyhistidine tag attached to a protein. It has been found that the incorporation of a cyclic PEG group according to the present invention into reagents of this type gives particularly good results, with conjugation reactions occurring efficiently to produce stable conjugates with a high degree of homogeneity.

A leaving group L may for example be —SP, —OP, —$SO_2$P, —O$SO_2$P, —$N^+$P$R^2R^3$, halogen, or —OØ, in which P represents a hydrogen atom or an alkyl (preferably $C_{1-6}$alkyl), aryl (preferably phenyl), or alkyl-aryl (preferably $C_{1-6}$alkyl-phenyl) group, or is a group which includes a portion —($CH_2CH_2O$)$_n$— in which n is a number of two or more, and each of $R^2$ and $R^3$ independently represents a hydrogen atom, a $C_{1-4}$alkyl group, or a group P, and Ø represents a substituted aryl, especially phenyl, group, containing at least one substituent, for example —CN, $CF_3$, —$NO_2$, —$CO_2R^a$, —COH, —$CH_2OH$, —$COR^a$, —$OR^a$, —$OCOR^a$, —$OCO_2R^a$, —$SR^a$, —$SOR^a$, —$SO_2R^a$, —$NHCOR^a$, —$NR^aCOR^a$, —$NHCO_2R^a$, —$NR^aCO_2R^a$, —NO, —NHOH, —$NR^a$OH, —CH=N—$NR^a$ $COR^a$, —$N^+R^a_3$, —, halogen, especially chlorine or, especially, fluorine, —C≡$CR^a$, and —CH=$CR^a_2$, in which each $R^a$ independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is preferred.

Conjugating reagents in which P represents a group which includes a portion —($CH_2CH_2O$)$_n$— in which n is a number of two or more are the subject of our copending application GB 1418186, published as WO 2016/059377, and are described above.

An especially preferred leaving group L present in a novel conjugating reagent according to the present invention is —SP or —$SO_2$P, especially —$SO_2$P. Within this group, one preferred embodiment is where P represents a phenyl or, especially, a tolyl group. Another preferred embodiment is where P represents a group which includes a portion —($CH_2CH_2O$)$_n$—, especially one in which n has one of the values mentioned above, especially 7. An especially preferred leaving group L is —$SO_2$—($CH_2CH_2O$)$_n$—H/Me, especially —$SO_2$—($CH_2CH_2O$)$_7$—HMe.

Throughout this Specification, any reference to a leaving group L should be understood to include a specific reference to these preferred groups, especially —$SO_2$—($CH_2CH_2O$)$_n$—H/Me, and more especially —$SO_2$—($CH_2CH_2O$)$_7$—H/Me.

Preferably W represents a keto group. Preferably each of A and B represents —$CH_2$—.

Reagents of the formula I and II above form conjugates which include the grouping F'':

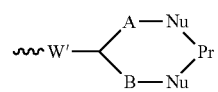
(III)

in which W' represents an electron withdrawing group or a group obtained by reduction of an electron withdrawing group, and Pr represents a protein or peptide bonded to A and B via nucleophiles Nu. The immediate product of the conjugation process (as described in more detail below) is a conjugate which contains an electron-withdrawing group W. However, the conjugation process is reversible under suitable conditions. This may be desirable for some applications, for example where rapid release of the protein is required, but for other applications, rapid release of the protein may be undesirable. It may therefore be desirable to stabilise the conjugates by reduction of the electron-withdrawing moiety to give a moiety which prevents release of the protein. Accordingly, the conjugation process may comprise an additional optional step of reducing the electron withdrawing group in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin (II) chloride, alkoxides such as aluminium alkoxide, and lithium aluminium hydride.

Thus, for example, a moiety W containing a keto group may be reduced to a moiety containing a CH(OH) group; an ether group CH·OR$^a$ may be obtained by the reaction of a hydroxy group with an etherifying agent; an ester group CH·O·C(O)R$^a$ may be obtained by the reaction of a hydroxy group with an acylating agent; an amine group CH·NH$_2$, CH·NHR$^a$ or CH·NR$^a_2$ may be prepared from a ketone by reductive amination; or an amide CH·NHC(O)R$^a$ or CH·N(C(O)R$^a$)$_2$ may be formed by acylation of an amine. A sulfone may be reduced to a sulfoxide, sulfide or thiol ether.

Preferably the groupings F' and F have the formula:

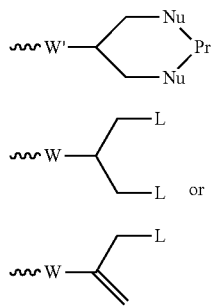

(IIIa)

(Ia)

(IIa)

especially

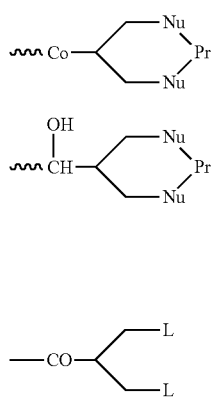

(IIIb)

(IIIc)

(Ib)

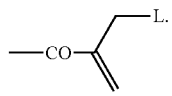

(IIb)

In the above formulae, preferred leaving groups are as described above. Preferably each Nu is a sulfur atom.

Conjugating reagents according to the invention may contain more than one functional grouping for reaction with a protein. For example, a reagent may contain a functional grouping, preferably of formula I or II, at one end of the molecule, and one or more additional functional groupings, elsewhere in the molecule. Such structures are described in for example Belcheva et al, J. Biomater. Sci Polymer Edn. 9(3), 207-226 and are useful in the synthesis of conjugates containing multiple proteins.

The novel conjugating reagents of the present invention may be prepared by methods analogous to known methods. Specific reactions are illustrated in the Examples.

Conjugating reagents according to the invention may be reacted with a protein or peptide to form a conjugate according to the invention, and such a reaction forms a further aspect of the invention.

A key feature of using conjugating reagents of the formulae I or II is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. In reagents containing the functional grouping I, a leaving group serves to mask a latent conjugated double bond that is not exposed until after the first alkylation has occurred to give a reagent including the functional grouping II and bis-alkylation results from sequential and interactive Michael and retro-Michael reactions. The cross-functional alkylating agents may contain multiple bonds conjugated to the double bond or between the leaving group and the electron withdrawing group.

Where bonding to the protein is via two sulfur atoms derived from a disulfide bond in the protein, the process may be carried out by reducing the disulfide bond following which the reduced product reacts with the reagent according to the invention. Preferably the disulfide bond is reduced and any excess reducing agent is removed, for example by buffer exchange, before the conjugating reagent is introduced. The disulfide bond can be reduced, for example, with dithiothreitol, mercaptoethanol, or tris-carboxyethylphosphine using conventional methods.

Conjugation reactions may be carried out under similar conditions to known conjugation processes, including the conditions disclosed in WO 2005/007197, WO 2009/047500, WO 2014/064423, WO 2014/064424, and WO 2015/057699. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone, DMSO, DMF, MeCN) are typically conducted at temperatures up to ambient. In one preferred embodiment, the reaction is carried out in aqueous buffer which may contain a proportion of organic solvent, for example up to 20% by volume of organic solvent, typically from 5 to 20% by volume of organic solvent.

The protein can be effectively conjugated using a stoichiometric equivalent or a slight excess of conjugating reagent. However, it is also possible to conduct the conjugation reaction with an excess stoichiometry of conjugating reagent, and this may be desirable for some proteins. The excess reagent can easily be removed, for example by ion exchange chromatography or HPLC, during subsequent purification of the conjugate.

Of course, it is possible for more than one conjugating reagent to be conjugated to a protein, where the protein contains sufficient suitable attachment points. For example, in a protein which contains two different disulfide bonds, or in a protein which contains one disulfide bond and also carries a polyhistidine tag, it is possible to conjugate two molecules of reagent per molecule of protein, and such conjugates form part of the present invention.

The Payload, the Protein, the Linker, and Pharmaceutical Compositions and Utility All material present in the sections "The payload", "The protein", "The Linker", and "Pharmaceutical compositions and utility" above applies to this aspect of the invention.

The invention claimed is:

1. A conjugate comprising a protein or peptide conjugated to a therapeutic agent via a linker, characterised in that the linker includes a unit of the formula ~(CH$_2$—CH$_2$—O—)$_x$~ within a ring, in which x is a number from 2 to 50, said ring being attached via a single tethering atom within the ring to the rest of the linker, or said ring being attached via two tethering atoms within the ring to the rest of the linker at a single point, wherein the conjugate is formed from conjugation of said protein or peptide with a reagent represented schematically by the formula:

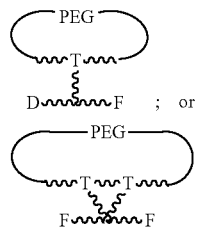

in which:

D represents said therapeutic agent;

each T independently represents a tethering atom in the ring;

PEG represents said unit of the formula ~(CH$_2$—CH$_2$—O—)$_x$~ within a ring, in which x is a number from 2 to 50; and F represents a functional group for bonding to said protein or peptide wherein the functional group is a maleimide or derivative thereof according to one of the following formulae:

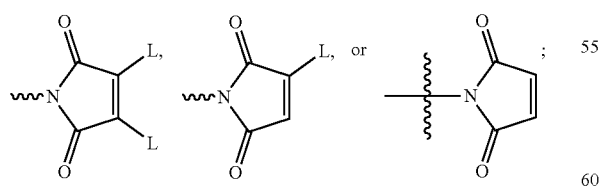

wherein the nitrogen atom of the maleimide ring is connected to the linker and L represents a leaving group.

2. A conjugate as claimed in claim 1, in which said ring is attached via a single tethering atom in the ring to the rest of the linker at a single point.

3. A conjugate as claimed in claim 2, in which said ring has the formula:

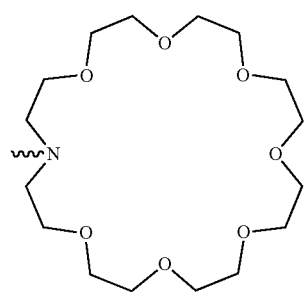

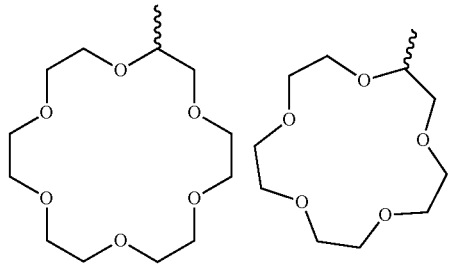

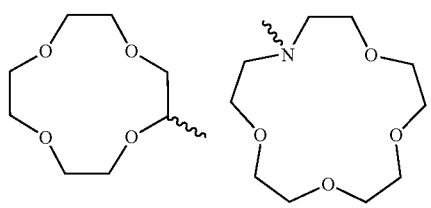

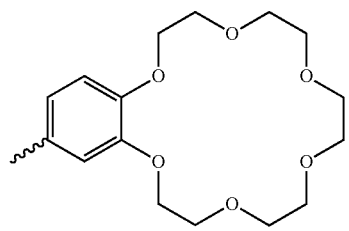

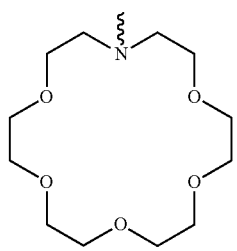

-continued

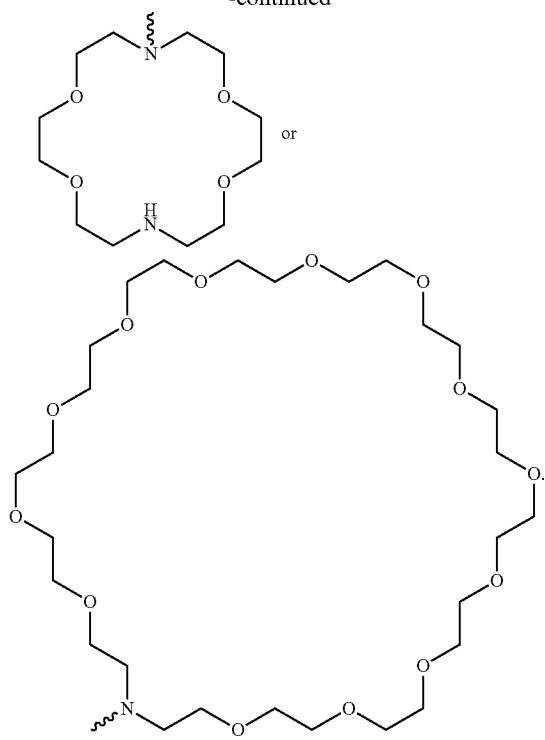

4. A conjugate as claimed in claim 1, in which the protein or peptide is an antibody or an antibody fragment.

5. A process for the preparation of a conjugate as claimed in claim 1, comprising reacting a protein or peptide with a conjugating reagent, wherein said conjugating reagent comprises a functional group capable of reacting with the protein or peptide and also comprises a therapeutic agent and a linker which includes a unit of the formula $\sim(CH_2-CH_2-O-)_x\sim$ within a ring, in which x is a number from 2 to 50, said ring being attached via a single tethering atom within the ring to the rest of the linker, or said ring being attached via two tethering atoms within the ring to the rest of the linker at a single point, and wherein said conjugating reagent is represented schematically by the formula:

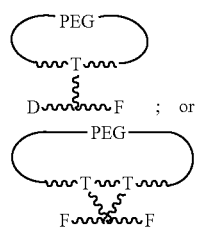

in which:
D represents said therapeutic agent;
each T independently represents a tethering atom in the ring;
PEG represents said unit of the formula $\sim(CH_2-CH_2-O-)_x\sim$ within a ring, in which
x is a number from 2 to 50; and
F represents a functional group for bonding to said protein or peptide, wherein the functional group is a maleimide or derivative thereof according to one of the following formulae:

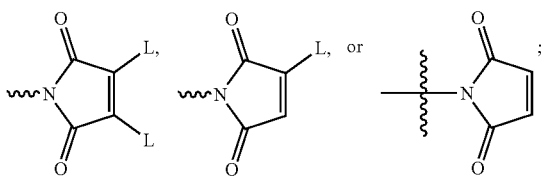

wherein the nitrogen atom of the maleimide ring is connected to the linker and L represents a leaving group.

6. A pharmaceutical composition which comprises a conjugate as claimed in claim 1 together with a pharmaceutically acceptable carrier, optionally together with a further active ingredient.

* * * * *

UNITED STATES PATENT AND TRADEMARK OFFICE
CERTIFICATE OF CORRECTION

PATENT NO. : 11,865,183 B2  
APPLICATION NO. : 17/591621  
DATED : January 9, 2024  
INVENTOR(S) : Antony Godwin et al.

Page 1 of 1

It is certified that error appears in the above-identified patent and that said Letters Patent is hereby corrected as shown below:

In the Claims

In Claim 1, Column 99, the second PEG formula, Line 37, " 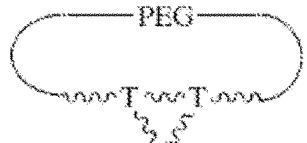 " should read 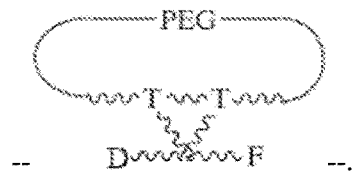 .

In Claim 5, Column 102, the second PEG formula, Line 13, " 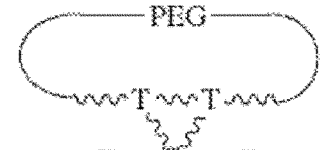 " should read  .

Signed and Sealed this  
Nineteenth Day of March, 2024

Katherine Kelly Vidal  
*Director of the United States Patent and Trademark Office*